US009452197B2

(12) United States Patent
Seehra et al.

(10) Patent No.: US 9,452,197 B2
(45) Date of Patent: Sep. 27, 2016

(54) ANTAGONISTS OF BMP9, BMP10, ALK1 AND OTHER ALK1 LIGANDS, AND USES THEREOF

(71) Applicant: Acceleron Pharma, Inc., Cambridge, MA (US)

(72) Inventors: Jasbir Seehra, Lexington, MA (US); John Knopf, Carlisle, MA (US); Robert S. Pearsall, North Reading, MA (US); Asya Grinberg, Lexington, MA (US); Ravindra Kumar, Acton, MA (US)

(73) Assignee: Acceleron Pharma, Inc., Cambridge, MA (US)

( * ) Notice: Subject to any disclaimer, the term of this patent is extended or adjusted under 35 U.S.C. 154(b) by 0 days.

(21) Appl. No.: 14/142,094

(22) Filed: Dec. 27, 2013

(65) Prior Publication Data

US 2014/0227254 A1 Aug. 14, 2014

Related U.S. Application Data

(63) Continuation of application No. 12/467,170, filed on May 15, 2009, now Pat. No. 8,642,031, and a continuation-in-part of application No. 11/982,738, filed on Nov. 2, 2007, now Pat. No. 8,455,428.

(60) Provisional application No. 61/053,644, filed on May 15, 2008, provisional application No. 60/856,592, filed on Nov. 2, 2006.

(51) Int. Cl.

| | |
|---|---|
| ***A61K 39/00*** | (2006.01) |
| ***A61K 38/17*** | (2006.01) |
| ***C07K 14/71*** | (2006.01) |
| ***C07K 16/22*** | (2006.01) |
| ***A61K 39/395*** | (2006.01) |
| ***A61K 45/06*** | (2006.01) |
| ***C07K 14/47*** | (2006.01) |

(52) U.S. Cl.

CPC ....... *A61K 38/1709* (2013.01); *A61K 39/3955* (2013.01); *A61K 45/06* (2013.01); *C07K 14/47* (2013.01); *C07K 14/71* (2013.01); *C07K 16/22* (2013.01); *A61K 2039/505* (2013.01); *C07K 2317/76* (2013.01); *C07K 2319/30* (2013.01)

(58) Field of Classification Search

None

See application file for complete search history.

(56) References Cited

U.S. PATENT DOCUMENTS

| | | | |
|---|---|---|---|
| 5,350,836 | A | 9/1994 | Kopchick et al. |
| 5,587,458 | A | 12/1996 | King et al. |
| 5,660,827 | A | 8/1997 | Thorpe et al. |
| 5,719,120 | A | 2/1998 | Letarte et al. |
| 5,830,847 | A | 11/1998 | Letarte et al. |
| 5,928,641 | A | 7/1999 | Seon |
| 5,968,752 | A | 10/1999 | Ichijo et al. |
| 6,015,693 | A | 1/2000 | Letarte et al. |
| 6,075,181 | A | 6/2000 | Kucherlapati et al. |
| 6,114,598 | A | 9/2000 | Kucherlapati et al. |
| 6,150,584 | A | 11/2000 | Kucherlapati et al. |
| 6,162,963 | A | 12/2000 | Kucherlapati et al. |
| 6,190,660 | B1 | 2/2001 | Seon |
| 6,200,566 | B1 | 3/2001 | Seon |
| 6,316,217 | B1 | 11/2001 | Miyazono et al. |
| 6,417,429 | B1 | 7/2002 | Hein et al. |
| 6,692,925 | B1 | 2/2004 | Miyazono et al. |
| 7,045,534 | B2 | 5/2006 | Cooke et al. |
| 7,067,110 | B1 | 6/2006 | Gilles et al. |
| 7,077,836 | B2 | 7/2006 | Lary et al. |
| 7,125,541 | B2 | 10/2006 | Thorpe et al. |
| 7,537,762 | B2 | 5/2009 | North et al. |
| 7,592,428 | B1 | 9/2009 | Miyazono et al. |
| 8,080,646 | B2 | 12/2011 | North et al. |
| 8,158,584 | B2 | 4/2012 | Grinberg et al. |
| 8,455,428 | B2 | 6/2013 | Grinberg et al. |
| 8,642,031 | B2 | 2/2014 | Seehra et al. |
| 2002/0137668 | A1 | 9/2002 | Holaday et al. |
| 2002/0165361 | A1 | 11/2002 | Lee et al. |
| 2003/0012792 | A1 | 1/2003 | Holaday et al. |
| 2003/0220297 | A1* | 11/2003 | Berstein ............... A61K 31/675 514/80 |
| 2005/0048607 | A1 | 3/2005 | Miyazono et al. |
| 2005/0249723 | A1 | 11/2005 | Lazar |
| 2007/0065444 | A1 | 3/2007 | North et al. |
| 2008/0131910 | A1 | 6/2008 | Miyazono et al. |
| 2008/0175844 | A1 | 7/2008 | Grinberg et al. |
| 2009/0226441 | A1 | 9/2009 | Yan et al. |
| 2009/0304691 | A1 | 12/2009 | Seehra et al. |

(Continued)

FOREIGN PATENT DOCUMENTS

| | | |
|---|---|---|
| EP | 0677104 B1 | 10/1995 |
| EP | 1071765 A1 | 1/2001 |

(Continued)

OTHER PUBLICATIONS

David et al Blood 109:1953-61, 2007, IDS, p. 4, item 7, filed on Apr. 23, 2014.*

International Search Report and Written Opinion mailed Jan. 16, 2014 for Application No. PCT/US2013/063467.

International Preliminary Report on Patentability mailed Apr. 16, 2015 for Application No. PCT/US2013/063467.

International Search Report and Written Opinion mailed Oct. 20, 2014 for Application No. PCT/US2013/063467.

(Continued)

*Primary Examiner* — Lei Yao

(74) *Attorney, Agent, or Firm* — Wolf, Greenfield & Sacks, P.C.

(57) ABSTRACT

In certain aspects, the present disclosure relates to the insight that a polypeptide comprising a ligand-binding portion of the extracellular domain of activin-like kinase I (ALK1) polypeptide may be used to inhibit angiogenesis in vivo, particularly in mammals suffering angiogenesis-related disorders. In certain aspects, the disclosure demonstrates that antagonists of BMP9 and/or BMP10, ligands for ALK1, may also be used to inhibit angiogenesis in vivo.

7 Claims, 19 Drawing Sheets

(56) References Cited

U.S. PATENT DOCUMENTS

2009/0311272 A1 12/2009 Grinberg et al.
2012/0183543 A1 7/2012 Buckler et al.
2013/0039910 A1 2/2013 Grinberg et al.
2013/0040896 A1 2/2013 Grinberg et al.
2013/0344067 A1 12/2013 Grinberg et al.
2014/0193425 A1 7/2014 Knopf et al.
2015/0202260 A1 7/2015 Grinberg et al.
2015/0299677 A1 10/2015 Alimzhanov et al.

FOREIGN PATENT DOCUMENTS

KR 2009-0085662 A 8/2009
WO WO 92/15602 A1 9/1992
WO WO 94/10187 A1 5/1994
WO WO 94/11502 A2 5/1994
WO WO 97/07135 A2 2/1997
WO WO 97/45450 A1 12/1997
WO WO 99/046386 A1 9/1999
WO WO 01/54723 A1 8/2001
WO WO 02/11785 A2 2/2002
WO WO 02/20614 A2 3/2002
WO WO 03/055443 A2 7/2003
WO WO 03/064628 A2 8/2003
WO WO 03/093293 A2 11/2003
WO WO 2004/003163 A2 1/2004
WO WO 2004/039248 A2 5/2004
WO WO 2005/010049 A2 2/2005
WO WO 2005/044849 A2 5/2005
WO WO 2005/116052 8/2005
WO WO 2005/113590 A2 12/2005
WO WO 2005/116850 A2 12/2005
WO WO 2006/091930 A2 8/2006
WO WO 2007/040912 A2 4/2007
WO WO 2007/143023 A1 12/2007
WO WO 2008/057461 A2 5/2008
WO WO 2009/061807 5/2009
WO WO 2009/134428 11/2009
WO WO 2009/139891 11/2009
WO WO 2010/128158 11/2010
WO WO 2013/116781 8/2013
WO WO 2014/055869 4/2014

OTHER PUBLICATIONS

[No. Author Listed], 2013 ASCO Annual Meeting. Phase II study of dalantercept, a novel inhibior of ALK1-mediated angiogenesis, in patients with recurrent or metastic squamous cell carinoma of the head and neck. Journal of Clinical Oncology. 2013. Suppl; Abstract TPS6098.

[No. Author Listed], Polyclonal Antibody Production Protocol—Rabbits. Florida State University. Revised Apr. 2007. 8 pages.

Bendell et al., Safety, pharmacokinetics, pharmacodynamics, and antitumor activity of dalantercept, an activin receptor-like kinase-1 ligand trap, in patients with advanced cancer. Clin Cancer Res. Jan. 15, 2014;20(2):480-9. Epub Oct. 30, 2013.

Benson et al., The clinical impact of HPV tumor status upon head and neck squamous cell carcinomas. Oral Oncol. Jun. 2014;50(6):565-74. Epub Oct. 14, 2013.

Forastiere, Overview of platinum chemotherapy in head and neck cancer. Semin Oncol. Oct. 1994;21(5 Suppl 12):20-7.

Hoffmann et al., Perspectives in the biological function, the technical and therapeutic application of bone morphogenetic proteins. Appl Microbiol Biotechnol. Oct. 2001;57(3):294-308.

Scott, Etanercept in arthritis. Int J Clin Pract. Jan. 2005;59(1):114-8.

Townson et al. Specificity and structure of a high affinity activin receptor-like kinase 1 (ALK1) signaling complex. J Biol Chem. Aug. 10, 2012;287(33):27313-25. Epub Jun. 20, 2012.

Wang et al., Broad targeting of angiogenesis for cancer prevention and therapy. Semin Cancer Biol. Jan. 16, 2015.

[No Author Listed] Celltransmissions. Newsletter for Cell Signaling and Neuroscience Research. Mar. 2003;19(1):12.

[No Author Listed] New Products From R&D Systems: Recombinant proteins, TGFbeta superfamily ligand antagonists. De Novo Catalogue. Mar. 2001. 2 pages.

[No Author Listed] Recombinant human ALK-1/Fc Chimera. Catalog number: 770-MA. R&D Systems, Inc. Dated May 8, 2007.

[No Author Listed] Recombinant human ALK-1/Fc Chimera. Catalog number: 370-AL-100. R&D Systems, Inc. Dated Feb. 10, 2012. 2 pages.

[No Author Listed] Recombinant human ALK-1/Fc Chimera. Catalognumber: 370-AL. R7D Systems, Inc. Dated Apr. 25, 2007. http://www.rndsystems.com/pdf/370-al.pdf. Retrieved online Aug. 6, 2008.

[No Author Listed] Score Search results. Accession No. AFO06596. Accessed Apr. 7, 2009.

[No Author Listed] Sigma® Product Information Sheet. Activin Receptor-Like Kinase 1 (ALK-1)/Fc Chimera. Product No. A 0476.

[No Author Listed] Flurokine™ E enzyme activity assays. R&D Systems De Novo Catalogue. Mar. 2001:1-2.

Genbank Accession No. EAW58212, Version EAW58212.1; Venter et al.; Dec. 18, 2006. 2 pages.

Abdalla et al., Hereditary haemorrhagic telangiectasia: current views on genetics and mechanisms of disease. J Med Genet. Feb. 2006;43(2):97-110. Epub May 6, 2005 Review.

Ashkenazi et al., Protection against endotoxic shock by a tumor necrosis factor receptor immunoadhesin. Proc Natl Acad Sci U S A. Dec. 1, 1991;88(23):10535-9.

Assis et al., Three novel mutations in the activin receptor-like kinase 1 (ALK-1) gene in hereditary hemorrhagic telangiectasia type 2 in Brazilian patients. J Hum Genet. 2007;52(3):237-43. Epub Jan. 12, 2007.

Attisano et al., Identification of human activin and TGF beta type I receptors that form heteromeric kinase complexes with type II receptors. Cell. Nov. 19, 1993;75(4):671-80.

Baka et al., A review of the latest clinical compounds to inhibit VEGF in pathological angiogenesis. Expert Opin Ther Targets. Dec. 2006;10(6):867-76. Review.

Bertolino et al., Transforming growth factor-beta signal transduction in angiogenesis and vascular disorders. Chest. Dec. 2005;128(6 Suppl):585S-590S.

Brown et al., Crystal structure of BMP-9 and functional interactions with pro-region and receptors. J Biol Chem. Jul. 1, 2005;280(26):25111-8. Epub Apr. 25, 2005.

Burgess et al., Possible dissociation of the heparin-binding and mitogenic activities of heparin-binding (acidic fibroblast) growth factor-1 from its receptor-binding activities by site-directed mutagenesis of a single lysine residue. J Cell Biol. Nov. 1990;111(5 Pt 1):2129-38.

Carvalho et al., Defective paracrine signalling by TGFbeta in yolk sac vasculature of endoglin mutant mice: a paradigm for hereditary haemorrhagic telangiectasia. Development. Dec. 2004;131(24):6237-47. Epub Nov. 17, 2004.

Chantrain et al., Mechanisms of pericyte recruitment in tumour angiogenesis: a new role for metalloproteinases. Eur J Cancer. Feb. 2006;42(3):310-8. Epub Jan. 10, 2006.

Cunha et al., Genetic and pharmacological targeting of activin receptor-like kinase 1 impairs tumor growth and angiogenesis. J Exp Med. Jan. 18, 2010;207(1):85-100, S1-5. Epub Jan. 11, 2010.

David et al., Bone morphogenetic protein-9 is a circulating vascular quiescence factor. Circ Res. Apr. 25, 2008;102(8):914-22. Epub Feb. 28, 2008.

David et al., Identification of BMP9 and BMP10 as functional activators of the orphan activin receptor-like kinase 1 (ALK1) in endothelial cells. Blood. Mar. 1, 2007;109(5):1953-61. Epub Oct. 26, 2006.

Ding et al., Significance of Id-1 up-regulation and its association with EGFR in bladder cancer cell invasion. Int J Oncol. Apr. 2006;28(4):847-54.

Fernandez-L et al., Gene expression fingerprinting for human hereditary hemorrhagic telangiectasia. Hum Mol Genet. Jul. 1, 2007;16(13):1515-33. Epub Apr. 9, 2007. Erratum in: Hum Mol Genet. Nov. 1, 2007;16(21):2649. Fernandez-Lopez, Africa [corrected to Fernandez-L, Africa].

(56) References Cited

OTHER PUBLICATIONS

Gerlach-Bank et al., DAN directs endolymphatic sac and duct outgrowth in the avian inner ear. Dev Dyn. Feb. 2004;229(2):219-30.
Godeny et al., Ang II-induced cell proliferation is dually mediated by c-Src/Yes/Fyn-regulated ERK1/2 activation in the cytoplasm and PKCzeta-controlled ERK1/2 activity within the nucleus. Am J Physiol Cell Physiol. Dec. 2006;291(6):C1297-307. Epub May 24, 2006.
Goumans et al., Activin receptor-like kinase (ALK)1 is an antagonistic mediator of lateral TGFbeta/ALK5 signaling. Mol Cell. Oct. 2003;12(4):817-28.
Goumans et al., Balancing the activation state of the endothelium via two distinct TGF-beta type I receptors. EMBO J. Apr. 2, 2002;21(7):1743-53.
Gupta et al., ID genes mediate tumor reinitiation during breast cancer lung metastasis. Proc Natl Acad Sci U S A. Dec. 4, 2007;104(49):19506-11. Epub Nov. 28, 2007.
Hofte et al., Fusion proteins with both insecticidal and neomycin phosphotransferase II activity. FEBS Lett. Jan. 4, 1998; 226(2):364-70. Epub Oct. 19, 2001.
Johnson et al., Mutations in the activin receptor-like kinase 1 gene in hereditary haemorrhagic telangiectasia type 2. Nat Genet. Jun. 1996;13(2):189-95.
Kamalian et al., Increased expression of Id family proteins in small cell lung cancer and its prognostic significance. Clin Cancer Res. Apr. 15, 2008;14(8):2318-25.
King, Applications and Engineering of Monoclonal Antibodies. Chapter 2: Antibody Engineering: Design for Specific Applications. CRC Press. 1998;:27-75.
Koleva et al., Endoglin structure and function: Determinants of endoglin phosphorylation by transforming growth factor-beta receptors. J Biol Chem. Sep. 1, 2006;281(35):25110-23. Epub Jun. 19, 2006.
Lamouille et al., Activin receptor-like kinase 1 is implicated in the maturation phase of angiogenesis. Blood. Dec. 15, 2002;100(13):4495-501.
Lebrin Endoglin promotes endothelial cell proliferation and TGF-beta/ALK1 signal transduction. EMBO J. Oct. 13, 2004;23(20):4018-28. Epub Sep. 23, 2004.
Lin et al., Structure-function relationships in glucagon: properties of highly purified des-His-1-, monoiodo-, and (des-Asn-28, Thr-29)(homoserine lactone-27)-glucagon. Biochemistry. Apr. 22, 1975;14(8):1559-63.
Ling et al., Overexpression of Id-1 in prostate cancer cells promotes angiogenesis through the activation of vascular endothelial growth factor (VEGF). Carcinogenesis. Oct. 2005;26(10):1668-76. Epub May 19, 2005.
Lopez-Coviella et al., Developmental pattern of expression of BMP receptors and Smads and activation of Smad1 and Smad5 by BMP9 in mouse basal forebrain. Brain Res. May 9, 2006;1088(1):49-56. Epub Apr. 13, 2006.
Mathews et al., Ch. 6: The three-dimensional structure of proteins. In Biochemistry, Second Edition. Benjamin/Cummings Publishing Co., Inc. 1996:165-171.
Mitchell et al., ALK1-Fc Inhibits Multiple Mediators of Angiogenesis and Suppresses Tumor Growth. Mol Cancer Ther. 2010;9(2): 379-88.
Ngo et al., Computational complexity, protein structure prediction, and the Levinthal Paradox. The Protein Folding Problem and Tertiary Structure Prediction. Merz et al., eds. Birkhauser Boston 1994. Excerpt from Chapter 14, pp. 492-495.
Oh et al., Activin receptor-like kinase 1 modulates transforming growth factor-beta 1 signaling in the regulation of angiogenesis. Proc Natl Acad Sci U S A. Mar. 14, 2000;97(6):2626-31.
Ota et al., Targets of transcriptional regulation by two distinct type I receptors for transforming growth factor-beta in human umbilical vein endothelial cells. J Cell Physiol. Dec. 2002;193(3):299-318.
Park et al., ALK5- and TGFBR2-independent role of ALK1 in the pathogenesis of hereditary hemorrhagic telangiectasia type 2. Blood. Jan. 15, 2008;111(2):633-42. Epub Oct. 2, 2007.
Roelen et al., Expression of Alk-1, a type 1 serine/threonine kinase receptor, coincides with sites of vasculogenesis and angiogenesis in early mouse development. Dev Dyn. Aug. 1997;209(4):418-30.
Rudnick et al., Affinity and avidity in antibody-based tumor targeting. Cancer Biother Radiopharm. Apr. 2009;24(2):155-61.
Scharpfenecker et al., BMP-9 signals via ALK1 and inhibits bFGF-induced endothelial cell proliferation and VEGF-stimulated angiogenesis. J Cell Sci. Mar. 15, 2007;120(Pt 6):964-72. Epub Feb. 20, 2007.
Scharpfenecker et al., Ionizing radiation shifts the PAI-1/ID-1 balance and activates notch signaling in endothelial cells. Int J Radiat Oncol Biol Phys. Feb. 1, 2009;73(2):506-13.
Seki et al., Arterial endothelium-specific activin receptor-like kinase 1 expression suggests its role in arterialization and vascular remodeling. Circ Res. Oct. 3, 2003;93(7):682-9. Epub Sep. 11, 2003.
Shovlin et al., Diagnostic criteria for hereditary hemorrhagic telangiectasia (Rendu-Osler-Weber syndrome). Am J Med Genet. Mar. 6, 2000;91(1):66-7.
Sordillo et al., RANK-Fc: a therapeutic antagonist for RANK-L in myeloma. Cancer. Feb. 1, 2003;97(3 Suppl):802-12.
Srinivasan et al., A mouse model for hereditary hemorrhagic telangiectasia (HHT) type 2. Hum Mol Genet. Mar. 1, 2003;12(5):473-82.
Stepanov et al., Molekulyarnaya biologiya. Struktura I funktsii belkov, M.: Nauka, 2005, pp. 61-62. [Chapter 4: Primary structure of protein. 4.1 Primary structure as a level of the protein organization.].
Ten Dijke et al., Activin receptor-like kinases: a novel subclass of cell-surface receptors with predicted serine/threonine kinase activity. Oncogene. Oct. 1993;8(10):2879-87.
Tokuriki et al., Stability effects of mutations and protein evolvability. Curr Opin Struct Biol. Oct. 2009;19(5):596-604. doi:10.1016/j.sbi.2009.08.003. Epub Sep. 16, 2009.
Torsney et al., Mouse model for hereditary hemorrhagic telangiectasia has a generalized vascular abnormality Circulation. Apr. 1, 2003;107(12):1653-7. Epub Mar. 17, 2003.
Ungefroren et al., Antitumor activity of ALK1 in pancreatic carcinoma cells. Int J Cancer. Apr. 15, 2007;120(8):1641-51.
Urness et al., Arteriovenous malformations in mice lacking activin receptor-like kinase-1. Nat Genet. Nov. 2000;26(3):328-31.
Valdimarsdottir et al., Stimulation of Id1 expression by bone morphogenetic protein is sufficient and necessary for bone morphogenetic protein-induced activation of endothelial cells. Circulation. Oct. 22, 2002;106(17):2263-70.
Valsecchi et al., Recent Treatment Advances and Novel Therapies in Pancreas Cancer: A Review. J Gastrointest Cancer. Dec. 17, 2013. [Epub ahead of print, pp. 1-12.].
Volpert et al., Id1 regulates angiogenesis through transcriptional repression of thrombospondin-1. Cancer Cell Dec. 2002;2(6):473-83.
Wells, Additivity of mutational effects in proteins. Biochemistry. Sep. 18, 1990;29(37):8509-17.
Wu et al., Cloning and characterization of the murine activin receptor like kinase-1 (ALK-1) homolog. Biochem Biophys Res Commun. Nov. 2, 1995;216(1):78-83.
Yu et al., Inhibitor of DNA binding-1 overexpression in prostate cancer: relevance to tumor differentiation. Pathol Oncol Res. Mar. 2009;15(1):91-6. Epub Aug. 28, 2008.
Zhao et al., Overexpression of Id-1 protein is a marker in colorectal cancer progression. Oncol Rep. Feb. 2008;19(2):419-24.
Samet, Does Idiopathic Pulmonary Fibrosis Increase Lung Cancer Risk? Amer J Respir Crit Care Med. 2000;161(1):1-2. doi: 10.1164/ajrccm.161.1.ed14-99.
Sharma et al., Poster Discussion 465. A Phase 1 dose escalating study of ACE-041, a novel inhibitor of ALK-1 mediated angiogenesis, in patients with advanced solid tumors. Euro J Cancer. Supplement. Nov. 19, 2010;8(7):149-5.

* cited by examiner

Figure 1: Amino acid sequence for Human Activin receptor-like kinase 1 (ALK-1) (gi:3915750; SEQ ID NO:1)

```
  1 MTLGSPRKGL LMLLMALVTQ GDPVKPSRGP LVTCTCESPH CKGPTCRGAW CTVVLVREEG
 61 RHPQEHRGCG NLHRELCRGR PTEFVNHYCC DSHLCNHNVS LVLEATQPPS EQPGTDGQLA
121 LILGPVLALL ALVALGVLGL WHVRRRQEKQ RGLHSELGES SLILKASEQG DSMLGDLLDS
181 DCTTGSGSGL PFLVQRTVAR QVALVECVGK GRYGEVWRGL WHGESVAVKI FSSRDEQSWF
241 RETEIYNTVL LRHDNILGFI ASDMTSRNSS TQLWLITHYH EHGSLYDFLQ RQTLEPHLAL
301 RLAVSAACGL AHLHVEIFGT QGKPAIAHRD FKSRNVLVKS NLQCCIADLG LAVMHSQGSD
361 YLDIGNNPRV GTKRYMAPEV LDEQIRTDCF ESYKWTDIWA FGLVLWEIAR RTIVNGIVED
421 YRPPFYDVVP NDPSFEDMKK VVCVDQQTPT IPNRLAADPV LSGLAQMMRE CWYPNPSARL
481 TALRIKKTLQ KISNSPEKPK VIQ
```

FIGURE 1

Figure 2: Nucleic acid sequence for Human Activin receptor-like kinase 1 (ALK-1) (SEQ ID NO:2)

```
   1 atgaccttgg gctcccccag gaaaggcctt ctgatgctgc tgatggcctt ggtgacccag
  61 ggagaccctg tgaagccgtc tcggggcccg ctggtgacct gcacgtgtga gagcccacat
 121 tgcaaggggc ctacctgccg gggggcctgg tgcacagtag tgctggtgcg ggaggagggg
 181 aggcaccccc aggaacatcg ggctgcgggg aacttgcaca gggagctctg caggggcgc
 241 cccaccgagt tcgtcaacca ctactgctgc gacagccacc tctgcaacca caacgtgtcc
 301 ctggtgctgg aggccaccca acctccttcg gagcagccgg gaacagatgg ccagctggcc
 361 ctgatcctgg gccccgtgct ggccttgctg gccctggtgg ccctgggtgt cctgggcctg
 421 tggcatgtcc gacggaggca ggagaagcag cgtggcctgc acagcgagct gggagagtcc
 481 agtctcatcc tgaaagcatc tgagcagggc gacagcatgt tgggggacct cctggacagt
 541 gactgcacca cagggagtgg ctcagggctc cccttcctgg tgcagaggac agtggcacgg
 601 caggttgcct tggtggagtg tgtgggaaaa ggccgctatg gcgaagtgtg gcggggcttg
 661 tggcacggtg agagtgtggc cgtcaagatc ttctcctcga gggatgaaca gtcctggttc
 721 cgggagactg agatctataa cacagtgttg ctcagacacg acaacatcct aggcttcatc
 781 gcctcagaca tgacctcccg caactcgagc acgcagctgt ggctcatcac gcactaccac
 841 gagcacggct ccctctacga ctttctgcag agacagacgc tggagcccca tctggctctg
 901 aggctagctg tgtccgcggc atgcggcctg gcgcacctgc acgtggagat cttcggtaca
 961 cagggcaaac cagccattgc ccaccgcgac ttcaagagcc gcaatgtgct ggtcaagagc
1021 aacctgcagt gttgcatcgc cgacctgggc ctggctgtga tgcactcaca gggcagcgat
1081 tacctggaca tcggcaacaa cccgagagtg ggcaccaagc ggtacatggc acccgaggtg
1141 ctggacgagc agatccgcac ggactgcttt gagtcctaca agtggactga catctgggcc
1201 tttggcctgg tgctgtggga gattgcccgc cggaccatcg tgaatggcat cgtggaggac
1261 tatagaccac ccttctatga tgtggtgccc aatgacccca gctttgagga catgaagaag
1321 gtggtgtgtg tggatcagca gacccccacc atccctaacc ggctggctgc agacccggtc
1381 ctctcaggcc tagctcagat gatgcgggag tgctggtacc caaacccctc tgcccgactc
1441 accgcgctgc ggatcaagaa gacactacaa aaaattagca acagtccaga gaagcctaaa
1501 gtgattcaat ag
```

FIGURE 2

Figure 3: An ALK1-Fc Fusion Protein (SEQ ID NO:3).

DPVKPSRGPLVTCTCESPHCKGPTCRGAWCTVVLVREEGRHPQEHRGCGNLHRE
LCRGRPTEFVNHYCCDSHLCNHNVSLVLEATQPPSEQPGTDGQLATGGGTHTCP
PCPAPELLGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPVPIEKTI
SKAKGQPREPQVYTLPPSREEMTKNQVSLTCLVKGFYPSDIAVEWESNGQPENN
YKTTPPVLDSDGSFFLYSKLTVDKSRWQQGNVFSCSVMHEALHNHYTQKSLSLS
PGK

FIGURE 3

Figure 4: Nucleic Acid Sequence Encoding an ALK1-Fc Expression Construct (Nucleic acid sequence, SEQ ID NO:4; Amino acid sequence, SEQ ID NO:5)

```
NheI        | - - - - - - - - - - - - -  CDS  - - - - - - - - - - - - - -
  |           M   D   A   M   K   R   G   L   C   C   V   L   L   L   C   G   A   V   F   V
     *     *     *  20     *     *     *  40     *     *     *  60     *     *
GCTAGCACCATGGATGCAATGAAGAGAGGGCTCTGCTGTGTGCTGCTGCTGTGTGGAGCAGTCTTCGTTT
    KasI
      |
 - - - - - - - - - - - - - - - -  CDS  - - - - - - - - - - - - - - - -
S   P   G   A   D   P   V   K   P   S   R   G   P   L   V   T   C   T   C   E   S   P   H   C
     *  80     *     *     * 100     *     *     * 120     *     *     * 140
CGCCCGGCGCCGACCCTGTGAAGCCGTCTCGGGGCCCGCTGGTGACCTGCACGTGTGAGAGCCCACATTG
 - - - - - - - - - - - - - - - -  CDS  - - - - - - - - - - - - - - - -
  K   G   P   T   C   R   G   A   W   C   T   V   V   L   V   R   E   E   G   R   H   P   Q
     *     *     * 160     *     *     * 180     *     *     * 200     *     *
CAAGGGGCCTACCTGCCGGGGGGCCTGGTGCACAGTAGTGCTGGTGCGGGAGGAGGGGAGGCACCCCCAG
 - - - - - - - - - - - - - - - -  CDS  - - - - - - - - - - - - - - - -
  E   H   R   G   C   G   N   L   H   R   E   L   C   R   G   R   P   T   E   F   V   N   H
     * 220     *     *     * 240     *     *     * 260     *     *     * 280
GAACATCGGGGCTGCGGGAACTTGCACAGGGAGCTCTGCAGGGGCCGCCCCACCGAGTTCGTCAACCACT
 - - - - - - - - - - - - - - - -  CDS  - - - - - - - - - - - - - - - -
Y   C   C   D   S   H   L   C   N   H   N   V   S   L   V   L   E   A   T   Q   P   P   S   E
     *     *     * 300     *     *     * 320     *     *     * 340     *     *
ACTCCTGCCACACCCACCTCTGCAACCACAACGTGTCCCTGGTGCTGCAGGCCACCCAACCTCCTTCGGA
                          AgeI
                            |
 - - - - - - - - - - - - - - - -  CDS  - - - - - - - - - - - - - - - -
  Q   P   G   T   D   G   Q   L   A   T   G   G   G   T   H   T   C   P   P   C   P   A   P
     * 360     *     *     * 380     *     *     * 400     *     *     * 420
GCAGCCGGGAACAGATGGCCAGCTGGCCACCGGTGGTGGAACTCACACATGCCCACCGTGCCCAGCACCT
 - - - - - - - - - - - - - - - -  CDS  - - - - - - - - - - - - - - - -
  E   A   L   G   A   P   S   V   F   L   F   P   P   K   P   K   D   T   L   M   I   S   R
     *     *     * 440     *     *     * 460     *     *     * 480     *     *
GAAGCCCTGGGGGCACCGTCAGTCTTCCTCTTCCCCCCAAAACCCAAGGACACCCTCATGATCTCCCGGA
 - - - - - - - - - - - - - - - -  CDS  - - - - - - - - - - - - - - - -
T   P   E   V   T   C   V   V   V   D   V   S   H   E   D   P   E   V   K   F   N   W   Y   V
     * 500     *     *     * 520     *     *     * 540     *     *     * 560
CCCCTGAGGTCACATGCGTGGTGGTGGACGTGAGCCACGAAGACCCTGAGGTCAAGTTCAACTGGTACGT
 - - - - - - - - - - - - - - - -  CDS  - - - - - - - - - - - - - - - -
  D   G   V   E   V   H   N   A   K   T   K   P   R   E   E   Q   Y   N   S   T   Y   R   V
     *     *     * 580     *     *     * 600     *     *     * 620     *     *
GGACGGCGTGGAGGTGCATAATGCCAAGACAAAGCCGCGGGAGGAGCAGTACAACAGCACGTACCGTGTG
 - - - - - - - - - - - - - - - -  CDS  - - - - - - - - - - - - - - - -
  V   S   V   L   T   V   L   H   Q   D   W   L   N   G   K   E   Y   K   C   K   V   S   N
     * 640     *     *     * 660     *     *     * 680     *     *     * 700
GTCAGCGTCCTCACCGTCCTGCACCAGGACTGGCTGAATGGCAAGGAGTACAAGTGCAAGGTCTCCAACA
 - - - - - - - - - - - - - - - -  CDS  - - - - - - - - - - - - - - - -
K   A   L   P   V   P   I   E   K   T   I   S   K   A   K   G   Q   P   R   E   P   Q   V   Y
     *     *     * 720     *     *     * 740     *     *     * 760     *     *
AAGCCCTCCCAGTCCCCATCGAGAAAACCATCTCCAAAGCCAAAGGGCAGCCCCGAGAACCACAGGTGTA
 - - - - - - - - - - - - - - - -  CDS  - - - - - - - - - - - - - - - -
  T   L   P   P   S   R   E   E   M   T   K   N   Q   V   S   L   T   C   L   V   K   G   F
     * 780     *     *     * 800     *     *     * 820     *     *     * 840
CACCCTGCCCCCATCCCGGGAGGAGATGACCAAGAACCAGGTCAGCCTGACCTGCCTGGTCAAAGGCTTC
 - - - - - - - - - - - - - - - -  CDS  - - - - - - - - - - - - - - - -
  Y   P   S   D   I   A   V   E   W   E   S   N   G   Q   P   E   N   N   Y   K   T   T   P
     *     *     * 860     *     *     * 880     *     *     * 900     *     *
TATCCCAGCGACATCGCCGTGGAGTGGGAGAGCAATGGGCAGCCGGAGAACAACTACAAGACCACGCCTC
 - - - - - - - - - - - - - - - -  CDS  - - - - - - - - - - - - - - - -
P   V   L   D   S   D   G   P   F   F   L   Y   S   K   L   T   V   D   K   S   R   W   Q   Q
     * 920     *     *     * 940     *     *     * 960     *     *     * 980
CCGTGCTGGACTCCGACGGCCCCTTCTTCCTCTACAGCAAGCTCACCGTGGACAAGAGCAGGTGGCAGCA
 - - - - - - - - - - - - - - - -  CDS  - - - - - - - - - - - - - - - -
  G   N   V   F   S   C   S   V   M   H   E   A   L   H   N   H   Y   T   Q   K   S   L   S
     *     *     *1000     *     *     *1020     *     *     *1040     *     *
GGGGAACGTCTTCTCATGCTCCGTGATGCATGAGGCTCTGCACAACCACTACACGCAGAAGAGCCTCTCC
                 EcoRI
                   |
 - - -  CDS  - - |
  L   S   P   G   K   *
     *1060     *     *     *
CTGTCTCCGGGTAAATGAGGAATTC
```

FIGURE 4

ALK1-Fc Fusion Protein from R&D Systems
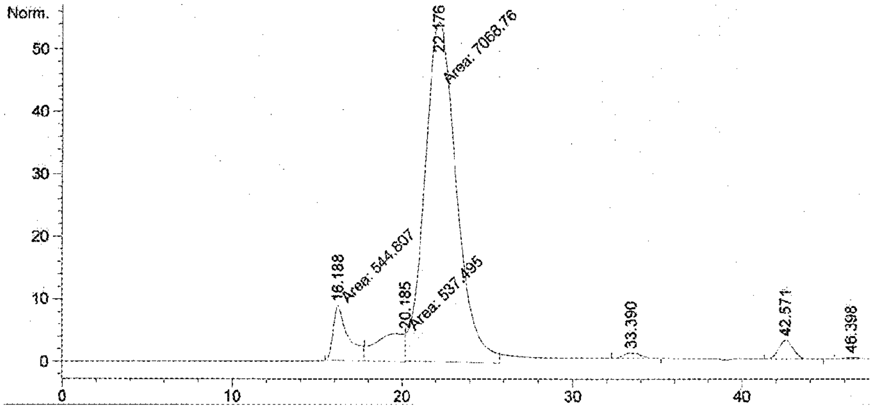
ALK1-Fc Fusion Protein Prepared by Applicants
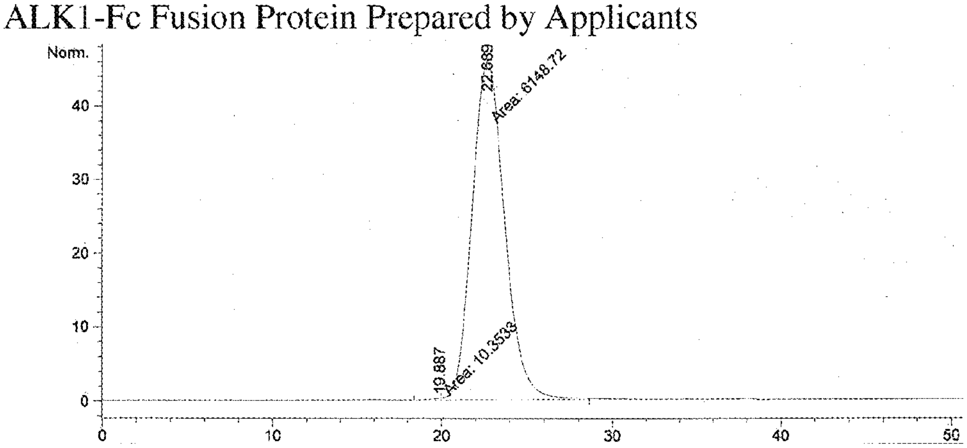
FIGURE 11

```
bmp9      RSAGAGSHCQK TSLRVNFEDI GWDSWIIAPK EYEAYECKGG CFFPLADDVT PTKHAIVQTL 60
bmp10     --NAKGNYCKR TPLYIDFKEI GWDSWIIAPP GYEAYECRGV CNYPLAEHLT PTKHAIIQAL 59
            . *.:*:: *.* ::*::* *********  *******:*  * :***:.:* ******:*:*

bmp9      VHLKFPTKVG KACCVPTKLS PISVLYKDDM GVPTLKYHYE GMSVAECGCR 110
bmp10     VHLKNSQKAS KACCVPTKLE PISILYLD-K GVVTYKFKYE GMAVSECGCR 108
          ****  . *.. *********. ***:** *    ** * *::** **:*:*****
```

FIGURE 19

SEQUENCE LISTING

```
<160> NUMBER OF SEQ ID NOS: 13

<210> SEQ ID NO 1
<211> LENGTH: 503
<212> TYPE: PRT
<213> ORGANISM: Homo sapiens

<400> SEQUENCE: 1
```

-continued

```
Met Thr Leu Gly Ser Pro Arg Lys Gly Leu Leu Met Leu Leu Met Ala
1               5                   10                  15

Leu Val Thr Gln Gly Asp Pro Val Lys Pro Ser Arg Gly Pro Leu Val
            20                  25                  30

Thr Cys Thr Cys Glu Ser Pro His Cys Lys Gly Pro Thr Cys Arg Gly
        35                  40                  45

Ala Trp Cys Thr Val Val Leu Val Arg Glu Glu Gly Arg His Pro Gln
    50                  55                  60

Glu His Arg Gly Cys Gly Asn Leu His Arg Glu Leu Cys Arg Gly Arg
65                  70                  75                  80

Pro Thr Glu Phe Val Asn His Tyr Cys Cys Asp Ser His Leu Cys Asn
                85                  90                  95

His Asn Val Ser Leu Val Leu Glu Ala Thr Gln Pro Pro Ser Glu Gln
            100                 105                 110

Pro Gly Thr Asp Gly Gln Leu Ala Leu Ile Leu Gly Pro Val Leu Ala
        115                 120                 125

Leu Leu Ala Leu Val Ala Leu Gly Val Leu Gly Leu Trp His Val Arg
    130                 135                 140

Arg Arg Gln Glu Lys Gln Arg Gly Leu His Ser Glu Leu Gly Glu Ser
145                 150                 155                 160

Ser Leu Ile Leu Lys Ala Ser Glu Gln Gly Asp Ser Met Leu Gly Asp
                165                 170                 175

Leu Leu Asp Ser Asp Cys Thr Thr Gly Ser Gly Ser Gly Leu Pro Phe
            180                 185                 190

Leu Val Gln Arg Thr Val Ala Arg Gln Val Ala Leu Val Glu Cys Val
        195                 200                 205

Gly Lys Gly Arg Tyr Gly Glu Val Trp Arg Gly Leu Trp His Gly Glu
    210                 215                 220

Ser Val Ala Val Lys Ile Phe Ser Ser Arg Asp Glu Gln Ser Trp Phe
225                 230                 235                 240

Arg Glu Thr Glu Ile Tyr Asn Thr Val Leu Leu Arg His Asp Asn Ile
                245                 250                 255

Leu Gly Phe Ile Ala Ser Asp Met Thr Ser Arg Asn Ser Ser Thr Gln
            260                 265                 270

Leu Trp Leu Ile Thr His Tyr His Glu His Gly Ser Leu Tyr Asp Phe
        275                 280                 285

Leu Gln Arg Gln Thr Leu Glu Pro His Leu Ala Leu Arg Leu Ala Val
    290                 295                 300

Ser Ala Ala Cys Gly Leu Ala His Leu His Val Glu Ile Phe Gly Thr
305                 310                 315                 320

Gln Gly Lys Pro Ala Ile Ala His Arg Asp Phe Lys Ser Arg Asn Val
                325                 330                 335

Leu Val Lys Ser Asn Leu Gln Cys Cys Ile Ala Asp Leu Gly Leu Ala
            340                 345                 350

Val Met His Ser Gln Gly Ser Asp Tyr Leu Asp Ile Gly Asn Asn Pro
        355                 360                 365

Arg Val Gly Thr Lys Arg Tyr Met Ala Pro Glu Val Leu Asp Glu Gln
    370                 375                 380

Ile Arg Thr Asp Cys Phe Glu Ser Tyr Lys Trp Thr Asp Ile Trp Ala
385                 390                 395                 400

Phe Gly Leu Val Leu Trp Glu Ile Ala Arg Arg Thr Ile Val Asn Gly
                405                 410                 415
```

```
Ile Val Glu Asp Tyr Arg Pro Pro Phe Tyr Asp Val Val Pro Asn Asp
            420                 425                 430

Pro Ser Phe Glu Asp Met Lys Lys Val Val Cys Val Asp Gln Gln Thr
        435                 440                 445

Pro Thr Ile Pro Asn Arg Leu Ala Ala Asp Pro Val Leu Ser Gly Leu
    450                 455                 460

Ala Gln Met Met Arg Glu Cys Trp Tyr Pro Asn Pro Ser Ala Arg Leu
465                 470                 475                 480

Thr Ala Leu Arg Ile Lys Lys Thr Leu Gln Lys Ile Ser Asn Ser Pro
                485                 490                 495

Glu Lys Pro Lys Val Ile Gln
            500


<210> SEQ ID NO 2
<211> LENGTH: 1512
<212> TYPE: DNA
<213> ORGANISM: Homo sapiens

<400> SEQUENCE: 2

atgaccttgg gctcccccag gaaaggcctt ctgatgctgc tgatggcctt ggtgacccag     60

ggagaccctg tgaagccgtc tcggggcccg ctggtgacct gcacgtgtga gagcccacat    120

tgcaaggggc ctacctgccg gggggcctgg tgcacagtag tgctggtgcg ggaggagggg    180

aggcaccccc aggaacatcg ggcgctgcgg aacttgcaca gggagctctg caggggggcgc    240

cccaccgagt tcgtcaacca ctactgctgc gacagccacc tctgcaacca caacgtgtcc    300

ctggtgctgg aggccaccca acctccttcg gagcagccgg gaacagatgg ccagctggcc    360

ctgatcctgg gccccgtgct ggccttgctg gccctggtgg ccctgggtgt cctgggcctg    420

tggcatgtcc gacggaggca ggagaagcag cgtggcctgc acagcgagct gggagagtcc    480

agtctcatcc tgaaagcatc tgagcagggc gacagcatgt tgggggacct cctggacagt    540

gactgcacca cagggagtgg ctcagggctc cccttcctgg tgcagaggac agtggcacgg    600

caggttgcct tggtggagtg tgtgggaaaa ggccgctatg gcgaagtgtg gcggggcttg    660

tggcacggtg agagtgtggc cgtcaagatc ttctcctcga gggatgaaca gtcctggttc    720

cgggagactg agatctataa cacagtgttg ctcagacacg acaacatcct aggcttcatc    780

gcctcagaca tgacctcccg caactcgagc acgcagctgt ggctcatcac gcactaccac    840

gagcacggct ccctctacga ctttctgcag agacagacgc tggagcccca tctggctctg    900

aggctagctg tgtccgcggc atgcggcctg gcgcacctgc acgtggagat cttcggtaca    960

cagggcaaac cagccattgc ccaccgcgac ttcaagagcc gcaatgtgct ggtcaagagc   1020

aacctgcagt gttgcatcgc cgacctgggc ctggctgtga tgcactcaca gggcagcgat   1080

tacctggaca tcggcaacaa cccgagagtg ggcaccaagc ggtacatggc acccgaggtg   1140

ctggacgagc agatccgcac ggactgcttt gagtcctaca agtggactga catctgggcc   1200

tttggcctgg tgctgtggga gattgcccgc cggaccatcg tgaatggcat cgtggaggac   1260

tatagaccac ccttctatga tgtggtgccc aatgacccca gctttgagga catgaagaag   1320

gtggtgtgtg tggatcagca gacccccacc atccctaacc ggctggctgc agacccggtc   1380

ctctcaggcc tagctcagat gatgcgggag tgctggtacc caaacccctc tgcccgactc   1440

accgcgctgc ggatcaagaa gacactacaa aaaattagca acagtccaga gaagcctaaa   1500

gtgattcaat ag                                                       1512
```

-continued

<210> SEQ ID NO 3
<211> LENGTH: 328
<212> TYPE: PRT
<213> ORGANISM: Artificial sequence
<220> FEATURE:
<223> OTHER INFORMATION: Recombinant protein

<400> SEQUENCE: 3

```
Asp Pro Val Lys Pro Ser Arg Gly Pro Leu Val Thr Cys Thr Cys Glu
1               5                   10                  15

Ser Pro His Cys Lys Gly Pro Thr Cys Arg Gly Ala Trp Cys Thr Val
            20                  25                  30

Val Leu Val Arg Glu Glu Gly Arg His Pro Gln Glu His Arg Gly Cys
        35                  40                  45

Gly Asn Leu His Arg Glu Leu Cys Arg Gly Arg Pro Thr Glu Phe Val
    50                  55                  60

Asn His Tyr Cys Cys Asp Ser His Leu Cys Asn His Asn Val Ser Leu
65                  70                  75                  80

Val Leu Glu Ala Thr Gln Pro Pro Ser Glu Gln Pro Gly Thr Asp Gly
                85                  90                  95

Gln Leu Ala Thr Gly Gly Gly Thr His Thr Cys Pro Pro Cys Pro Ala
            100                 105                 110

Pro Glu Leu Leu Gly Gly Pro Ser Val Phe Leu Phe Pro Pro Lys Pro
        115                 120                 125

Lys Asp Thr Leu Met Ile Ser Arg Thr Pro Glu Val Thr Cys Val Val
    130                 135                 140

Val Asp Val Ser His Glu Asp Pro Glu Val Lys Phe Asn Trp Tyr Val
145                 150                 155                 160

Asp Gly Val Glu Val His Asn Ala Lys Thr Lys Pro Arg Glu Glu Gln
                165                 170                 175

Tyr Asn Ser Thr Tyr Arg Val Val Ser Val Leu Thr Val Leu His Gln
            180                 185                 190

Asp Trp Leu Asn Gly Lys Glu Tyr Lys Cys Lys Val Ser Asn Lys Ala
        195                 200                 205

Leu Pro Val Pro Ile Glu Lys Thr Ile Ser Lys Ala Lys Gly Gln Pro
    210                 215                 220

Arg Glu Pro Gln Val Tyr Thr Leu Pro Pro Ser Arg Glu Glu Met Thr
225                 230                 235                 240

Lys Asn Gln Val Ser Leu Thr Cys Leu Val Lys Gly Phe Tyr Pro Ser
                245                 250                 255

Asp Ile Ala Val Glu Trp Glu Ser Asn Gly Gln Pro Glu Asn Asn Tyr
            260                 265                 270

Lys Thr Thr Pro Pro Val Leu Asp Ser Asp Gly Ser Phe Phe Leu Tyr
        275                 280                 285

Ser Lys Leu Thr Val Asp Lys Ser Arg Trp Gln Gln Gly Asn Val Phe
    290                 295                 300

Ser Cys Ser Val Met His Glu Ala Leu His Asn His Tyr Thr Gln Lys
305                 310                 315                 320

Ser Leu Ser Leu Ser Pro Gly Lys
                325
```

<210> SEQ ID NO 4
<211> LENGTH: 1075
<212> TYPE: DNA
<213> ORGANISM: Artificial sequence
<220> FEATURE:
<223> OTHER INFORMATION: Recombinant DNA

<400> SEQUENCE: 4

```
gctagcacca tggatgcaat gaagagaggg ctctgctgtg tgctgctgct gtgtggagca     60
gtcttcgttt cgcccggcgc cgaccctgtg aagccgtctc ggggcccgct ggtgacctgc    120
acgtgtgaga gcccacattg caaggggcct acctgccggg gggcctggtg cacagtagtg    180
ctggtgcggg aggaggggag gcacccccag gaacatcggg gctgcgggaa cttgcacagg    240
gagctctgca ggggccgccc caccgagttc gtcaaccact actgctgcga cagccacctc    300
tgcaaccaca acgtgtccct ggtgctggag gccacccaac ctccttcgga gcagccggga    360
acagatggcc agctggccac cggtggtgga actcacacat gcccaccgtg cccagcacct    420
gaagccctgg gggcaccgtc agtcttcctc ttccccccaa aacccaagga caccctcatg    480
atctcccgga cccctgaggt cacatgcgtg gtggtggacg tgagccacga agaccctgag    540
gtcaagttca actggtacgt ggacggcgtg gaggtgcata atgccaagac aaagccgcgg    600
gaggagcagt acaacagcac gtaccgtgtg gtcagcgtcc tcaccgtcct gcaccaggac    660
tggctgaatg gcaaggagta caagtgcaag gtctccaaca aagccctccc agtccccatc    720
gagaaaacca tctccaaagc caaagggcag ccccgagaac cacaggtgta caccctgccc    780
ccatcccggg aggagatgac caagaaccag gtcagcctga cctgcctggt caaaggcttc    840
tatcccagcg acatcgccgt ggagtgggag agcaatgggc agccggagaa caactacaag    900
accacgcctc ccgtgctgga ctccgacggc cccttcttcc tctacagcaa gctcaccgtg    960
gacaagagca ggtggcagca ggggaacgtc ttctcatgct ccgtgatgca tgaggctctg   1020
cacaaccact acacgcagaa gagcctctcc ctgtctccgg gtaaatgagg aattc        1075
```

<210> SEQ ID NO 5
<211> LENGTH: 352
<212> TYPE: PRT
<213> ORGANISM: Artificial sequence
<220> FEATURE:
<223> OTHER INFORMATION: Recombinant protein

<400> SEQUENCE: 5

```
Met Asp Ala Met Lys Arg Gly Leu Cys Cys Val Leu Leu Leu Cys Gly
1               5                   10                  15

Ala Val Phe Val Ser Pro Gly Ala Asp Pro Val Lys Pro Ser Arg Gly
            20                  25                  30

Pro Leu Val Thr Cys Thr Cys Glu Ser Pro His Cys Lys Gly Pro Thr
        35                  40                  45

Cys Arg Gly Ala Trp Cys Thr Val Val Leu Val Arg Glu Glu Gly Arg
    50                  55                  60

His Pro Gln Glu His Arg Gly Cys Gly Asn Leu His Arg Glu Leu Cys
65                  70                  75                  80

Arg Gly Arg Pro Thr Glu Phe Val Asn His Tyr Cys Cys Asp Ser His
                85                  90                  95

Leu Cys Asn His Asn Val Ser Leu Val Leu Glu Ala Thr Gln Pro Pro
            100                 105                 110

Ser Glu Gln Pro Gly Thr Asp Gly Gln Leu Ala Thr Gly Gly Gly Thr
        115                 120                 125

His Thr Cys Pro Pro Cys Pro Ala Pro Glu Ala Leu Gly Ala Pro Ser
    130                 135                 140

Val Phe Leu Phe Pro Pro Lys Pro Lys Asp Thr Leu Met Ile Ser Arg
145                 150                 155                 160
```

-continued

```
Thr Pro Glu Val Thr Cys Val Val Val Asp Val Ser His Glu Asp Pro
                165                 170                 175

Glu Val Lys Phe Asn Trp Tyr Val Asp Gly Val Glu Val His Asn Ala
            180                 185                 190

Lys Thr Lys Pro Arg Glu Glu Gln Tyr Asn Ser Thr Tyr Arg Val Val
        195                 200                 205

Ser Val Leu Thr Val Leu His Gln Asp Trp Leu Asn Gly Lys Glu Tyr
    210                 215                 220

Lys Cys Lys Val Ser Asn Lys Ala Leu Pro Val Pro Ile Glu Lys Thr
225                 230                 235                 240

Ile Ser Lys Ala Lys Gly Gln Pro Arg Glu Pro Gln Val Tyr Thr Leu
                245                 250                 255

Pro Pro Ser Arg Glu Glu Met Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Val Leu Asp
    290                 295                 300

Ser Asp Gly Pro Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
            340                 345                 350


<210> SEQ ID NO 6
<211> LENGTH: 225
<212> TYPE: PRT
<213> ORGANISM: Homo sapiens
<220> FEATURE:
<221> NAME/KEY: misc_feature
<222> LOCATION: (43)..(43)
<223> OTHER INFORMATION: Xaa can represent Asp or Ala
<220> FEATURE:
<221> NAME/KEY: misc_feature
<222> LOCATION: (100)..(100)
<223> OTHER INFORMATION: Xaa can represent Lys or Ala
<220> FEATURE:
<221> NAME/KEY: misc_feature
<222> LOCATION: (212)..(212)
<223> OTHER INFORMATION: Xaa can represent Asn or Ala

<400> SEQUENCE: 6

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Xaa Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Xaa Val Ser Asn Lys Ala Leu Pro Val Pro Ile Glu Lys
            100                 105                 110

Thr Ile Ser Lys Ala Lys Gly Gln Pro Arg Glu Pro Gln Val Tyr Thr
        115                 120                 125
```

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Pro Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Xaa His Tyr Thr Gln Lys Ser Leu Ser Leu Ser Pro Gly
    210                 215                 220

Lys
225

<210> SEQ ID NO 7
<211> LENGTH: 21
<212> TYPE: PRT
<213> ORGANISM: Artificial sequence
<220> FEATURE:
<223> OTHER INFORMATION: Recombinant leader peptide

<400> SEQUENCE: 7

Met Lys Phe Leu Val Asn Val Ala Leu Val Phe Met Val Val Tyr Ile
1               5                   10                  15

Ser Tyr Ile Tyr Ala
            20

<210> SEQ ID NO 8
<211> LENGTH: 22
<212> TYPE: PRT
<213> ORGANISM: Artificial sequence
<220> FEATURE:
<223> OTHER INFORMATION: Recombinant leader peptide

<400> SEQUENCE: 8

Met Asp Ala Met Lys Arg Gly Leu Cys Cys Val Leu Leu Leu Cys Gly
1               5                   10                  15

Ala Val Phe Val Ser Pro
            20

<210> SEQ ID NO 9
<211> LENGTH: 21
<212> TYPE: PRT
<213> ORGANISM: Artificial sequence
<220> FEATURE:
<223> OTHER INFORMATION: Recombinant leader peptide

<400> SEQUENCE: 9

Met Thr Leu Gly Ser Pro Arg Lys Gly Leu Leu Met Leu Leu Met Ala
1               5                   10                  15

Leu Val Thr Gln Gly
            20

<210> SEQ ID NO 10
<211> LENGTH: 180
<212> TYPE: PRT
<213> ORGANISM: Homo sapiens

<400> SEQUENCE: 10

Met Leu Arg Val Leu Val Gly Ala Val Leu Pro Ala Met Leu Leu Ala

-continued

```
1               5                   10                  15

Ala Pro Pro Pro Ile Asn Lys Leu Ala Leu Phe Pro Asp Lys Ser Ala
            20                  25                  30

Trp Cys Glu Ala Lys Asn Ile Thr Gln Ile Val Gly His Ser Gly Cys
        35                  40                  45

Glu Ala Lys Ser Ile Gln Asn Arg Ala Cys Leu Gly Gln Cys Phe Ser
    50                  55                  60

Tyr Ser Val Pro Asn Thr Phe Pro Gln Ser Thr Glu Ser Leu Val His
65                  70                  75                  80

Cys Asp Ser Cys Met Pro Ala Gln Ser Met Trp Glu Ile Val Thr Leu
                85                  90                  95

Glu Cys Pro Gly His Glu Glu Val Pro Arg Val Asp Lys Leu Val Glu
            100                 105                 110

Lys Ile Leu His Cys Ser Cys Gln Ala Cys Gly Lys Glu Pro Ser His
        115                 120                 125

Glu Gly Leu Ser Val Tyr Val Gln Gly Glu Asp Gly Pro Gly Ser Gln
    130                 135                 140

Pro Gly Thr His Pro His Pro His Pro His Pro His Pro Gly Gly Gln
145                 150                 155                 160

Thr Pro Glu Pro Glu Asp Pro Pro Gly Ala Pro His Thr Glu Glu Glu
                165                 170                 175

Gly Ala Glu Asp
            180
```

<210> SEQ ID NO 11
<211> LENGTH: 2003
<212> TYPE: DNA
<213> ORGANISM: Homo sapiens

<400> SEQUENCE: 11

```
gccgagcctc ctggggcgcc cgggcccgcg acccccgcac ccagctccgc aggaccggcg     60

ggcgcgcgcg ggctctggag gccacgggca tgatgcttcg ggtcctggtg gggggctgtcc   120

tccctgccat gctactggct gccccaccac ccatcaacaa gctggcactg ttcccagata    180

agagtgcctg gtgcgaagcc aagaacatca cccagatcgt gggccacagc ggctgtgagg    240

ccaagtccat ccagaacagg gcgtgcctag gacagtgctt cagctacagc gtccccaaca    300

ccttcccaca gtccacagag tccctggttc actgtgactc ctgcatgcca gcccagtcca    360

tgtgggagat tgtgacgctg gagtgcccgg gccacgagga ggtgcccagg gtggacaagc    420

tggtggagaa gatcctgcac tgtagctgcc aggcctgcgg caaggagcct agtcacgagg    480

ggctgagcgt ctatgtgcag ggcgaggacg ggccgggatc ccagcccggc acccaccctc    540

acccccatcc ccaccccat cctggcgggc agacccctga gcccgaggac ccccctgggg     600

ccccccacac agaggaagag ggggctgagg actgaggccc ccccaactct tcctcccctc    660

tcatccccct gtggaatgtt gggtctcact ctctggggaa gtcaggggag aagctgaagc    720

ccccctttgg cactggatgg acttggcttc agactcggac ttgaatgctg cccggttgcc    780

atggagatct gaaggggcgg ggttagagcc aagctgcaca atttaatata ttcaagagtg    840

gggggaggaa gcagaggtct tcagggctct ttttttgggg ggggggtggt ctcttcctgt    900

ctggcttcta gagatgtgcc tgtgggaggg ggaggaagtt ggctgagcca ttgagtgctg    960

ggggaggcca tccaagatgg catgaatcgg gctaaggtcc ctgggggtgc agatggtact   1020

gctgaggtcc cgggcttagt gtgagcatct tgccagcctc aggcttgagg gagggctggg   1080
```

-continued

```
ctagaaagac cactggcaga aacaggaggc tccggcccca caggtttccc caaggcctct   1140

caccccactt cccatctcca gggaagcgtc gccccagtgg cactgaagtg gccctccctc   1200

agcggagggg tttgggagtc aggcctgggc aggaccctgc tgactcgtgg cgcgggagct   1260

gggagccagg ctctccgggc ctttctctgg cttccttggc ttgcctggtg ggggaagggg   1320

aggaggggaa gaaggaaagg gaagagtctt ccaaggccag aaggaggggg acaacccccc   1380

aagaccatcc ctgaagacga gcatcccccct cctctccctg ttagaaatgt tagtgccccg   1440

cactgtgccc caagttctag gccccccaga aagctgtcag agccggccgc cttctcccct   1500

ctcccaggga tgctctttgt aaatatcgga tgggtgtggg agtgaggggt tacctccctc   1560

gccccaaggt tccagaggcc ctaggcggga tgggctcgct gaacctcgag gaactccagg   1620

acgaggagga catgggactt gcgtggacag tcagggttca cttgggctct ctctagctcc   1680

ccaattctgc ctgcctcctc cctcccagct gcactttaac cctagaaggt ggggacctgg   1740

ggggagggac agggcaggcg ggcccatgaa gaaagcccct cgttgcccag cactgtctgc   1800

gtctgctctt ctgtgcccag ggtggctgcc agcccactgc ctcctgcctg ggtggcctg    1860

gccctcctgg ctgttgcgac gcgggcttct ggagcttgtc accattggac agtctccctg   1920

atggaccctc agtcttctca tgaataaatt ccttcaacgc caaaaaaaaa aaaaaaaaaa   1980

aaaaaaaaaa aaaaaaaaaa aaa                                           2003
```

```
<210> SEQ ID NO 12
<211> LENGTH: 111
<212> TYPE: PRT
<213> ORGANISM: Artificial sequence
<220> FEATURE:
<223> OTHER INFORMATION: Recombinant protein

<400> SEQUENCE: 12

Arg Ser Ala Gly Ala Gly Ser His Cys Gln Lys Thr Ser Leu Arg Val
1               5                   10                  15

Asn Phe Glu Asp Ile Gly Trp Asp Ser Trp Ile Ile Ala Pro Lys Glu
            20                  25                  30

Tyr Glu Ala Tyr Glu Cys Lys Gly Gly Cys Phe Phe Pro Leu Ala Asp
        35                  40                  45

Asp Val Thr Pro Thr Lys His Ala Ile Val Gln Thr Leu Val His Leu
    50                  55                  60

Lys Phe Pro Thr Lys Val Gly Lys Ala Cys Cys Val Pro Thr Lys Leu
65                  70                  75                  80

Ser Pro Ile Ser Val Leu Tyr Lys Asp Asp Met Gly Val Pro Thr Leu
                85                  90                  95

Lys Tyr His Tyr Glu Gly Met Ser Val Ala Glu Cys Gly Cys Arg
            100                 105                 110


<210> SEQ ID NO 13
<211> LENGTH: 108
<212> TYPE: PRT
<213> ORGANISM: Artificial sequence
<220> FEATURE:
<223> OTHER INFORMATION: Recombinant protein

<400> SEQUENCE: 13

Asn Ala Lys Gly Asn Tyr Cys Lys Arg Thr Pro Leu Tyr Ile Asp Phe
1               5                   10                  15

Lys Glu Ile Gly Trp Asp Ser Trp Ile Ile Ala Pro Pro Gly Tyr Glu
            20                  25                  30
```

-continued

| | | | | | | | | | | | | | | | |
|---|---|---|---|---|---|---|---|---|---|---|---|---|---|---|---|
| Ala | Tyr | Glu | Cys | Arg | Gly | Val | Cys | Asn | Tyr | Pro | Leu | Ala | Glu | His | Leu |
| | | 35 | | | | | 40 | | | | | 45 | | | |
| Thr | Pro | Thr | Lys | His | Ala | Ile | Ile | Gln | Ala | Leu | Val | His | Leu | Lys | Asn |
| | 50 | | | | | 55 | | | | | 60 | | | | |
| Ser | Gln | Lys | Ala | Ser | Lys | Ala | Cys | Cys | Val | Pro | Thr | Lys | Leu | Glu | Pro |
| 65 | | | | | 70 | | | | | 75 | | | | | 80 |
| Ile | Ser | Ile | Leu | Tyr | Leu | Asp | Lys | Gly | Val | Val | Thr | Tyr | Lys | Phe | Lys |
| | | | | 85 | | | | | 90 | | | | | 95 | |
| Tyr | Glu | Gly | Met | Ala | Val | Ser | Glu | Cys | Gly | Cys | Arg | | | | |
| | | | 100 | | | | | 105 | | | | | | | |

ANTAGONISTS OF BMP9, BMP10, ALK1 AND OTHER ALK1 LIGANDS, AND USES THEREOF

RELATED APPLICATIONS

This application is a continuation of U.S. application Ser. No. 12/467,170, filed on May 15, 2009, which application claims the benefit under 35 U.S.C. §119(e) of U.S. provisional application Ser. No. 61/053,644, filed May 15, 2008, the entire contents of which are incorporated by reference herein. U.S. application Ser. No. 12/467,170 is also a continuation-in-part of U.S application Ser. No. 11/982,738, filed Nov. 2, 2007, which in turn claims the benefit under 35 U.S.C. §119(e) of U.S. provisional application Ser. No. 60/856,592, filed Nov. 2, 2006, the entire contents of which are incorporated herein by reference.

BACKGROUND

Angiogenesis, the process of forming new blood vessels, is critical in many normal and abnormal physiological states. Under normal physiological conditions, humans and animals undergo angiogenesis in specific and restricted situations. For example, angiogenesis is normally observed in wound healing, fetal and embryonic development and formation of the corpus luteum, endometrium and placenta.

Undesirable or inappropriately regulated angiogenesis occurs in many disorders, in which abnormal endothelial growth may cause or participate in the pathological process. For example, angiogenesis participates in the growth of many tumors. Deregulated angiogenesis has been implicated in pathological processes such as rheumatoid arthritis, retinopathies, hemangiomas, and psoriasis. The diverse pathological disease states in which unregulated angiogenesis is present have been categorized as angiogenesis-associated diseases.

Both controlled and uncontrolled angiogenesis are thought to proceed in a similar manner. Capillary blood vessels are composed primarily of endothelial cells and pericytes, surrounded by a basement membrane. Angiogenesis begins with the erosion of the basement membrane by enzymes released by endothelial cells and leukocytes. The endothelial cells, which line the lumen of blood vessels, then protrude through the basement membrane. Angiogenic factors induce the endothelial cells to migrate through the eroded basement membrane. The migrating cells form a "sprout" protruding from the parent blood vessel, where the endothelial cells undergo mitosis and proliferate. Endothelial sprouts merge with each other to form capillary loops, creating the new blood vessel.

Agents that inhibit angiogenesis have proven to be effective in treating a variety of disorders. Avastin™ (bevacizumab), a monoclonal antibody that binds to Vascular Endothelial Growth Factor (VEGF), has proven to be effective in the treatment of a variety of cancers. Macugen™, an aptamer that binds to VEGF has proven to be effective in the treatment of neovascular (wet) age-related macular degeneration. Antagonists of the SDF/CXCR4 signaling pathway inhibit tumor neovascularization and are effective against cancer in mouse models (Guleng et al. Cancer Res. 2005 Jul. 1; 65(13):5864-71). The isocoumarin 2-(8-hydroxy-6-methoxy-1-oxo-1H-2-benzopyran-3-yl)propionic acid (NM-3) has completed phase I clinical evaluation as an orally bioavailable angiogenesis inhibitor. NM-3 directly kills both endothelial and tumor cells in vitro and is effective in the treatment of diverse human tumor xenografts in mice (Agata et al. Cancer Chemother Pharmacol. 2005 December; 56(6): 610-4.). Thalidomide and related compounds have shown beneficial effects in the treatment of cancer, and although the molecular mechanism of action is not clear, the inhibition of angiogenesis appears to be an important component of the anti-tumor effect (see, e.g., Dredge et al. Microvasc Res. 2005 January; 69(1-2):56-63). The success of TNF-alpha antagonists in the treatment of rheumatoid arthritis is partially attributed to anti-angiogenic effects on the inflamed joint tissue (Feldmann et al. Annu Rev Immunol. 2001; 19:163-96). Anti-angiogenic therapies are widely expected to have beneficial effects on other inflammatory diseases, particularly psoriasis. Although many anti-angiogenic agents have an effect on angiogenesis regardless of the tissue that is affected, other angiogenic agents may tend to have a tissue-selective effect.

It is desirable to have additional compositions and methods for inhibiting angiogenesis. These include methods and compositions which can inhibit the unwanted growth of blood vessels, either generally or in certain tissues and/or disease states.

SUMMARY

In part, the present disclosure presents a characterization of an activin-like kinase I (ALK1)-mediated regulatory system, including its ligands BMP9 and BMP10, and the role of this system in angiogenesis. In certain aspects, the disclosure provides antagonists of ALK-1 ligands and the use of such antagonists as anti-angiogenic agents. Additionally, the disclosure provides antagonists of ALK-1 itself, and the use of such antagonists as anti-angiogenic agents. As described herein, ALK1 is a receptor for the GDF5 group of ligands, which includes GDF6 and GDF7, and also for the BMP9 group of ligands, which includes BMP10. This disclosure demonstrates that signaling mediated by ALK1 and the ligands described above is involved in angiogenesis in vivo, and that inhibition of this regulatory system has a potent anti-angiogenic effect. With respect to BMP9 and BMP10 in particular, these data are in contrast to the published literature, which identify BMP9 and BMP10 as potent anti-angiogenic agents that signal through ALK1. See, e.g., Scharpfenecker et al., *J Cell Sci.* 2007 Mar. 15; 120(Pt 6):964-72; David et al. *Blood* March 1; 109(5):1953-61; 2007; David et al., *Circ Res.* 2008 Apr. 25; 102(8):914-22. Thus, in certain aspects, the disclosure provides antagonists of the ALK1 regulatory system, including antagonists of the receptor or one or more of the ligands, for use in inhibiting angiogenesis. In certain aspects, the disclosure provides antagonists of ALK1 ligands for the treatment of cancers, particularly multiple myeloma, melanoma, lung cancer, rheumatoid arthritis, and disorders associated with pathological angiogenesis in the eye.

In certain aspects, the disclosure provides polypeptides comprising a ligand binding portion of the extracellular domain of ALK1 ("ALK1 ECD polypeptides") for use in inhibiting angiogenesis. While not wishing to be bound to any particular mechanism of action, it is expected that such polypeptides act by binding to ligands of ALK1 and inhibiting the ability of these ligands to interact with ALK1 as well as other receptors. In certain embodiments, an ALK1 ECD polypeptide comprises an amino acid sequence that is at least 70%, 80%, 90%, 95%, 96%, 97%, 98%, 99% or 100% identical to the sequence of amino acids 22-118 of the human ALK1 sequence of SEQ ID NO:1. An ALK1 ECD polypeptide may be used as a small monomeric protein or in a dimerized form (e.g., expressed as a fusion protein), particularly for local administration into tissues such as the eye. An ALK1 ECD may also be fused to a second polypeptide portion to provide improved properties, such as an increased half-life or greater ease of production or purification. Fusions to an Fc portion of an immunoglobulin or linkage to a polyoxyethylene moiety (e.g., polyethylene glycol) may be particularly useful to increase the serum half-life of the ALK1 ECD polypeptide in systemic administration (e.g., intravenous, intraarterial and intra-peritoneal administration). As demonstrated herein, a systemically administered ALK1-Fc polypeptide has a potent anti-angiogenic effect in the eye and also provides positive effects in murine models of rheumatoid arthritis and various tumors. In certain embodiments, an ALK1-Fc fusion protein comprises a polypeptide having an amino acid sequence that is at least 70%, 80%, 90%, 95%, 96%, 97%, 98%, 99% or 100% identical to the sequence of amino acids 22-118 of SEQ ID NO:1, which polypeptide is fused, either with or without an intervening linker, to an Fc portion of an immunoglobulin, and wherein the ALK1-Fc fusion protein binds to GDF5, GDF7, BMP9 and/or BMP10 with a $K_D$ of less than $1\times10^{-7}$ M and/or binds to TGFβ-1 with a $K_D$ of greater than $1\times10^{-6}$. An Fc portion may be selected so as to be appropriate to the organism. Optionally, the Fc portion is an Fc portion of a human IgG1. In a preferred embodiment, the ALK1-Fc fusion protein comprises amino acids 22-118 of SEQ ID NO:1. Optionally, the ALK1-Fc fusion protein comprises the amino acid sequence of SEQ ID NO: 3. Optionally, the ALK1-Fc fusion protein is the protein produced by expression of the nucleic acid of SEQ ID NO:4 in a mammalian cell line, particularly a Chinese Hamster Ovary (CHO) cell line. ALK1-ECD polypeptides may be formulated as a pharmaceutical preparation that is substantially pyrogen free. The pharmaceutical preparation may be prepared for systemic delivery (e.g., intravenous, intraarterial or subcutaneous delivery) or local delivery (e.g., to the eye).

In certain aspects, the disclosure identifies difficulties in developing relatively homogeneous preparations of ALK1-Fc fusion protein for use in a therapeutic setting. As described herein, the ALK1-Fc fusion protein tends to aggregate into higher order multimers. The disclosure provides solutions to these difficulties and therefore provides pharmaceutical preparations comprising ALK1-Fc fusion proteins wherein such preparations are at least 85%, 90%, 95%, 96%, 97%, 98% or 99% composed of dimeric ALK1-Fc fusion protein. Therefore, in certain aspects, the disclosure provides pharmaceutical preparations comprising an ALK1-Fc fusion protein comprising: a polypeptide having an amino acid sequence that is at least 97% identical to the sequence of amino acids 22-118 of SEQ ID NO:1, which polypeptide is fused to an Fc portion of an immunoglobulin, and wherein the ALK1-Fc fusion protein binds to GDF5, GDF7, BMP9 and/or BMP10 with a $K_D$ of less than $1\times10^{-7}$ M and/or binds to TGFβ-1 with a $K_D$ of greater than $1\times10^{-6}$ and wherein at least 85%, 90%, 95%, 96%, 97%, 98%, or 99% of the ALK1-Fc fusion protein is present in a dimeric form. The Fc portion of the ALK1-Fc fusion protein may be an Fc portion of a human IgG1. The ALK1-Fc fusion protein may comprise the amino acid sequence of SEQ ID NO: 3. The ALK1-Fc fusion protein may be produced by expression of the nucleic acid of SEQ ID NO:4 in a mammalian cell line, particularly a Chinese Hamster Ovary (CHO) cell line. Such pharmaceutical preparations may formulated so as to be appropriate for administration to the eye, particularly by injection. The disclosed pharmaceutical preparations may be used for a variety of therapeutic purposes described herein, including inhibiting angiogenesis, treating a tumors, treating rheumatoid arthritis, and treating ocular disorders associated with angiogenesis.

The ALK1-Fc pharmaceutical preparations and preparations comprising antibodies directed to ALK1 or one or more ligands of ALK1 (e.g., BMP9 and/or BMP10) may be used in conjunction with a second agent that inhibits angiogenesis, such as a VEGF antagonist (e.g., Avastin, sorafenib, and VEGF receptor traps).

In certain aspects, the disclosure provides methods for inhibiting angiogenesis in a mammal by administering any of the ALK1 ECD polypeptides described generally or specifically herein. In one embodiment, a method comprises administering to the mammal an effective amount of an ALK1-Fc fusion protein, wherein the ALK1 Fc fusion protein comprises a polypeptide having an amino acid sequence that is at least 90% identical to the sequence of amino acids 22-118 of SEQ ID NO:1, which polypeptide is fused to an Fc portion of an immunoglobulin, and wherein the ALK1-Fc fusion protein binds to TGFβ-1 with a $K_D$ of greater than $1\times10^{-6}$. Optionally, the ALK1-Fc fusion protein binds to one or more ALK1 ligands selected from the group consisting of: GDF5, GDF6, GDF7, BMP9 and BMP10. Optionally, the ALK1-Fc fusion protein has a sequence of SEQ ID NO:3. The ALK1 ECD polypeptide may be delivered locally (e.g., to the eye) or systemically (e.g., intravenously, intraarterially or subcutaneously). In a particular embodiment, the disclosure provides a method for inhibiting angiogenesis in the eye of a mammal by administering an ALK1-Fc protein to the mammal at a location distal to the eye, e.g. by systemic administration.

In certain aspects, the disclosure provides antibodies that bind to ALK1, particularly an epitope situated in the extracellular domain, amino acids 22-118 of SEQ ID NO:1, and inhibit the binding of ALK1 to at least one ALK1 ligand selected from the group consisting of: GDF5, GDF6, GDF7, BMP9 and BMP10. Based on the affinity of these ligands for ALK1, an antibody may bind with a $K_D$ of less than $5\times10^{-8}$ M, and optionally between $5\times10^{-8}$ and $1\times10^{-10}$. An antibody with affinity within this range would be expected to inhibit signaling by one or more of GDF5, GDF6, and GDF7 while having less effect on signaling by BMP9 and BMP10. Such an antibody preferably inhibits angiogenesis stimulated by at least one ALK1 ligand selected from the group consisting of: GDF5, GDF6, and GDF7. While not wishing to be bound to a particular mechanism, it is expected that such antibodies will act by inhibiting ALK1 activity directly, which should be contrasted to the activity of an ALK1-Fc fusion protein, which is expected to inhibit the activity of ALK1 ligands. An anti-ALK1 antibody is not expected to interfere with the ability of GDF5, GDF6, GDF7, BMP9 or BMP10 to signal through alternative receptor systems, such as the BMPR1a, BMPR1b and BMPRII complexes. However, an anti-ALK1 antibody is expected to interfere with the ability of low affinity ligands for ALK1 (e.g., TGF-β, which is generally recognized as triggering significant signaling events through ALK-1 even though binding is relatively weak) to signal through ALK1, even though an ALK1 ECD may not bind to or inhibit such low affinity ligands. An antibody may bind to the ALK1 polypeptide with a $K_D$ of less than $1\times10^{-10}$ M. An antibody with affinity within this range would be expected to inhibit signaling by BMP9 or BMP10. Such an antibody preferably inhibits binding of BMP9 and BMP10 to ALK1. Notably, based on the data disclosed herein, an antibody that binds relatively poorly to ALK1 may inhibit TGFβ binding to ALK1 while failing to inhibit the tighter binding ligands such as GDF5 or BMP9. The antibodies described herein are preferably recombinant antibodies, meaning an antibody expressed from a nucleic acid that has been constructed using the techniques of molecular biology, such as a humanized antibody or a fully human antibody developed from a single chain antibody. Fv, Fab and single chain antibodies are also included within the term "recombinant antibody". Antibodies may also be polyclonal or non-recombinant monoclonal antibodies (including human or murine forms, as well as human antibodies obtained from transgenic mice). Antibodies and ALK1-ECD polypeptides may be formulated as a pharmaceutical preparation that is substantially pyrogen free. The pharmaceutical preparation may be prepared for systemic delivery (e.g., intravenous, intraarterial or subcutaneous delivery) or local delivery (e.g., to the eye). Antibodies described in WO 2007/040912 may be useful in the various methods described herein.

In certain aspects, the disclosure provides methods for inhibiting angiogenesis in a mammal by administering to the mammal an effective amount of an antibody that binds to an ALK1 polypeptide, described herein either generally or specifically. An antibody useful for this purpose may bind to the extracellular domain of ALK1 (e.g., bind to a polypeptide consisting of amino acids 22-118 of SEQ ID NO:1) or another portion of ALK1. The antibody may bind to a polypeptide consisting of amino acids 22-118 of SEQ ID NO:1 and inhibits the binding of at least one ALK1 ligand selected from the group consisting of: GDF5, GDF6, GDF7, BMP9 and BMP10. The antibody may bind to the ALK1 polypeptide with a $K_D$ of less than $5\times10^{-8}$ M, and optionally between $5\times10^{-8}$ and $1\times10^{-10}$. The antibody may inhibit angiogenesis stimulated by at least one ALK1 ligand selected from the group consisting of: GDF5, GDF6 and GDF7. An antibody that selectively inhibits signaling mediated by GDF5, GDF6, or GDF7 relative to signaling by BMP9 or BMP10 may be used as a selective inhibitor of angiogenesis that occurs in tissues where GDF5, GDF6, or GDF7 are localized: primarily bone or joints. The antibody may bind to the ALK1 polypeptide with a $K_D$ of less than $1\times10^{-10}$ M. The antibody may inhibit the binding of ALK1 to an ALK1 ligand, wherein the ALK1 ligand is selected from the group consisting of: BMP9 and BMP10. The anti-ALK1 antibody may be delivered locally (e.g., to the eye) or systemically (e.g., intravenously, intraarterially or subcutaneously). In a particular embodiment, the disclosure provides a method for inhibiting angiogenesis in the eye of a mammal by administering an anti-ALK1 antibody. In another particular embodiment, the disclosure provides a method for treating patients with multiple myeloma. In a particular embodiment, the disclosure provides a method for inhibiting angiogenesis in disorders that are associated with pathological angiogenesis as a consequence of multiple pro-angiogenic factors, such as VEGF, PDGF and/or FGF.

In certain aspects, the disclosure provides antibodies that bind to an ALK1 ligand disclosed herein and inhibit the binding of the ALK1 ligand to ALK1. While not wishing to be bound to any particular mechanism, it is expected that antibodies that bind to ALK1 ligands will have effects that are similar in nature to ALK1 ECD polypeptides, because both types of agent bind to the ligands rather than the receptor itself. In certain embodiments, the antibody binds to a ligand selected from the group consisting of GDF5, GDF6 and GDF7. The antibody may bind to the ALK1 ligand with a $K_D$ of less than $5\times10^{-8}$ M. The antibody may be selected for inhibition of angiogenesis stimulated by the ALK1 ligand. A CAM assay is an appropriate assay system for selection of desirable antibodies. Such antibodies are preferably recombinant antibodies, and may be formulated as a pharmaceutical preparation that is substantially pyrogen free. The pharmaceutical preparation may be prepared for systemic delivery (e.g., intravenous, intraarterial or subcutaneous delivery) or local delivery (e.g., to the eye).

In certain aspects, the disclosure provides antibodies that bind to an ALK1 ligand and inhibit the binding of the ALK1 ligand to ALK1, wherein the ALK1 ligand is selected from the group consisting of BMP9 and BMP10. Notably, as shown herein, a neutralizing anti-BMP9 antibody inhibits angiogenesis in vivo. Additionally, as demonstrated herein, BMP-10 stimulates angiogenesis while an antagonist of BMP-10 inhibits angiogenesis. The antibody may bind to the ALK1 ligand with a $K_D$ of less than $1\times10^{-10}$ M. Such antibodies are preferably recombinant antibodies, and may be formulated as a pharmaceutical preparation that is substantially pyrogen free. The pharmaceutical preparation may be prepared for systemic delivery (e.g., intravenous, intraarterial or subcutaneous delivery) or local delivery (e.g., to the eye).

In certain aspects, the disclosure provides methods for inhibiting angiogenesis in a mammal, the method comprising, administering to the mammal an effective amount of an antibody that binds to an ALK1 ligand and inhibits the binding of the ALK1 ligand to ALK1, wherein the ALK1 ligand is selected from the group consisting of GDF5, GDF6, GDF7, BMP9 and BMP10. The antibody may inhibit angiogenesis stimulated by at least one ALK1 ligand selected from the group consisting of: GDF5, GDF6 and GDF7.

Members of the BMP/GDF family, including BMP9, BMP10, GDF5, GDF6 and GDF7 bind to a type I and a type II receptor in order to form a functional signaling complex. The binding sites for these receptors are different. Accordingly, in certain embodiments, an antibody that binds to an ALK1 ligand and inhibits the ligand to ALK1 is an antibody that binds at or near the type I receptor binding site of the ligand.

In certain aspects, the disclosure provides methods for inhibiting angiogenesis in a mammal by administering other inhibitors of the ALK1 signaling system disclosed herein. Such inhibitors may include nucleic acids (e.g., antisense or RNAi constructs) that decrease the production of ALK1, GDF5, GDF6, GDF7, BMP9 or BMP10). A variety of affinity binding reagents can also be used, such as aptamers, random peptides, protein scaffolds that can be modified to allow binding to selected targets (examples of such scaffolds include anticalins and FNIII domains); in each case, an affinity binding reagent would be selected for the ability to disrupt the ALK1 regulatory system disclosed herein, either by disrupting the ALK1-ligand interaction or by inhibiting the signaling that occurs after binding.

In a further embodiment, the disclosure describes the role of DAN as a regulator of the ALK1 regulatory system. As shown herein, DAN binds to the GDF5 group of ligands but fails to bind to the BMP9 group of ligands. Thus, DAN is expected to inhibit angiogenesis mediated by GDF5, GDF6 or GDF7 but not angiogenesis mediated by BMP9 or BMP10. DAN may therefore be used as a selective agent for inhibiting angiogenesis in the bone or joints, where the GDF5 group of proteins is primarily expressed. Thus, in certain embodiments the disclosure provides DAN proteins for use as anti-angiogenic agents in the context of bone or joint angiogenesis, including rheumatoid arthritis and cancers that involve the bone or joints (e.g., multiple myeloma and bone metastases). A DAN protein will generally bind to one or more ALK1 ligands selected from the group consisting of: GDF5, GDF6 and GDF7, while having relatively poor binding to BMP9 or BMP10. A DAN protein may comprise an amino acid sequence that is at least 70%, 80%, 90%, 95%, 96%, 97%, 98%, 99% or 100% identical to the sequence of amino acids corresponding to amino acids 17-180 of SEQ ID NO:10 (mature human DAN) or amino acids 21-125 of SEQ ID NO:10 (conserved cysteine knot domain of DAN). A DAN protein may also be encoded by a nucleic acid that comprises a sequence the complement of which hybridizes under stringent hybridization conditions to nucleotides 153-467 of SEQ ID NO:11 or a variant of nucleotides 153-467 of SEQ ID NO:11 that has the same coding sequence (a "silent" variant, such as a variant containing one or more alterations at a wobble position in the triplet code), or to nucleotides 93-635 of SEQ ID NO:11 or a silent variant thereof. In certain aspects, the DAN protein is a fusion protein, such as an Fc fusion protein. While DAN is expected to be particularly useful for the inhibition of angiogenesis in bone and joints (including tumors located in the bone or joints, such as multiple myeloma and bone metastases), it may also be useful in other contexts, such as in a tumor located elsewhere, or in the eye.

According to another aspect of the invention, a method of inhibiting angiogenesis in a mammal is provided. The method comprises administering to the mammal an effective amount of an antagonist of BMP9 and/or BMP10. In some embodiments, the antagonist is an antibody that binds to BMP9 and/or BMP10. The antibody may be a polyclonal, monoclonal, and chimeric or a humanized antibody. The antagonist may be a Fd, Fv, Fab, F(ab'), $F(ab)_2$, or $F(ab')_2$ fragment, single chain Fv (scFv), diabody, triabody, tetrabody, minibody or a peptibody. In some embodiments the antagonist is an aptamer (peptide or nucleic acid). Given the overlapping effects of antagonists of BMP9 and BMP10, as demonstrated herein, the disclosure provides for antagonists of both BMP9 and BMP10, such as antibodies that cross-react and thus antagonize both proteins effectively (e.g., affinity less than 10 nM or less than 1 nM for both BMP9 and BMP10). Another example is ALK-1-Fc, which binds to both BMP9 and BMP10 and inhibits the activities of both ligands.

The antagonist may be an inhibitor of BMP9 and/or BMP10 expression. In some embodiments the antagonist is a nucleic acid that inhibits BMP9 and/or BMP10 expression. The nucleic acid may be an antisense or RNAi nucleic acid.

The antagonist may be a non-antibody protein that binds to BMP9 and/or BMP10. The antagonist may be a member of a GDF Trap family. Examples of the GDF Trap family include but are not limited to follistatin, FLRG, noggin and gremlin.

In some embodiments, the antagonist is a polypeptide that comprises an amino acid sequence was selected from a library of amino acid sequences by a method comprising a step of detecting binding to BMP9 and BMP10.

In certain aspects, the disclosure provides methods for treating rheumatoid arthritis in a mammal, the method comprising, administering to a mammal that has rheumatoid arthritis an effective amount of an agent selected from the group consisting of: an ALK1 ECD protein; an antibody that binds to an ALK1 ligand and inhibits the binding of the ALK1 ligand to ALK1, wherein the ALK1 ligand is selected from the group consisting of GDF5, GDF6, GDF7, BMP9 and BMP10; an antibody that binds to an ALK1 polypeptide consisting of amino acids 22-118 of SEQ ID NO:1 and inhibits the binding of at least one ALK1 ligand selected from the group consisting of: GDF5, GDF6, GDF7, BMP9 and BMP10; and a DAN polypeptide.

In certain aspects the disclosure provides methods for treating a tumor in a mammal. Such a method may comprise administering to a mammal that has a tumor an effective amount of an agent selected from the group consisting of: an ALK1 ECD protein; an antibody that binds to an ALK1 ligand and inhibits the binding of the ALK1 ligand to ALK1, wherein the ALK1 ligand is selected from the group consisting of GDF5, GDF6, GDF7, BMP9 and BMP10; an antibody that binds to an ALK1 polypeptide consisting of amino acids 22-118 of SEQ ID NO:1 and inhibits the binding of at least one ALK1 ligand selected from the group consisting of: GDF5, GDF6, GDF7, BMP9 and BMP10; and a DAN polypeptide. A method may further comprise administering a second agent that inhibits angiogenesis. A tumor may be a tumor that is associated with bone, such as a leukemia, a bone marrow tumor, a multiple myeloma or bone metastases, such as those commonly associated with breast or prostate cancer. A tumor may be a melanoma or lung cancer tumor. A tumor may also be one that utilizes multiple pro-angiogenic factors, such as a tumor that is resistant to anti-VEGF therapy.

In certain aspects the disclosure provides ophthalmic formulations. Such formulations may comprise an agent selected from the group consisting of: an ALK1 ECD protein; an antibody that binds to an ALK1 ligand and inhibits the binding of the ALK1 ligand to ALK1, wherein the ALK1 ligand is selected from the group consisting of GDF5, GDF6, GDF7, BMP9 and BMP10; an antibody that binds to an ALK1 polypeptide consisting of amino acids 22-118 of SEQ ID NO:1 and inhibits the binding of at least one ALK1 ligand selected from the group consisting of: GDF5, GDF6, GDF7, BMP9 and BMP10; and a DAN polypeptide.

In certain aspects, the disclosure provides methods for treating an angiogenesis related disease of the eye. Such methods may comprise administering systemically or to said eye a pharmaceutical formulation comprising: an effective amount of an agent selected from the group consisting of: an ALK1 ECD protein; an antibody that binds to an ALK1 ligand and inhibits the binding of the ALK1 ligand to ALK1, wherein the ALK1 ligand is selected from the group consisting of GDF5, GDF6, GDF7, BMP9 and BMP10; an antibody that binds to an ALK1 polypeptide consisting of amino acids 22-118 of SEQ ID NO:1 and inhibits the binding of at least one ALK1 ligand selected from the group consisting of: GDF5, GDF6, GDF7, BMP9 and BMP10; and a DAN polypeptide.

In each instance, an agent described herein may be administered in conjunction with a second agent that inhibits angiogenesis. Where it is desirable to inhibit angiogenesis of a tumor, the agent may be administered in conjunction with a second agent that has an anti-cancer effect, such as a chemotherapeutic agent or a biologic anti-cancer agent.

The disclosure also provides an ophthalmic pharmaceutical formulation comprising an ALK1-Fc fusion protein having an amino acid sequence that is at least 97% identical to the sequence of amino acids 22-118 of SEQ ID NO:1, which polypeptide is fused to an Fc portion of an immunoglobulin, and wherein the ALK1-Fc fusion protein binds to GDF5, GDF7, BMP9 and/or BMP10 with a $K_D$ of less than $1\times10^{-7}$ M and/or binds to TGFβ-1 with a $K_D$ of greater than $1\times10^{-6}$. In one embodiment, the fusion protein has the sequence of SEQ ID NO: 3. In one embodiment, the Fc portion is from human IgG1. In one embodiment, the fusion protein is produced by expression of the nucleic acid of SEQ ID NO:4 in a mammalian cell line. In one embodiment, the cell line is Chinese Hamster Ovary cell line. The formulation may further comprise one or more of the following medicaments: pegaptanib, ranibizumab, or a glucocorticoid. In one embodiment, the formulation is substantially pyrogen free.

The application also provides for an ophthalmic pharmaceutical formulation comprising an antibody that binds to an ALK1 polypeptide consisting of amino acids 22-118 of SEQ ID NO:1 and inhibits the binding of at least one ALK1 ligand selected from the group consisting of: GDF5, GDF6, GDF7, BMP9 and BMP10. In one embodiment, the antibody inhibits angiogenesis stimulated by at least one ALK1 ligand selected from the group consisting of: GDF5, GDF6 and GDF7. In one embodiment, the antibody binds to the ALK1 polypeptide with a $K_D$ of less than $5\times10^{-8}$ M. In another embodiment, the antibody binds to the ALK1 polypeptide with a $K_D$ of less than $1\times10^{-10}$ M. In one embodiment, the antibody inhibits angiogenesis stimulated by GDF5, GDF6, GDF7, BMP9, or BMP10. The formulation may further comprise one or more of the following medicaments: pegaptanib, ranibizumab, or a glucocorticoid. In one embodiment, the formulation is substantially pyrogen free.

In certain aspects, the disclosure provides for an ophthalmic pharmaceutical formulation comprising an antibody that binds to an ALK1 ligand disclosed herein and inhibits the binding of the ALK1 ligand to ALK1. In certain embodiments, the antibody binds to a ligand selected from the group consisting of GDF5, GDF6 and GDF7. The antibody may bind to the ALK1 ligand with a $K_D$ of less than $5\times10^{-8}$ M. The antibody may be selected for inhibition of angiogenesis stimulated by the ALK1 ligand. A CAM assay is an appropriate assay system for selection of desirable antibodies. As shown herein, an antibody to BMP9 inhibits VEGF-mediated angiogenesis in a CAM assay. Such antibodies are preferably recombinant antibodies. The formulation may further comprise one or more of the following medicaments: pegaptanib, ranibizumab, or a glucocorticoid. In one embodiment, the formulation is substantially pyrogen free.

The application also provides methods of treating an angiogenesis related disease of the eye comprising administering to said eye an ophthalmic pharmaceutical formulation comprising an ALK1-Fc fusion protein comprising: a polypeptide having an amino acid sequence that is at least 97% identical to the sequence of amino acids 22-118 of SEQ ID NO:1, which polypeptide is fused to an Fc portion of an immunoglobulin, and wherein the ALK1-Fc fusion protein binds to GDF5, GDF7, BMP9 and/or BMP10 with a $K_D$ of less than $1\times10^{-7}$ M and/or binds to TGFβ-1 with a $K_D$ of greater than $1\times10^{-6}$. In one embodiment, the fusion protein has the sequence of SEQ ID NO: 3. In one embodiment, the Fc portion is from human IgG1. In one embodiment, the fusion protein is produced by expression of the nucleic acid of SEQ ID NO:4 in a mammalian cell line. In one embodiment, the cell line is Chinese Hamster Ovary cell line. The formulation may further comprise one or more of the following medicaments: pegaptanib, ranibizumab, or a glucocorticoid. In one embodiment, the formulation is substantially pyrogen free.

The application also provides methods of treating an angiogenesis related disease of the eye comprising administering to said eye an ophthalmic pharmaceutical formulation comprising an antibody that binds to an ALK1 polypeptide consisting of amino acids 22-118 of SEQ ID NO:1 and inhibits the binding of at least one ALK1 ligand selected from the group consisting of: GDF5, GDF6, GDF7, BMP9 and BMP10. In one embodiment, the antibody inhibits angiogenesis stimulated by at least one ALK1 ligand selected from the group consisting of: GDF5, GDF6 and GDF7. In one embodiment, the antibody binds to the ALK1 polypeptide with a $K_D$ of less than $5\times10^{-8}$ M. In another embodiment, the antibody binds to the ALK1 polypeptide with a $K_D$ of less than $1\times10^{-10}$ M. In one embodiment, the antibody inhibits angiogenesis stimulated by GDF5, GDF6, GDF7, BMP9, or BMP10. The formulation may further comprise one or more of the following medicaments: pegaptanib, ranibizumab, or a glucocorticoid. In one embodiment, the formulation is substantially pyrogen free.

In one embodiment of the disclosed methods, the angiogenesis related disease is selected from the group consisting of a tumor, a tumor that is resistant to anti-VEGF therapy, a multiple myeloma tumor, a tumor that has metastasized to the bone, joint or bone inflammation, rheumatoid arthritis, diabetic retinopathy, retinopathy of prematurity, macular degeneration, corneal graft rejection, neovascular glaucoma, and retrolental fibroplasias.

BRIEF DESCRIPTION OF THE DRAWINGS

FIG. 1 shows the amino acid sequence for the human Activin Like Kinase 1, ALK1 (SEQ ID NO:1). Single underlining shows the predicted extracellular domain. Double underlining shows the intracellular domain. The signal peptide and the transmembrane domain are not underlined.

FIG. 2 shows the nucleic acid sequence of a human ALK1 cDNA (SEQ ID NO:2). The coding sequence is underlined. The portion encoding the extracellular domain is double underlined.

FIG. 3 shows an example of a fusion of the extracellular domain of human ALK1 to an Fc domain (SEQ ID NO:3). The hALK1-Fc protein includes amino acids 22-120 of the human ALK1 protein, fused at the C-terminus to a linker (underlined) and an IgG1 Fc region.

FIG. 4 shows the nucleic acid sequence for expression of the hALK1-Fc polypeptide of SEQ ID NO:3. The encoded amino acid sequence is also shown. The leader sequence is cleaved such that Asp 22 is the N-terminal amino acid of the secreted protein.

FIG. 11 shows resolution of hALK1-Fc (SEQ ID NO: 3) and an hALK1-Fc fusion protein from R&D Systems (Minneapolis, Minn.) by Superose 12 10/300 GL Size Exclusion column (Amersham Biosciences, Piscataway, N.J.). The R&D Systems material contains approximately 13% aggregated protein, as shown by the peaks on the left hand side of the graph, as well as some lower molecular weight species. The material of SEQ ID NO:3 is greater than 99% composed of dimers of the appropriate molecular size.

FIG. 19 shows an alignment of the mature portions of the human BMP9 (SEQ ID NO:12) and BMP10 (SEQ ID NO:13) proteins. Regions of identity are shown with asterisks.

DETAILED DESCRIPTION

1. Overview

Figure 5:
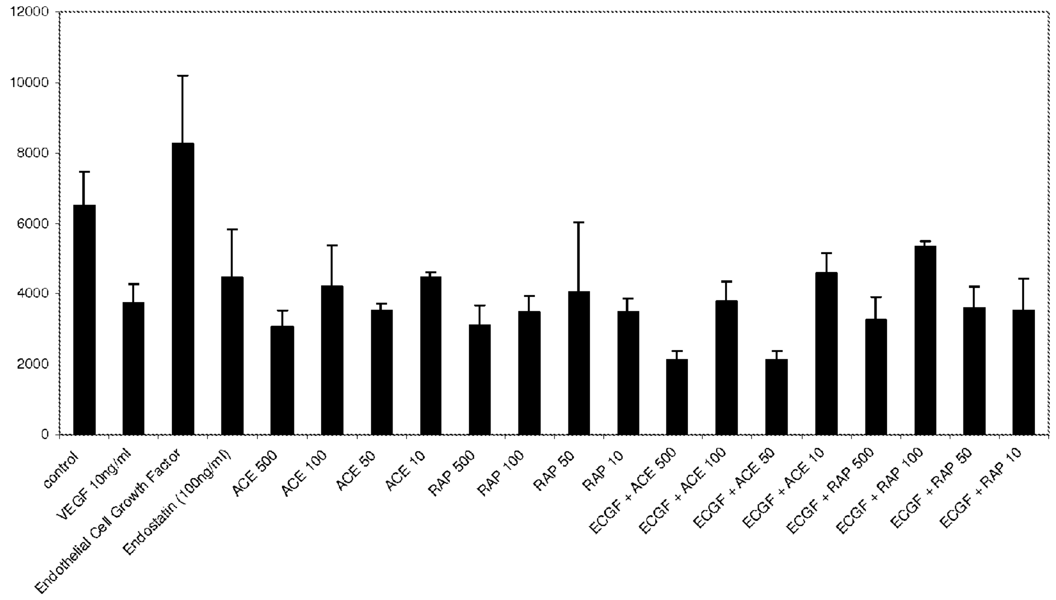
FIG. 5 shows the anti-angiogenic effect of murine ALK1-Fc ("RAP") and human ALK1-Fc ("ACE") in an endothelial cell tube forming assay. All concentrations of RAP and ACE reduced the level of tube formation in response to Endothelial Cell Growth Supplement (ECGF) to a greater degree than the positive control, Endostatin.

ALK1 is a type I cell-surface receptor for the TGF-β superfamily of ligands and is also known as ACVRL1 and ACVRLK1. ALK1 has been implicated as a receptor for TGF-β1, TGF-β3 and BMP-9 (Marchuk et al., Hum Mol Genet. 2003; Brown et al., J Biol Chem. 2005 Jul. 1; 280(26):25111-8).

In mice, loss-of-function mutations in ALK1 lead to a variety of abnormalities in the developing vasculature (Oh et al., Proc. Natl. Acad. Sci. USA 2000, 97, 2626-2631; Urness et al., Nat. Genet. 2000, 26, 328-331).

In humans, loss-of-function mutations in ALK1 are associated with hereditary hemorrhagic telangiectasia (HHT, or Osler-Rendu-Weber syndrome), in which patients develop arteriovenous malformations that create direct flow (communication) from an artery to a vein (arteriovenous shunt), without an intervening capillary bed. Typical symptoms of patients with HHT include recurrent epistaxis, gastrointestinal hemorrhage, cutaneous and mucocutaneous telangiectases, and arteriovenous malformations (AVM) in the pulmonary, cerebral, or hepatic vasculature.

Recent publications from David et al. (Blood. 2007 Mar. 1; 109(5):1953-61.) and Scharpfenecker et al. (J Cell Sci. 2007 Mar. 15; 120(Pt 6):964-72) conclude that BMP9 and BMP10 activate ALK1 in endothelial cells, and that the consequence of this activation is to inhibit endothelial cell proliferation and migration. These effects are directly opposed to those of pro-angiogenic factors such as VEGF. Thus, these publications conclude that BMP9 and BMP10 are themselves anti-angiogenic factors, and further, that ALK1 activation has an anti-angiogenic effect. By contrast, the present disclosure demonstrates that antagonists, rather than agonists, of BMP9 and BMP10 have anti-angiogenic effects.

The disclosure relates to the discovery that polypeptides comprising a portion of the extracellular domain of ALK1 ("ALK1 ECD polypeptides") may be used to inhibit angiogenesis in vivo, including VEGF-independent angiogenesis and angiogenesis that is mediated by multiple angiogenic factors, including VEGF, FGF and PDGF. In part, the disclosure provides the identity of physiological, high affinity ligands for ALK1 and demonstrates that ALK1 ECD polypeptides inhibit angiogenesis. The data demonstrate that an ALK1 ECD polypeptide can exert an anti-angiogenic effect even in the case where the ALK1 ECD polypeptide does not exhibit meaningful binding to TGF-β1. Moreover, ALK1 ECD polypeptides inhibit angiogenesis that is stimulated by many different pro-angiogenic factors, including VEGF, FGF, and GDF7. Thus, the disclosure provides a description of an ALK1 regulatory system, in which ALK1 is a receptor for the GDF5 group of ligands, which includes GDF6 and GDF7, and also for the BMP9 group of ligands, which includes BMP10, with different affinities for the two groups of ligands. It was demonstrated that antagonists of the ALK1 signaling pathway are effective against tumors or cancers including, for example, breast, lung, estrogen receptor positive (ER+), estrogen receptor negative (ER−), bone, tumor or cancer metastasized to bone, melanoma, and multiple myeloma (see, for example WO 2008/057461). Further, the disclosure demonstrates that signaling mediated by ALK1 and the ligands described above is pro-angiogenic in vivo, and that inhibition of this regulatory system has a potent anti-angiogenic effect in vivo. Thus, in certain aspects, the disclosure provides antagonists of the ALK1 regulatory system, including antagonists of the receptor or one or more of the ligands, for use in inhibiting angiogenesis, including both VEGF-dependent angiogenesis and VEGF-independent angiogenesis. However, it should be noted that antibodies directed to ALK1 itself are expected to have different effects from an ALK1 ECD polypeptide. A pan-neutralizing antibody against ALK1 (one that inhibits the binding of all strong and weak ligands) would be expected to inhibit the signaling of such ligands through ALK1 but would not be expected to inhibit the ability of such ligands to signal through other receptors (e.g., BMPR1a, BMPR1b, BMPRII in the case of GDF5-7 and BMP9-10 and TBRI and TBRII in the case of TGFβ). On the other hand, an ALK1 ECD polypeptide would be expected to inhibit all of the ligands that it binds to tightly, including, for a construct such as that shown in the Examples, GDF5-7 and BMP9-10, but would not affect ligands that it binds to weakly, such as TGF-β. So, while a pan-neutralizing antibody against ALK1 would block BMP9 and TGF-β signaling through ALK1 it would not block BMP9 and TGF-β signaling through another receptor, and while an ALK1 ECD polypeptide may inhibit BMP9 signaling through all receptors (even receptors other than ALK1) it would not be expected to inhibit TGF-β signaling through any receptor, even ALK1.

Proteins described herein are the human forms, unless otherwise specified. Genbank references for the proteins are as follows: human GDF5, CAA56874; human GDF6, AAH43222; human GDF7, NP_878248; human BMP9, Q9UK05; human BMP10, O95393; human DAN, BAA92265. ALK1 sequences are set forth in FIGS. 1-5.

Human Dan amino acid sequence (SEQ ID NO:10) (Genbank BAA92265):

```
MLRVLVGAVL PAMLLAAPPP INKLALFPDK SAWCEAKNIT QIVGHSGCEA KSIQNRACLG
QCFSYSVPNT FPQSTESLVH CDSCMPAQSM WEIVTLECPG HEEVPRVDKL VEKILHCSCQ
ACGKEPSHEG LSVYVQGEDG PGSQPGTHPH PHPHPHPGGQ TPEPEDPPGA PHTEEEGAED
```

The mature Dan protein is expected to correspond to amino acids 17-180. The conserved cysteine knot domain of Dan corresponds to amino acids 21-125 (underlined).

Human Dan cDNA sequence (SEQ ID NO: 11)
(Genbank BC012037):

```
gccgagcctc ctggggcgcc cgggcccgcg acccccgcac ccagctccgc aggaccggcg
ggcgcgcgcg ggctctggag gccacgggca tgatgcttcg ggtcctggtg ggggctgtcc
tccctgccat gctactggct gccccaccac ccatcaacaa gctggcactg ttcccagata
agagtgcctg gtgcgaagcc aagaacatca cccagatcgt gggccacagc ggctgtgagg
ccaagtccat ccagaacagg gcgtgcctag gacagtgctt cagctacagc gtccccaaca
ccttcccaca gtccacagag tccctggttc actgtgactc ctgcatgcca gcccagtcca
tgtgggagat tgtgacgctg gagtgcccgg gccacgagga ggtgcccagg gtggacaagc
tggtggagaa gatcctgcac tgtagctgcc aggcctgcgg caaggagcct agtcacgagg
ggctgagcgt ctatgtgcag ggcgaggacg ggccgggatc ccagcccggc acccaccctc
acccccatcc ccaccccccat cctggcgggc agacccctga gcccgaggac ccccctgggg
ccccccacac agaggaagag gggggctgagg actgaggccc ccccaactct tcctcccctc
tcatccccct gtggaatgtt gggtctcact ctctggggaa gtcaggggag aagctgaagc
ccccctttgg cactggatgg acttggcttc agactcggac ttgaatgctg cccggttgcc
atggagatct gaaggggcgg ggttagagcc aagctgcaca atttaatata ttcaagagtg
gggggaggaa gcagaggtct tcagggctct ttttttgggg ggggggtggt ctcttcctgt
ctggcttcta gagatgtgcc tgtgggaggg ggaggaagtt ggctgagcca ttgagtgctg
ggggaggcca tccaagatgg catgaatcgg gctaaggtcc ctgggggtgc agatggtact
gctgaggtcc cgggcttagt gtgagcatct tgccagcctc aggcttgagg gagggctggg
ctagaaagac cactggcaga aacaggaggc tccggcccca caggtttccc caaggcctct
caccccactt cccatctcca gggaagcgtc gccccagtgg cactgaagtg gccctccctc
agcggagggg tttgggagtc aggcctgggc aggaccctgc tgactcgtgg cgcgggagct
gggagccagg ctctccgggc ctttctctgg cttccttggc ttgcctggtg ggggaagggg
aggaggggaa gaaggaaagg gaagagtctt ccaaggccag aaggaggggg acaacccccc
aagaccatcc ctgaagacga gcatccccct cctctccctg ttagaaatgt tagtgccccg
cactgtgccc caagttctag gccccccaga aagctgtcag agccggccgc cttctcccct
ctcccaggga tgctctttgt aaatatcgga tgggtgtggg agtgaggggt tacctccctc
```

-continued

```
gccccaaggt tccagaggcc ctaggcggga tgggctcgct gaacctcgag gaactccagg

acgaggagga catgggactt gcgtggacag tcagggttca cttgggctct ctctagctcc

ccaattctgc ctgcctcctc cctcccagct gcactttaac cctagaaggt ggggacctgg

ggggagggac agggcaggcg ggcccatgaa gaaagcccct cgttgcccag cactgtctgc

gtctgctctt ctgtgcccag ggtggctgcc agcccactgc ctcctgcctg gggtggcctg

gccctcctgg ctgttgcgac gcgggcttct ggagcttgtc accattggac agtctccctg

atggaccctc agtcttctca tgaataaatt ccttcaacgc caaaaaaaaa aaaaaaaaaa

aaaaaaaaaa aaaaaaaaaa aaa
```

The coding sequence for DAN precursor corresponds to nucleic acids 93-635. The coding sequence for the mature DAN protein corresponds to nucleic acids 141-632. The coding sequence for the conserved cysteine knot portion of DAN corresponds to nucleic acids 153-467.

The terms used in this specification generally have their ordinary meanings in the art, within the context of this disclosure and in the specific context where each term is used. Certain terms are discussed in the specification, to provide additional guidance to the practitioner in describing the compositions and methods disclosed herein and how to make and use them. The scope or meaning of any use of a term will be apparent from the specific context in which the term is used.

2. Soluble ALK1 Polypeptides

Naturally occurring ALK1 proteins are transmembrane proteins, with a portion of the protein positioned outside the cell (the extracellular portion) and a portion of the protein positioned inside the cell (the intracellular portion). Aspects of the present disclosure encompass polypeptides comprising a portion of the extracellular domain of ALK1.

In certain embodiments, the disclosure provides "ALK1 ECD polypeptides". The term "ALK1 ECD polypeptide" is intended to refer to a polypeptide consisting of or comprising an amino acid sequence of an extracellular domain of a naturally occurring ALK1 polypeptide, either including or excluding any signal sequence and sequence N-terminal to the signal sequence, or an amino acid sequence that is at least 33 percent identical to an extracellular domain of a naturally occurring ALK1 polypeptide, and optionally at least 60%, at least 70%, at least 80%, at least 85%, at least 90%, at least 95%, at least 96%, at least 97%, at least 98%, at least 99% or 100% identical to the sequence of an extracellular domain of a naturally occurring ALK1 polypeptide, as exemplified by the cysteine knot region of amino acids 34-95 of SEQ ID NO:1 or the cysteine knot plus additional amino acids at the N- and C-termini of the extracellular domain, such as amino acids 22-118 of SEQ ID NO. 1. Likewise, an ALK1 ECD polypeptide may comprise a polypeptide that is encoded by nucleotides 100-285 of SEQ ID NO:2, or silent variants thereof or nucleic acids that hybridize to the complement thereof under stringent hybridization conditions (generally, such conditions are known in the art but may, for example, involve hybridization in 50% v/v formamide, 5×SSC, 2% w/v blocking agent, 0.1% N-lauroylsarcosine, 0.3% SDS at 65° C. overnight and washing in, for example, 5×SSC at about 65° C. Additionally, an ALK1 ECD polypeptide may comprise a polypeptide that is encoded by nucleotides 64-384 of SEQ ID NO:2, or silent variants thereof or nucleic acids that hybridize to the complement thereof under stringent hybridization conditions (generally, such conditions are known in the art but may, for example, involve hybridization in 50% v/v formamide, 5×SSC, 2% w/v blocking agent, 0.1% N-lauroylsarcosine, 0.3% SDS at 65° C. overnight and washing in, for example, 5×SSC at about 65° C.). The term "ALK1 ECD polypeptide" accordingly encompasses isolated extracellular portions of ALK1 polypeptides, variants thereof (including variants that comprise, for example, no more than 2, 3, 4, 5 or 10 amino acid substitutions, additions or deletions in the sequence corresponding to amino acids 22-118 of SEQ ID NO:1 and including variants that comprise no more than 2, 3, 4, 5, or 10 amino acid substitutions, additions or deletions in the sequence corresponding to amino acids 34-95 of SEQ ID NO:1), fragments thereof and fusion proteins comprising any of the preceding, but in each case preferably any of the foregoing ALK1 ECD polypeptides will retain substantial affinity for one or more of GDF5, GDF6, GDF7, BMP9 or BMP10. The term "ALK1 ECD polypeptide" is explicitly intended to exclude any full-length, naturally occurring ALK1 polypeptide. Generally, an ALK1 ECD polypeptide will be designed to be soluble in aqueous solutions at biologically relevant temperatures, pH levels and osmolarity.

As described above, the disclosure provides ALK1 ECD polypeptides sharing a specified degree of sequence identity or similarity to a naturally occurring ALK1 polypeptide. To determine the percent identity of two amino acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The amino acid residues at corresponding amino acid positions are then compared. When a position in the first sequence is occupied by the same amino acid residue as the corresponding position in the second sequence, then the molecules are identical at that position (as used herein amino acid "identity" is equivalent to amino acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

In one embodiment, the percent identity between two amino acid sequences is determined using the Needleman and Wunsch (J Mol. Biol. (48):444-453 (1970)) algorithm which has been incorporated into the GAP program in the GCG software package (available at www.gcg.com). In a specific embodiment, the following parameters are used in the GAP program: either a Blosum 62 matrix or a PAM250 matrix, and a gap weight of 16, 14, 12, 10, 8, 6, or 4 and a length weight of 1, 2, 3, 4, 5, or 6. In yet another embodiment, the percent identity between two nucleotide sequences is determined using the GAP program in the GCG software package (Devereux, J., et al., Nucleic Acids Res. 12(1):387 (1984)) (available at www.gcg.com). Exemplary parameters include using a NWSgapdna.CMP matrix and a gap weight of 40, 50, 60, 70, or 80 and a length weight of 1, 2, 3, 4, 5, or 6. Unless otherwise specified, percent identity between two amino acid sequences is to be determined using the GAP program using a Blosum 62 matrix, a GAP weight of 10 and a length weight of 3, and if such algorithm cannot compute the desired percent identity, a suitable alternative disclosed herein should be selected.

In another embodiment, the percent identity between two amino acid sequences is determined using the algorithm of E. Myers and W. Miller (CABIOS, 4:11-17 (1989)) which has been incorporated into the ALIGN program (version 2.0), using a PAM120 weight residue table, a gap length penalty of 12 and a gap penalty of 4.

Another embodiment for determining the best overall alignment between two amino acid sequences can be determined using the FASTDB computer program based on the algorithm of Brutlag et al. (*Comp. App. Biosci.,* 6:237-245 (1990)). In a sequence alignment the query and subject sequences are both amino acid sequences. The result of said global sequence alignment is presented in terms of percent identity. In one embodiment, amino acid sequence identity is performed using the FASTDB computer program based on the algorithm of Brutlag et al. (*Comp. App. Biosci.,* 6:237-245 (1990)). In a specific embodiment, parameters employed to calculate percent identity and similarity of an amino acid alignment comprise: Matrix=PAM 150, k-tuple=2, Mismatch Penalty=1, Joining Penalty=20, Randomization Group Length=0, Cutoff Score=1, Gap Penalty=5 and Gap Size Penalty=0.05.

In certain embodiments, ALK1 ECD polypeptides comprise an extracellular portion of a naturally occurring ALK1 protein such as a sequence of SEQ ID NO:1, and preferably a ligand binding portion of the ALK1 extracellular domain. In certain embodiments, a soluble ALK1 polypeptide comprises an amino acid sequence that is at least 60%, 70%, 80%, 85%, 90%, 95%, 96%, 97%, 98%, or 99% identical to an amino acid sequence of amino acids 22-118 of the SEQ ID NO:1. In certain embodiments, a truncated extracellular ALK1 polypeptide comprises at least 30, 40 or 50 consecutive amino acids of an amino acid sequence of an extracellular portion of SEQ ID NO:1.

In preferred embodiments, an ALK1 ECD polypeptide binds to one or more of GDF5, GDF6, GDF7, BMP9 and BMP10. Optionally the ALK1 polypeptide does not show substantial binding to TGF-β1 or TGF-β3. Binding may be assessed using purified proteins in solution or in a surface plasmon resonance system, such as a Biacore™ system. Preferred soluble ALK1 polypeptides will exhibit an anti-angiogenic activity. Bioassays for angiogenesis inhibitory activity include the chick chorioallantoic membrane (CAM) assay, the mouse corneal micropocket assay, an assay for measuring the effect of administering isolated or synthesized proteins on implanted tumors. The CAM assay is described by O'Reilly, et al. in "Angiogenic Regulation of Metastatic Growth" Cell, vol. 79 (2), Oct. 1, 1994, pp. 315-328. Briefly, 3 day old chicken embryos with intact yolks are separated from the egg and placed in a petri dish. After 3 days of incubation, a methylcellulose disc containing the protein to be tested is applied to the CAM of individual embryos. After 48 hours of incubation, the embryos and CAMs are observed to determine whether endothelial growth has been inhibited. The mouse corneal micropocket assay involves implanting a growth factor-containing pellet, along with another pellet containing the suspected endothelial growth inhibitor, in the cornea of a mouse and observing the pattern of capillaries that are elaborated in the cornea. Other assays are described in the Examples.

ALK1 ECD polypeptides may be produced by removing the cytoplasmic tail and the transmembrane region of an ALK1 polypeptide. Alternatively, the transmembrane domain may be inactivated by deletion, or by substitution of the normally hydrophobic amino acid residues which comprise a transmembrane domain with hydrophilic ones. In either case, a substantially hydrophilic hydropathy profile is created which will reduce lipid affinity and improve aqueous solubility. Deletion of the transmembrane domain is preferred over substitution with hydrophilic amino acid residues because it avoids introducing potentially immunogenic epitopes.

ALK1 ECD polypeptides may additionally include any of various leader sequences at the N-terminus. Such a sequence would allow the peptides to be expressed and targeted to the secretion pathway in a eukaryotic system. See, e.g., Ernst et al., U.S. Pat. No. 5,082,783 (1992). Alternatively, a native ALK1 signal sequence may be used to effect extrusion from the cell. Possible leader sequences include native, tPa and honeybee mellitin leaders (SEQ ID Nos. 7-9, respectively). Processing of signal peptides may vary depending on the leader sequence chosen, the cell type used and culture conditions, among other variables, and therefore actual N-terminal start sites for mature ALK1 ECD polypeptides, including that of SEQ ID NO:5, may shift by 1-5 amino acids in either the N-terminal or C-terminal direction.

In certain embodiments, the present disclosure contemplates specific mutations of the ALK1 polypeptides so as to alter the glycosylation of the polypeptide. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine (or asparagines-X-serine) (where "X" is any amino acid) which is specifically recognized by appropriate cellular glycosylation enzymes. The alteration may also be made by the addition of, or substitution by, one or more serine or threonine residues to the sequence of the wild-type ALK1 polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on an ALK1 polypeptide is by chemical or enzymatic coupling of glycosides to the ALK1 polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. These methods are described in WO 87/05330 published Sep. 11, 1987, and in Aplin and Wriston (1981) CRC Crit. Rev. Biochem., pp. 259-306, incorporated by reference herein. Removal of one or more carbohydrate moieties present on an ALK1 polypeptide may be accomplished chemically and/or enzymatically. Chemical deglycosylation may involve, for example, exposure of the ALK1 polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Chemical deglycosylation is further described by Hakimuddin et al. (1987) Arch. Biochem. Biophys. 259:52 and by Edge et al. (1981) Anal. Biochem. 118:131. Enzymatic cleavage of carbohydrate moieties on ALK1 polypeptides can be achieved by the use of a variety of endo- and exo-glycosidases as described by Thotakura et al. (1987) Meth. Enzymol. 138:350. The sequence of an ALK1 polypeptide may be adjusted, as appropriate, depending on the type of expression system used, as mammalian, yeast, insect and plant cells may all introduce differing glycosylation patterns that can be affected by the amino acid sequence of the peptide. In general, ALK1 proteins for use in humans will be expressed in a mammalian cell line that provides proper glycosylation, such as HEK293 or CHO cell lines, although other mammalian expression cell lines, yeast cell lines with engineered glycosylation enzymes and insect cells are expected to be useful as well.

This disclosure further contemplates a method of generating mutants, particularly sets of combinatorial mutants of an ALK1 polypeptide, as well as truncation mutants; pools of combinatorial mutants are especially useful for identifying functional variant sequences. The purpose of screening such combinatorial libraries may be to generate, for example, ALK1 polypeptide variants which can act as either agonists or antagonist, or alternatively, which possess novel activities all together. A variety of screening assays are provided below, and such assays may be used to evaluate variants. For example, an ALK1 polypeptide variant may be screened for ability to bind to an ALK1 ligand, to prevent binding of an ALK1 ligand to an ALK1 polypeptide or to interfere with signaling caused by an ALK1 ligand. The activity of an ALK1 polypeptide or its variants may also be tested in a cell-based or in vivo assay, particularly any of the assays disclosed in the Examples.

Combinatorially-derived variants can be generated which have a selective or generally increased potency relative to an ALK1 ECD polypeptide comprising an extracellular domain of a naturally occurring ALK1 polypeptide. Likewise, mutagenesis can give rise to variants which have serum half-lives dramatically different than the corresponding a wild-type ALK1 ECD polypeptide. For example, the altered protein can be rendered either more stable or less stable to proteolytic degradation or other processes which result in destruction of, or otherwise elimination or inactivation of a native ALK1 ECD polypeptide. Such variants, and the genes which encode them, can be utilized to alter ALK1 ECD polypeptide levels by modulating the half-life of the ALK1 polypeptides. For instance, a short half-life can give rise to more transient biological effects and can allow tighter control of recombinant ALK1 ECD polypeptide levels within the patient. In an Fc fusion protein, mutations may be made in the linker (if any) and/or the Fc portion to alter the half-life of the protein.

A combinatorial library may be produced by way of a degenerate library of genes encoding a library of polypeptides which each include at least a portion of potential ALK1 polypeptide sequences. For instance, a mixture of synthetic oligonucleotides can be enzymatically ligated into gene sequences such that the degenerate set of potential ALK1 polypeptide nucleotide sequences are expressible as individual polypeptides, or alternatively, as a set of larger fusion proteins (e.g., for phage display).

There are many ways by which the library of potential ALK1 ECD variants can be generated from a degenerate oligonucleotide sequence. Chemical synthesis of a degenerate gene sequence can be carried out in an automatic DNA synthesizer, and the synthetic genes then be ligated into an appropriate vector for expression. The synthesis of degenerate oligonucleotides is well known in the art (see for example, Narang, S A (1983) Tetrahedron 39:3; Itakura et al., (1981) Recombinant DNA, Proc. 3rd Cleveland Sympos. Macromolecules, ed. A G Walton, Amsterdam: Elsevier pp 273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, ALK1 polypeptide variants can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of ALK1 polypeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of ALK1 polypeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Preferred assays include ALK1 ligand binding assays and ligand-mediated cell signaling assays.

In certain embodiments, the ALK1 ECD polypeptides of the disclosure may further comprise post-translational modifications in addition to any that are naturally present in the ALK1 polypeptides. Such modifications include, but are not limited to, acetylation, carboxylation, glycosylation, phosphorylation, lipidation, and acylation. As a result, the modified ALK1 ECD polypeptides may contain non-amino acid elements, such as polyethylene glycols, lipids, poly- or mono-saccharide, and phosphates. Effects of such non-amino acid elements on the functionality of an ALK1 ECD polypeptide may be tested as described herein for other ALK1 ECD polypeptide variants. When an ALK1 ECD polypeptide is produced in cells by cleaving a nascent form of the ALK1 polypeptide, post-translational processing may also be important for correct folding and/or function of the protein. Different cells (such as CHO, HeLa, MDCK, 293, WI38, NIH-3T3 or HEK293) have specific cellular machinery and characteristic mechanisms for such post-translational activities and may be chosen to ensure the correct modification and processing of the ALK1 polypeptides.

In certain aspects, functional variants or modified forms of the ALK1 ECD polypeptides include fusion proteins having at least a portion of the ALK1 ECD polypeptides and one or more fusion domains. Well known examples of such fusion domains include, but are not limited to, polyhistidine, Glu-Glu, glutathione S transferase (GST), thioredoxin, protein A, protein G, an immunoglobulin heavy chain constant region (Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with ($HIS_6$) fusion partners. As another example, a fusion domain may be selected so as to facilitate detection of the ALK1 ECD polypeptides. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain preferred embodiments, an ALK1 ECD polypeptide is fused with a domain that stabilizes the ALK1 polypeptide in vivo (a "stabilizer" domain). By "stabilizing" is meant anything that increases serum half life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of fusion domains that may be selected include multimerizing (e.g., dimerizing, tetramerizing) domains and functional domains.

As a specific example, the present disclosure provides a fusion protein comprising a soluble extracellular domain of ALK1 fused to an Fc domain (e.g., SEQ ID NO: 6).

```
THTCPPCPAPELLGGPSVFLFPPKPKDTLMISRTPEVTCVVVD (A) VSHEDPEVKFNW

YVDGVEVHNAKTKPREEQYNSTYRVVSVLTVLHQDWLNGKEYKCK (A) VSNKALPVPI

EKTISKAKGQPREPQVYTLPPSREEMTKNQVSLTCLVKGFYPSDIAVEWESNGQPENN

YKTTPPVLDSDGPFFLYSKLTVDKSRWQQGNVFSCSVMHEALHN (A) HYTQKSLSLSP

GK*
```

Optionally, the Fc domain has one or more mutations at residues such as Asp-265, lysine 322, and Asn-434. In certain cases, the mutant Fc domain having one or more of these mutations (e.g., Asp-265 mutation) has reduced ability of binding to the Fcγ receptor relative to a wildtype Fc domain. In other cases, the mutant Fc domain having one or more of these mutations (e.g., Asn-434 mutation) has increased ability of binding to the MHC class I-related Fc-receptor (FcRN) relative to a wildtype Fc domain.

It is understood that different elements of the fusion proteins may be arranged in any manner that is consistent with the desired functionality. For example, an ALK1 ECD polypeptide may be placed C-terminal to a heterologous domain, or, alternatively, a heterologous domain may be placed C-terminal to an ALK1 ECD polypeptide. The ALK1 ECD polypeptide domain and the heterologous domain need not be adjacent in a fusion protein, and additional domains or amino acid sequences may be included C- or N-terminal to either domain or between the domains.

As used herein, the term, "immunoglobulin Fc region" or simply "Fc" is understood to mean the carboxyl-terminal portion of an immunoglobulin chain constant region, preferably an immunoglobulin heavy chain constant region, or a portion thereof. For example, an immunoglobulin Fc region may comprise 1) a CH1 domain, a CH2 domain, and a CH3 domain, 2) a CH1 domain and a CH2 domain, 3) a CH1 domain and a CH3 domain, 4) a CH2 domain and a CH3 domain, or 5) a combination of two or more domains and an immunoglobulin hinge region. In a preferred embodiment the immunoglobulin Fc region comprises at least an immunoglobulin hinge region a CH2 domain and a CH3 domain, and preferably lacks the CH1 domain.

In one embodiment, the class of immunoglobulin from which the heavy chain constant region is derived is IgG (Igγ) (γ subclasses 1, 2, 3, or 4). Other classes of immunoglobulin, IgA (Igα), IgD (Igδ), IgE (Igε) and IgM (Igμ), may be used. The choice of appropriate immunoglobulin heavy chain constant region is discussed in detail in U.S. Pat. Nos. 5,541,087, and 5,726,044. The choice of particular immunoglobulin heavy chain constant region sequences from certain immunoglobulin classes and subclasses to achieve a particular result is considered to be within the level of skill in the art. The portion of the DNA construct encoding the immunoglobulin Fc region preferably comprises at least a portion of a hinge domain, and preferably at least a portion of a $CH_3$ domain of Fc gamma or the homologous domains in any of IgA, IgD, IgE, or IgM.

Furthermore, it is contemplated that substitution or deletion of amino acids within the immunoglobulin heavy chain constant regions may be useful in the practice of the methods and compositions disclosed herein. One example would be to introduce amino acid substitutions in the upper CH2 region to create an Fc variant with reduced affinity for Fc receptors (Cole et al. (1997) J. Immunol. 159:3613).

In certain embodiments, the present disclosure makes available isolated and/or purified forms of the ALK1 ECD polypeptides, which are isolated from, or otherwise substantially free of (e.g., at least 80%, 90%, 95%, 96%, 97%, 98%, or 99% free of), other proteins and/or other ALK1 ECD polypeptide species. ALK1 polypeptides will generally be produced by expression from recombinant nucleic acids.

In certain embodiments, the disclosure includes nucleic acids encoding soluble ALK1 polypeptides comprising the coding sequence for an extracellular portion of an ALK1 proteins. In further embodiments, this disclosure also pertains to a host cell comprising such nucleic acids. The host cell may be any prokaryotic or eukaryotic cell. For example, a polypeptide of the present disclosure may be expressed in bacterial cells such as *E. coli*, insect cells (e.g., using a baculovirus expression system), yeast, or mammalian cells. Other suitable host cells are known to those skilled in the art. Accordingly, some embodiments of the present disclosure further pertain to methods of producing the ALK1 ECD polypeptides. It has been established that an ALK1-Fc fusion protein set forth in SEQ ID NO:3 and expressed in CHO cells has potent anti-angiogenic activity.

DAN polypeptides, including variants of wild type DAN, and fusion proteins containing DAN proteins may be generated and characterized as described above with respect to ALK1 ECD proteins.

3. Nucleic Acids Encoding ALK1 Polypeptides

In certain aspects, the disclosure provides isolated and/or recombinant nucleic acids encoding any of the ALK1 polypeptides (e.g., ALK1 ECD polypeptides), including fragments, functional variants and fusion proteins disclosed herein. For example, SEQ ID NO: 2 encodes the naturally occurring human ALK1 precursor polypeptide, while SEQ ID NO: 4 encodes the precursor of an ALK1 extracellular domain fused to an IgG1 Fc domain. The subject nucleic acids may be single-stranded or double stranded. Such nucleic acids may be DNA or RNA molecules. These nucleic acids may be used, for example, in methods for making ALK1 polypeptides or as direct therapeutic agents (e.g., in an antisense, RNAi or gene therapy approach).

In certain aspects, the subject nucleic acids encoding ALK1 polypeptides are further understood to include nucleic acids that are variants of SEQ ID NO: 2 or 4. Variant nucleotide sequences include sequences that differ by one or more nucleotide substitutions, additions or deletions, such as allelic variants.

In certain embodiments, the disclosure provides isolated or recombinant nucleic acid sequences that are at least 80%, 85%, 90%, 95%, 96%, 97%, 98%, 99% or 100% identical to SEQ ID NO: 2 or 4. One of ordinary skill in the art will appreciate that nucleic acid sequences complementary to SEQ ID NO: 2 or 4, and variants of SEQ ID NO: 2 or 4 are also within the scope of this disclosure. In further embodiments, the nucleic acid sequences of the disclosure can be isolated, recombinant, and/or fused with a heterologous nucleotide sequence, or in a DNA library.

In other embodiments, nucleic acids of the disclosure also include nucleotide sequences that hybridize under highly stringent conditions to the nucleotide sequence designated in SEQ ID NO: 2 or 4, complement sequence of SEQ ID NO: 2 or 4, or fragments thereof. As discussed above, one of ordinary skill in the art will understand readily that appropriate stringency conditions which promote DNA hybridization can be varied. One of ordinary skill in the art will understand readily that appropriate stringency conditions which promote DNA hybridization can be varied. For example, one could perform the hybridization at 6.0×sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the disclosure provides nucleic acids which hybridize under low stringency conditions of 6×SSC at room temperature followed by a wash at 2×SSC at room temperature.

Isolated nucleic acids which differ from the nucleic acids as set forth in SEQ ID NOs: 2 or 4 due to degeneracy in the genetic code are also within the scope of the disclosure. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this disclosure.

In certain embodiments, the recombinant nucleic acids of the disclosure may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the disclosure. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects disclosed herein, the subject nucleic acid is provided in an expression vector comprising a nucleotide sequence encoding an ALK1 polypeptide and operably linked to at least one regulatory sequence. Regulatory sequences are art-recognized and are selected to direct expression of the ALK1 polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding an ALK1 polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid included in the disclosure can be produced by ligating the cloned gene, or a portion thereof, into a vector suitable for expression in either prokaryotic cells, eukaryotic cells (yeast, avian, insect or mammalian), or both. Expression vehicles for production of a recombinant ALK1 polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see *Molecular Cloning A Laboratory Manual,* 3rd Ed., ed. by Sambrook, Fritsch and Maniatis (Cold Spring Harbor Laboratory Press, 2001). In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In a preferred embodiment, a vector will be designed for production of the subject ALK1 polypeptides in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). As will be apparent, the subject gene constructs can be used to cause expression of the subject ALK1 polypeptides in cells propagated in culture, e.g., to produce proteins, including fusion proteins or variant proteins, for purification.

This disclosure also pertains to a host cell transfected with a recombinant gene including a coding sequence (e.g., SEQ ID NO: 2 or 4) for one or more of the subject ALK1 polypeptides. The host cell may be any prokaryotic or eukaryotic cell. For example, an ALK1 polypeptide disclosed herein may be expressed in bacterial cells such as *E. coli*, insect cells (e.g., using a baculovirus expression system), yeast, or mammalian cells. Other suitable host cells are known to those skilled in the art.

Accordingly, the present disclosure further pertains to methods of producing the subject ALK1 polypeptides, including ALK1 ECD polypeptides. For example, a host cell transfected with an expression vector encoding an ALK1 polypeptide can be cultured under appropriate conditions to allow expression of the ALK1 polypeptide to occur. The ALK1 polypeptide may be secreted and isolated from a mixture of cells and medium containing the ALK1 polypeptide. Alternatively, the ALK1 polypeptide may be retained cytoplasmically or in a membrane fraction and the cells harvested, lysed and the protein isolated. A cell culture includes host cells, media and other byproducts. Suitable media for cell culture are well known in the art. The subject ALK1 polypeptides can be isolated from cell culture medium, host cells, or both, using techniques known in the art for purifying proteins, including ion-exchange chromatography, gel filtration chromatography, ultrafiltration, electrophoresis, immunoaffinity purification with antibodies specific for particular epitopes of the ALK1 polypeptides and affinity purification with an agent that binds to a domain fused to the ALK1 polypeptide (e.g., a protein A column may be used to purify an ALK1-Fc fusion). In a preferred embodiment, the ALK1 polypeptide is a fusion protein containing a domain which facilitates its purification. In a preferred embodiment, purification is achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

In another embodiment, a fusion gene coding for a purification leader sequence, such as a poly-(His)/enterokinase cleavage site sequence at the N-terminus of the desired portion of the recombinant ALK1 polypeptide, can allow purification of the expressed fusion protein by affinity chromatography using a $Ni^{2+}$ metal resin. The purification leader sequence can then be subsequently removed by treatment with enterokinase to provide the purified ALK1 polypeptide (e.g., see Hochuli et al., (1987) *J. Chromatography* 411:177; and Janknecht et al., *PNAS USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

Examples of categories of nucleic acid compounds that are antagonists of ALK1, BMP9, BMP10, GDF5, GDF6 or GDF7 include antisense nucleic acids, RNAi constructs and catalytic nucleic acid constructs. A nucleic acid compound may be single or double stranded. A double stranded compound may also include regions of overhang or non-complementarity, where one or the other of the strands is single stranded. A single stranded compound may include regions of self-complementarity, meaning that the compound forms a so-called "hairpin" or "stem-loop" structure, with a region of double helical structure. A nucleic acid compound may comprise a nucleotide sequence that is complementary to a region consisting of no more than 1000, no more than 500, no more than 250, no more than 100 or no more than 50, 35, 30, 25, 22, 20 or 18 nucleotides of the full-length ALK1 nucleic acid sequence or ligand nucleic acid sequence. The region of complementarity will preferably be at least 8 nucleotides, and optionally at least 10 or at least 15 nucleotides, and optionally between 15 and 25 nucleotides. A region of complementarity may fall within an intron, a coding sequence or a noncoding sequence of the target transcript, such as the coding sequence portion. Generally, a nucleic acid compound will have a length of about 8 to about 500 nucleotides or base pairs in length, and optionally the length will be about 14 to about 50 nucleotides. A nucleic acid may be a DNA (particularly for use as an antisense), RNA or RNA:DNA hybrid. Any one strand may include a mixture of DNA and RNA, as well as modified forms that cannot readily be classified as either DNA or RNA. Likewise, a double stranded compound may be DNA:DNA, DNA:RNA or RNA:RNA, and any one strand may also include a mixture of DNA and RNA, as well as modified forms that cannot readily be classified as either DNA or RNA. A nucleic acid compound may include any of a variety of modifications, including one or modifications to the backbone (the sugar-phosphate portion in a natural nucleic acid, including internucleotide linkages) or the base portion (the purine or pyrimidine portion of a natural nucleic acid). An antisense nucleic acid compound will preferably have a length of about 15 to about 30 nucleotides and will often contain one or more modifications to improve characteristics such as stability in the serum, in a cell or in a place where the compound is likely to be delivered, such as the stomach in the case of orally delivered compounds and the lung for inhaled compounds. In the case of an RNAi construct, the strand complementary to the target transcript will generally be RNA or modifications thereof. The other strand may be RNA, DNA or any other variation. The duplex portion of double stranded or single stranded "hairpin" RNAi construct will preferably have a length of 18 to 40 nucleotides in length and optionally about 21 to 23 nucleotides in length, so long as it serves as a Dicer substrate. Catalytic or enzymatic nucleic acids may be ribozymes or DNA enzymes and may also contain modified forms. Nucleic acid compounds may inhibit expression of the target by about 50%, 75%, 90% or more when contacted with cells under physiological conditions and at a concentration where a nonsense or sense control has little or no effect. Preferred concentrations for testing the effect of nucleic acid compounds are 1, 5 and 10 micromolar. Nucleic acid compounds may also be tested for effects on, for example, angiogenesis.

Nucleic acids encoding DAN polypeptides, including variants of wild type DAN, and those encoding fusion proteins containing DAN proteins may be generated and characterized as described above with respect to nucleic acids encoding ALK1 ECD proteins.

4. Antibodies

Another aspect of the disclosure pertains to an antibody reactive with an extracellular portion of an ALK1 polypeptide, preferably antibodies that are specifically reactive with ALK1 polypeptide. In a preferred embodiment, such antibody may interfere with ALK1 binding to a ligand such as GDF5, GDF6, GDF7 BMP-9 or BMP-10—it will be understood that an antibody against a ligand of ALK1 should bind to the mature, processed form of the relevant protein. The disclosure also provides antibodies that bind to GDF5, GDF6, GDF7, BMP9 and/or BMP10 and inhibit ALK1 binding to such ligands. Preferred antibodies will exhibit an anti-angiogenic activity in a bioassay, such as a CAM assay or corneal micropocket assay (see above). A preferred anti-BMP9 antibody is described in Example 10, below. In certain embodiments, an antibody that inhibits both BMP9 and BMP10 may be desirable; such an antibody may inhibit both ligands in an ALK-1 binding assay, in an angiogenesis assay (e.g. HUVEC tube forming assay, CAM assay, Matrigel assay, or other such assays described herein).

The term "antibody" as used herein is intended to include whole antibodies, e.g., of any isotype (IgG, IgA, IgM, IgE, etc), and includes fragments or domains of immunoglobulins which are reactive with a selected antigen. Antibodies can be fragmented using conventional techniques and the fragments screened for utility and/or interaction with a specific epitope of interest. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The term antibody also includes polyclonal, monoclonal, or other purified preparations of antibodies and recombinant antibodies. The term "recombinant antibody", means an antibody, or antigen binding domain of an immunoglobulin, expressed from a nucleic acid that has been constructed using the techniques of molecular biology, such as a humanized antibody or a fully human antibody developed from a single chain antibody. Single domain and single chain antibodies are also included within the term "recombinant antibody".

Antibodies may be generated by any of the various methods known in the art, including administration of antigen to an animal, administration of antigen to an animal that carries human immunoglobulin genes, or screening with an antigen against a library of antibodies (often single chain antibodies or antibody domains). Once antigen binding activity is detected, the relevant portions of the protein may be grafted into other antibody frameworks, including full-length IgG frameworks. For example, by using immunogens derived from an ALK1 polypeptide or an ALK1 ligand (e.g., BMP9 or BMP10, or an immunogen common to both BMP9 and BMP10), anti-protein/anti-peptide antisera or monoclonal antibodies can be made by standard protocols (See, for example, Antibodies: A Laboratory Manual ed. by Harlow and Lane (Cold Spring Harbor Press: 1988)). As shown in FIG. 19, BMP9 and BMP10 have considerable amino acid identity, and therefore, each protein may be used as an immunogen to generate antibodies that can cross-react with both BMP9 and BMP10. Fragments of highly similar sequence may also be used as immunogens. A mammal, such as a mouse, a hamster or rabbit can be immunized with an immunogenic form of the peptide (e.g., a ALK1 polypeptide or an antigenic fragment which is capable of eliciting an antibody response, or a fusion protein). Techniques for conferring immunogenicity on a protein or peptide include conjugation to carriers or other techniques well known in the art. An immunogenic portion (preferably an extracellular portion) of an ALK1 polypeptide or an ALK1 ligand such as BMP9 or BMP10 can be administered in the presence of adjuvant. The progress of immunization can be monitored by detection of antibody titers in plasma or serum. Standard ELISA or other immunoassays can be used with the immunogen as antigen to assess the levels of antibodies.

Following immunization of an animal with an antigenic preparation of an ALK1 polypeptide or ligand polypeptide (e.g., BMP9 or BMP10), anti-ALK1 or anti-ligand antisera can be obtained and, if desired, polyclonal antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with a mammalian ALK1 polypeptide of the present disclosure or ligands such as BMP9 or BMP10 and monoclonal antibodies isolated from a culture comprising such hybridoma cells. Antibodies with specificity for both BMP9 and BMP10 may be selected from hybridomas that are obtained from animals inoculated with either BMP9 or BMP10 alone.

The term antibody as used herein is intended to include fragments thereof which are also specifically reactive with one of the subject ALK1 polypeptides or ALK1 ligand polypeptides or a combination of target antigens (e.g., BMP9 and BMP10). Antibodies can be fragmented using conventional techniques and the fragments screened for utility in the same manner as described above for whole antibodies. For example, $F(ab)_2$ fragments can be generated by treating antibody with pepsin. The resulting $F(ab)_2$ fragment can be treated to reduce disulfide bridges to produce Fab fragments. The antibody of the present disclosure is further intended to include bispecific, single-chain, and chimeric and humanized molecules having affinity for an ALK1 polypeptide conferred by at least one CDR region of the antibody. In preferred embodiments, the antibody further comprises a label attached thereto and is able to be detected, (e.g., the label can be a radioisotope, fluorescent compound, enzyme or enzyme co-factor).

In certain preferred embodiments, an antibody of the disclosure is a recombinant antibody, particularly a humanized monoclonal antibody or a fully human recombinant antibody.

The adjective "specifically reactive with" as used in reference to an antibody is intended to mean, as is generally understood in the art, that the antibody is sufficiently selective between the antigen of interest (e.g. an ALK1 polypeptide or an ALK1 ligand) and other antigens that are not of interest that the antibody is useful for, at minimum, detecting the presence of the antigen of interest in a particular type of biological sample. In certain methods employing the antibody, a higher degree of specificity in binding may be desirable. For example, an antibody for use in detecting a low abundance protein of interest in the presence of one or more very high abundance protein that are not of interest may perform better if it has a higher degree of selectivity between the antigen of interest and other cross-reactants. Monoclonal antibodies generally have a greater tendency (as compared to polyclonal antibodies) to discriminate effectively between the desired antigens and cross-reacting polypeptides. In addition, an antibody that is effective at selectively identifying an antigen of interest in one type of biological sample (e.g. a stool sample) may not be as effective for selectively identifying the same antigen in a different type of biological sample (e.g. a blood sample). Likewise, an antibody that is effective at identifying an antigen of interest in a purified protein preparation that is devoid of other biological contaminants may not be as effective at identifying an antigen of interest in a crude biological sample, such as a blood or urine sample. Accordingly, in preferred embodiments, the application provides antibodies that have demonstrated specificity for an antigen of interest in a sample type that is likely to be the sample type of choice for use of the antibody.

One characteristic that influences the specificity of an antibody:antigen interaction is the affinity of the antibody for the antigen. Although the desired specificity may be reached with a range of different affinities, generally preferred antibodies will have an affinity (a dissociation constant) of about $10^{-6}$, $10^{-7}$, $10^{-8}$, $10^{-9}$ or less. Given the apparently low binding affinity of TGFβ for ALK1, it is expected that many anti-ALK1 antibodies will inhibit TGFβ binding. However, the GDF5,6,7 group of ligands bind with a $K_D$ of approximately $5\times10^{-8}$ M and the BMP9,10 ligands bind with a $K_D$ of approximately $1\times10^{-10}$ M. Thus, antibodies of appropriate affinity may be selected to interfere with the signaling activities of these ligands.

In addition, the techniques used to screen antibodies in order to identify a desirable antibody may influence the properties of the antibody obtained. For example, an antibody to be used for certain therapeutic purposes will preferably be able to target a particular cell type. Accordingly, to obtain antibodies of this type, it may be desirable to screen for antibodies that bind to cells that express the antigen of interest (e.g. by fluorescence activated cell sorting). Likewise, if an antibody is to be used for binding an antigen in solution, it may be desirable to test solution binding. A variety of different techniques are available for testing antibody:antigen interactions to identify particularly desirable antibodies. Such techniques include ELISAs, surface plasmon resonance binding assays (e.g. the Biacore binding assay, Bia-core AB, Uppsala, Sweden), sandwich assays (e.g. the paramagnetic bead system of IGEN International, Inc., Gaithersburg, Md.), western blots, immunoprecipitation assays and immunohistochemistry.

In a preferred embodiment, an antibody disclosed herein is an antibody that binds to the mature portion of human BMP9, the amino acid sequence of which is shown below:

```
                                        (SEQ ID NO: 12)
RS AGAGSHCQKT SLRVNFEDIG WDSWIIAPKE YEAYECKGGC FFPLADDVTP TKHAIVQTLV

HLKFPTKVGK ACCVPTKLSP ISVLYKDDMG VPTLKYHYEG MSVAECGCR
```

In an additional embodiment, an antibody disclosed herein is an antibody that binds to the mature portion of human BMP10, the amino acid sequence of which is shown below:

```
                                   (SEQ ID NO: 13)
NAKG NYCKRTPLYI DFKEIGWDSW IIAPPGYEAY ECRGVCNYPL

AEHLTPTKHA IIQALVHLKN SQKASKACCV PTKLEPISIL YLDKGVVTYK FKYEGMAVSE

CGCR
```

Additionally, non-antibody proteins that bind to BMP9 or BMP10 may be generated by selection from libraries. A wide variety of technologies are available for selecting random peptides, as well as framework based proteins, that bind to a particular ligand. In general, an approach to identifying a useful non-antibody protein will involve screening or selecting from a library those proteins that bind to BMP9 and/or BMP10 or inhibit a BMP9 or BMP10 activity, such as receptor (e.g., ALK1) binding or cellular signaling (e.g, SMAD 1/5 signaling).

5. Alterations in Antibodies and Fc-Fusion Proteins

The application further provides antibodies, ALK1-Fc fusion proteins and DAN-Fc fusion proteins with engineered or variant Fc regions. Such antibodies and Fc fusion proteins may be useful, for example, in modulating effector functions, such as, antigen-dependent cytotoxicity (ADCC) and complement-dependent cytotoxicity (CDC). Additionally, the modifications may improve the stability of the antibodies and Fc fusion proteins. Amino acid sequence variants of the antibodies and Fc fusion proteins are prepared by introducing appropriate nucleotide changes into the DNA, or by peptide synthesis. Such variants include, for example, deletions from, and/or insertions into and/or substitutions of, residues within the amino acid sequences of the antibodies and Fc fusion proteins disclosed herein. Any combination of deletion, insertion, and substitution is made to arrive at the final construct, provided that the final construct possesses the desired characteristics. The amino acid changes also may alter post-translational processes of the antibodies and Fc fusion proteins, such as changing the number or position of glycosylation sites.

Antibodies and Fc fusion proteins with reduced effector function may be produced by introducing changes in the amino acid sequence, including, but are not limited to, the Ala-Ala mutation described by Bluestone et al. (see WO 94/28027 and WO 98/47531; also see Xu et al. 2000 Cell Immunol 200; 16-26). Thus in certain embodiments, antibodies and Fc fusion proteins of the disclosure with mutations within the constant region including the Ala-Ala mutation may be used to reduce or abolish effector function. According to these embodiments, antibodies and Fc fusion proteins may comprise a mutation to an alanine at position 234 or a mutation to an alanine at position 235, or a combination thereof. In one embodiment, the antibody or Fc fusion protein comprises an IgG4 framework, wherein the Ala-Ala mutation would describe a mutation(s) from phenylalanine to alanine at position 234 and/or a mutation from leucine to alanine at position 235. In another embodiment, the antibody or Fc fusion protein comprises an IgG 1 framework, wherein the Ala-Ala mutation would describe a mutation(s) from leucine to alanine at position 234 and/or a mutation from leucine to alanine at position 235. The antibody or Fc fusion protein may alternatively or additionally carry other mutations, including the point mutation K322A in the CH2 domain (Hezareh et al. 2001 J Virol. 75: 12161-8).

In particular embodiments, the antibody or Fc fusion protein may be modified to either enhance or inhibit complement dependent cytotoxicity (CDC). Modulated CDC activity may be achieved by introducing one or more amino acid substitutions, insertions, or deletions in an Fc region (see, e.g., U.S. Pat. No. 6,194,551). Alternatively or additionally, cysteine residue(s) may be introduced in the Fc region, thereby allowing interchain disulfide bond formation in this region. The homodimeric antibody thus generated may have improved or reduced internalization capability and/or increased or decreased complement-mediated cell killing. See Caron et al., J. Exp Med. 176:1191-1195 (1992) and Shopes, B. J. Immunol. 148:2918-2922 (1992), WO99/51642, Duncan & Winter Nature 322: 738-40 (1988); U.S. Pat. Nos. 5,648,260; 5,624,821; and WO94/29351.

6. Methods and Compositions for Modulating Angiogenesis and Treating Certain Disorders The disclosure provides methods of inhibiting angiogenesis in a mammal by administering to a subject an effective amount of a an ALK1 ECD polypeptide, such as an ALK1-Fc fusion protein, a DAN protein, such as a DAN-Fc fusion protein, or an antibody disclosed herein, such as an antibody against GDF5, GDF6, GDF7, BMP9, BMP10, or the ECD of ALK1, or nucleic acid antagonists (e.g., antisense or siRNA) of any of the foregoing hereafter collectively referred to as “therapeutic agents”. The data presented indicate specifically that the anti-angiogenic therapeutic agents disclosed herein may be used to inhibit angiogenesis in the eye of a mammal. It is expected that these therapeutic agents will also be useful in inhibiting angiogenesis in bones and joints, and in tumors, particularly tumors associated with bones and joints.

Angiogenesis associated diseases include, but are not limited to, angiogenesis-dependent cancer, including, for example, solid tumors, blood born tumors such as leukemias, and tumor metastases; benign tumors, for example hemangiomas, acoustic neuromas, neurofibromas, trachomas, and pyogenic granulomas; rheumatoid arthritis; psoriasis; rubeosis; Osler-Webber Syndrome; myocardial angiogenesis; plaque neovascularization; telangiectasia; hemophiliac joints; and angiofibroma.

In particular, polypeptide therapeutic agents of the present disclosure are useful for treating or preventing a cancer (tumor), and particularly such cancers as are known to rely on angiogenic processes to support growth. Unlike most anti-angiogenic agents, ALK1 ECD polypeptides affect angiogenesis that is stimulated by multiple factors. This is highly relevant in cancers, where a cancer will frequently acquire multiple factors that support tumor angiogenesis. Thus, the therapeutic agents disclosed herein will be particularly effective in treating tumors that are resistant to treatment with a drug that targets a single angiogenic factor (e.g., bevacizumab, which targets VEGF). As demonstrated herein, an ALK1-Fc fusion protein is effective in reducing the pathological effects of melanoma, lung cancer and multiple myeloma. Multiple myeloma is widely recognized as a cancer that includes a significant angiogenic component. Accordingly, it is expected that ALK1-Fc fusion proteins and other therapeutic agents disclosed herein will be useful in treating multiple myeloma and other tumors associated with the bone. As demonstrated herein, therapeutic agents disclosed herein may be used to ameliorate the bone damage associated with multiple myeloma, and therefore may be used to ameliorate bone damage associated with bone metastases of other tumors, such as breast or prostate tumors. As noted herein, the GDF5-7 ligands are highly expressed in bone, and, while not wishing to be limited to any particular mechanism, interference with these ligands may disrupt processes that are required for tumor development in bone.

In certain embodiments of such methods, one or more polypeptide therapeutic agents can be administered, together (simultaneously) or at different times (sequentially). In addition, polypeptide therapeutic agents can be administered with another type of compounds for treating cancer or for inhibiting angiogenesis.

In certain embodiments, the subject methods of the disclosure can be used alone. Alternatively, the subject methods may be used in combination with other conventional anti-cancer therapeutic approaches directed to treatment or prevention of proliferative disorders (e.g., tumor). For example, such methods can be used in prophylactic cancer prevention, prevention of cancer recurrence and metastases after surgery, and as an adjuvant of other conventional cancer therapy. The present disclosure recognizes that the effectiveness of conventional cancer therapies (e.g., chemotherapy, radiation therapy, phototherapy, immunotherapy, and surgery) can be enhanced through the use of a subject polypeptide therapeutic agent.

A wide array of conventional compounds have been shown to have anti-neoplastic activities. These compounds have been used as pharmaceutical agents in chemotherapy to shrink solid tumors, prevent metastases and further growth, or decrease the number of malignant cells in leukemic or bone marrow malignancies. Although chemotherapy has been effective in treating various types of malignancies, many anti-neoplastic compounds induce undesirable side effects. It has been shown that when two or more different treatments are combined, the treatments may work synergistically and allow reduction of dosage of each of the treatments, thereby reducing the detrimental side effects exerted by each compound at higher dosages. In other instances, malignancies that are refractory to a treatment may respond to a combination therapy of two or more different treatments.

When a polypeptide therapeutic agent disclosed herein is administered in combination with another conventional anti-neoplastic agent, either concomitantly or sequentially, such therapeutic agent may enhance the therapeutic effect of the anti-neoplastic agent or overcome cellular resistance to such anti-neoplastic agent. This allows decrease of dosage of an anti-neoplastic agent, thereby reducing the undesirable side effects, or restores the effectiveness of an anti-neoplastic agent in resistant cells.

According to the present disclosure, the antiangiogenic agents described herein may be used in combination with other compositions and procedures for the treatment of diseases. For example, a tumor may be treated conventionally with surgery, radiation or chemotherapy combined with the ALK1 or ALK1 ligand antagonist and then the antagonist may be subsequently administered to the patient to extend the dormancy of micrometastases and to stabilize any residual primary tumor.

Angiogenesis-inhibiting agents can also be given prophylactically to individuals known to be at high risk for developing new or re-current cancers. Accordingly, an aspect of the disclosure encompasses methods for prophylactic prevention of cancer in a subject, comprising administrating to the subject an effective amount of an ALK1 or ALK1 ligand antagonist and/or a derivative thereof, or another angiogenesis-inhibiting agent of the present disclosure.

As demonstrated herein, ALK1-Fc is effective for diminishing the phenotype of a murine model of rheumatoid arthritis. Accordingly, therapeutic agents disclosed herein may be used for the treatment of rheumatoid arthritis and other type of bone or joint inflammation.

Certain normal physiological processes are also associated with angiogenesis, for example, ovulation, menstruation, and placentation. The angiogenesis inhibiting proteins of the present disclosure are useful in the treatment of disease of excessive or abnormal stimulation of endothelial cells. These diseases include, but are not limited to, intestinal adhesions, atherosclerosis, scleroderma, and hypertrophic scars, i.e., keloids. They are also useful in the treatment of diseases that have angiogenesis as a pathologic consequence such as cat scratch disease (*Rochele minalia quintosa*) and ulcers (*Helicobacter pylori*).

General angiogenesis inhibiting proteins can be used as a birth control agent by reducing or preventing uterine vascularization required for embryo implantation. Thus, the present disclosure provides an effective birth control method when an amount of the inhibitory protein sufficient to prevent embryo implantation is administered to a female. In one aspect of the birth control method, an amount of the inhibiting protein sufficient to block embryo implantation is administered before or after intercourse and fertilization have occurred, thus providing an effective method of birth control, possibly a "morning after" method. While not wanting to be bound by this statement, it is believed that inhibition of vascularization of the uterine endometrium interferes with implantation of the blastocyst. Similar inhibition of vascularization of the mucosa of the uterine tube interferes with implantation of the blastocyst, preventing occurrence of a tubal pregnancy. Administration methods may include, but are not limited to, pills, injections (intravenous, subcutaneous, intramuscular), suppositories, vaginal sponges, vaginal tampons, and intrauterine devices. It is also believed that administration of angiogenesis inhibiting agents of the present disclosure will interfere with normal enhanced vascularization of the placenta, and also with the development of vessels within a successfully implanted blastocyst and developing embryo and fetus.

In the eye, angiogenesis is associated with, for example, diabetic retinopathy, retinopathy of prematurity, macular degeneration, corneal graft rejection, neovascular glaucoma, and retrolental fibroplasias. The therapeutic agents disclosed herein may be administered intra-ocularly or by other local administration to the eye. Furthermore, as shown in the Examples, ALK1-Fc may be administered systemically and yet have the desired effect on ocular angiogenesis.

Other diseases associated with angiogenesis in the eye include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, *Mycobacteria* infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, mariginal keratolysis, rheumatoid arthritis, systemic lupus, polyarteritis, trauma, Wegeners sarcoidosis, Scleritis, Steven's Johnson disease, periphigoid radial keratotomy, and corneal graft rejection.

sickle cell anemia, sarcoid, pseudoxanthoma elasticum, Pagets disease, vein occlusion, artery occlusion, carotid obstructive disease, chronic uveitis/vitritis, mycobacterial infections, Lyme's disease, systemic lupus erythematosis, retinopathy of prematurity, Eales disease, Bechets disease, infections causing a retinitis or choroiditis, presumed ocular histoplasmosis, Bests disease, myopia, optic pits, Stargarts disease, pars planitis, chronic retinal detachment, hyperviscosity syndromes, toxoplasmosis, trauma and post-laser complications. Other diseases include, but are not limited to, diseases associated with rubeosis (neovasculariation of the angle) and diseases caused by the abnormal proliferation of fibrovascular or fibrous tissue including all forms of proliferative vitreoretinopathy.

Conditions of the eye can be treated or prevented by, e.g., systemic, topical, intraocular injection of a therapeutic agent, or by insertion of a sustained release device that releases a therapeutic agent. A therapeutic agent may be delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically-acceptable ophthalmic vehicle may, for example, be an ointment, vegetable oil or an encapsulating material. Alternatively, the therapeutic agents of the disclosure may be injected directly into the vitreous and aqueous humour. In a further alternative, the compounds may be administered systemically, such as by intravenous infusion or injection, for treatment of the eye.

One or more therapeutic agents can be administered. The methods of the disclosure also include co-administration with other medicaments that are used to treat conditions of the eye. When administering more than one agent or a combination of agents and medicaments, administration can occur simultaneously or sequentially in time. The therapeutic agents and/or medicaments may be administered by different routes of administration or by the same route of administration. In one embodiment, a therapeutic agent and a medicament are administered together in an ophthalmic pharmaceutical formulation.

In one embodiment, a therapeutic agent is used to treat a disease associated with angiogenesis in the eye by concurrent administration with other medicaments that act to block angiogenesis by pharmacological mechanisms. Medicaments that can be concurrently administered with a therapeutic agent of the disclosure include, but are not limited to, pegaptanib (Macugen™), ranibizumab (Lucentis™), squalamine lactate (Evizon™), heparinase, and glucocorticoids (e.g. Triamcinolone). In one embodiment, a method is provided to treat a disease associated with angiogenesis is treated by administering an ophthalmic pharmaceutical formulation containing at least one therapeutic agent disclosed herein and at least one of the following medicaments: pegaptanib (Macugen™), ranibizumab (Lucentis™), squalamine lactate (Evizon™), heparinase, and glucocorticoids (e.g. Triamcinolone).

7. Formulations and Effective Doses

The therapeutic agents described herein may be formulated into pharmaceutical compositions. Pharmaceutical compositions for use in accordance with the present disclosure may be formulated in conventional manner using one or more physiologically acceptable carriers or excipients. Such formulations will generally be substantially pyrogen free, in compliance with most regulatory requirements.

In certain embodiments, the therapeutic method of the disclosure includes administering the composition systemically, or locally as an implant or device. When administered, the therapeutic composition for use in this disclosure is in a pyrogen-free, physiologically acceptable form. Therapeutically useful agents other than the ALK1 signaling antagonists which may also optionally be included in the composition as described above, may be administered simultaneously or sequentially with the subject compounds (e.g., ALK1 ECD polypeptides or any of the antibodies disclosed herein) in the methods disclosed herein.

Typically, protein therapeutic agents disclosed herein will be administered parentally, and particularly intravenously or subcutaneously. Pharmaceutical compositions suitable for parenteral administration may comprise one or more ALK1 ECD polypeptides or other antibodies in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

In one embodiment, the antibodies and ALK1 ECD proteins disclosed herein are administered in an ophthalmic pharmaceutical formulation. In some embodiments, the ophthalmic pharmaceutical formulation is a sterile aqueous solution, preferable of suitable concentration for injection, or a salve or ointment. Such salves or ointments typically comprise one or more antibodies or ALK1 ECD proteins disclosed herein dissolved or suspended in a sterile pharmaceutically acceptable salve or ointment base, such as a mineral oil-white petrolatum base. In salve or ointment compositions, anhydrous lanolin may also be included in the formulation. Thimerosal or chlorobutanol are also preferably added to such ointment compositions as antimicrobial agents. In one embodiment, the sterile aqueous solution is as described in U.S. Pat. No. 6,071,958.

The disclosure provides formulations that may be varied to include acids and bases to adjust the pH; and buffering agents to keep the pH within a narrow range. Additional medicaments may be added to the formulation. These include, but are not limited to, pegaptanib, heparinase, ranibizumab, or glucocorticoids. The ophthalmic pharmaceutical formulation according to the disclosure is prepared by aseptic manipulation, or sterilization is performed at a suitable stage of preparation.

The compositions and formulations may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

EXAMPLES

Example 1

Expression of ALK1-Fc Fusion Proteins

Applicants constructed a soluble ALK1 fusion protein that has the extracellular domain of human ALK1 fused to a human Fc or mouse ALK1 fused to a murine Fc domain with a minimal linker in between. The constructs are referred to as hALK1-Fc and mALK1-Fc, respectively.

hALK1-Fc is shown as purified from CHO cell lines in FIG. 3 (SEQ ID NO: 3). Notably, while the conventional C-terminus of the extracellular domain of human ALK1 protein is amino acid 118 of SEQ ID NO:1, we have determined that it is desirable to avoid having a domain that ends at a glutamine residue. Accordingly, the portion of SEQ ID NO:3 that derives from human ALK1 incorporates two residues c-terminal to Q118, a leucine and an alanine. The disclosure therefore provides ALK1 ECD polypeptides (including Fc fusion proteins) having a c-terminus of the ALK1 derived sequence that is anywhere from 1 to 5 amino acids upstream (113-117 relative to SEQ ID NO:1) or downstream (119-123) of Q118.

The hALK1-Fc and mALK1-Fc proteins were expressed in CHO cell lines. Three different leader sequences were considered:

```
(i) Honey bee mellitin (HBML):
MKFLVNVALVFMVVYISYIYA        (SEQ ID NO: 7)

(ii) Tissue Plasminogen Activator (TPA):
MDAMKRGLCCVLLLCGAVFVSP       (SEQ ID NO: 8)

(iii) Native:
MTLGSPRKGLLMLLMALVTQG.       (SEQ ID NO: 9)
```

The selected form employs the TPA leader and has the unprocessed amino acid sequence shown in FIG. 4 (SEQ ID NO:5).

This polypeptide is encoded by the nucleic acid sequence shown in FIG. 4 (SEQ ID NO:4).

Purification can be achieved by a series of column chromatography steps, including, for example, three or more of the following, in any order: protein A chromatography, Q sepharose chromatography, phenylsepharose chromatography, size exclusion chromatography, and cation exchange chromatography. The purification can be completed with viral filtration and buffer exchange. The hALK1-Fc protein was purified to a purity of >98% as determined by size exclusion chromatography and >95% as determined by SDS PAGE.

In the course of protein production and purification, we observed that hALK1-Fc tends to be expressed in a mixture of dimers and higher order aggregates which, while appearing pure under denaturing, reducing conditions (e.g., reducing SDS-PAGE), are problematic for administration to a patient. The aggregates may be immunogenic or poorly bioavailable, and because of their heterogeneity, these aggregates make it difficult to characterize the pharmaceutical preparation at a level that is desirable for drug development. Thus, various approaches were tested to reduce the amount of aggregate in final preparations.

In one approach, a number of different cell culture media were tested. IS CHO-CD (Cat. No. 91119, Irvine Scientific, Santa Ana, Calif.) showed a remarkable reduction in the production of aggregated products, while maintaining high level production of the hALK1-Fc. Additionally, elution of the material from a hydrophobic interaction column (e.g., phenylsepharose) at a pH of 8.0 resulted in further resolution of the aggregated product. The resulting material is comprised of greater than 99% dimers. A comparison to an ALK1-Fc fusion protein sold by R&D Systems (cat. no. 370-AL, Minneapolis, Minn.) shows that this protein, produced in NSO cells, is 84% dimers, with the remaining protein appearing as high molecular weight species by size exclusion chromatography. A comparison of the sizing column profile for the preparations is shown in FIG. 11. Having identified aggregate formation as a significant problem in ALK1-Fc production, it is expected that other approaches may be developed, including approaches that involve additional purification steps (although such approaches may result in lower yield of purified protein).

Example 2

Identification of ALK1-Fc Ligands

ALK1 is a type 1 receptor for ligands of the TGFβ family. Multiple members of the TGFβ family were tested for binding to a human ALK1-Fc fusion protein, using a Biacore™ system. TGFβ itself, GDF5, GDF11, BMP2 and BMP4 all failed to show substantial binding to the hALK1-Fc protein, while BMP2 and BMP4 showed only limited binding. In contrast, GDF5 and GDF7 displayed significant binding, with $K_D$ values of approximately $5\times10^{-8}$ M in both cases. Based on the structural similarity of GDF5 and GDF7 to GDF6, it is expected that GDF6 will bind the fusion protein with similar affinity. The highest binding affinity to hALK1-Fc was observed for BMP9, with $K_D$ values ranging from $1\times10^{-10}$ to $2\times10^{-9}$, and BMP10, with a $K_D$ of approximately $3\times10^{-9}$.

Example 3

Characterization of ALK1-Fc and Anti-ALK1 Antibody Effects on Endothelial Cells Using a luciferase reporter construct under the control of four sequential consensus SBE sites (SBE4-luc), which are responsive to Smad1/5/8-mediated signaling, we measured BMP-9 mediated activity in the presence and absence of hALK1-Fc drug or neutralizing ALK1 specific monoclonal antibody in HMVEC cells. HMVEC cells were stimulated with rhBMP-9 (50 ng/ml), which induced Smad1/5/8-mediated transcriptional activation, evidenced here by the increase in SBE4-luc modulated transcriptional upregulation. When added, the hALK1-Fc compound (10 μg/ml) or antibody (10 μg/ml) diminished this transcriptional response, each by nearly 60%, indicating that the presence of ALK1-Fc significantly reduces BMP9 signaling, and moreover, that the BMP9 signaling is related to ALK1 activity.

Activation of SMAD phosphorylation is commonly used to assay activation of upstream activin receptors. ALK1 is known to modulate phosphorylation of SMAD proteins 1,5 and 8 upon activation by its ligand. Here, we added rhBMP-9 (50 ng/ml) to initiate SMAD phosphorylation in HUVEC cells, a human endothelial cell line which innately expresses ALK1 receptor, over a timecourse of 30 minutes. Phosphorylation of SMAD 1/5/8 was seen 5 minutes after treatment of cells with ligand and phosphorylation was maintained for the entirety of the 30 minute period. In the presence of relatively low concentrations of hALK1-Fc (250 ng/ml), SMAD 1/5/8 phosphorylation was reduced, confirming that this agent inhibits Smad1/5/8 activation in endothelial cells.

In order to evaluate the angiogenic effect of ALK1-Fc in an in vitro system, we assayed the effectiveness of the compound in reducing tube formation of endothelial cells on a Matrigel substrate. This technique is commonly used to assess neovascularization, giving both rapid and highly reproducible results. Endothelial Cell Growth Supplement (ECGS) is used to induce the formation of microvessels from endothelial cells on Matrigel, and the efficacy of anti-angiogenic compounds are then gauged as a reduction of cord formation in the presence of both the drug and ECGS over an 18 hour timecourse. As expected, addition of ECGS (200 ng/ml) induced significant cord formation, as compared to the negative control (no treatment added), which indicates basal levels of endothelial cell cord formation produced on Matrigel substrate (FIG. 5). Upon addition of either hALK1-Fc (100 ng/ml) or mALK1-Fc (100 ng/ml), cord formation was visibly reduced. Final quantification of vessel length in all samples revealed that every concentration of hALK1-fc or mALK1-Fc reduced neovascularization to basal levels. Additionally, hALK1-Fc and mALK1-Fc in the presence of the strongly pro-angiogenic factor ECGS maintained strong inhibition of neovascularization demonstrating even more potent anti-angiogenic activity than the negative control endostatin (100 ng/ml).

Example 4

CAM Assays

Figure 6:
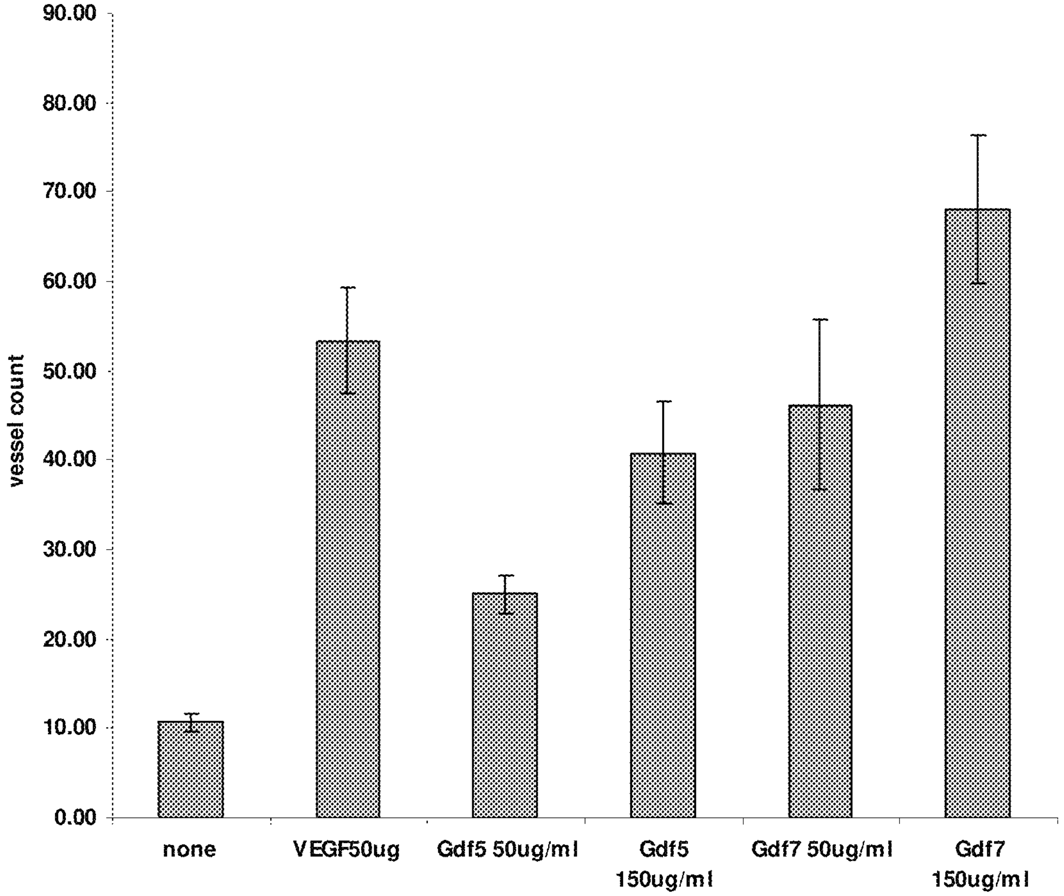
FIG. 6 shows the angiogenic effect of GDF7 in a chick chorioallantoic membrane (CAM) assay. The GDF7 effect is comparable to that of VEGF.

VEGF and FGF are well-known to stimulate angiogenesis. A CAM (chick chorioallantoic membrane) assay system was used to assess the angiogenic effects of GDF7. As shown in FIG. 6, GDF7 stimulates angiogenesis with a potency that is similar to that of VEGF. Similar results were observed with GDF5 and GDF6.

Figure 7:
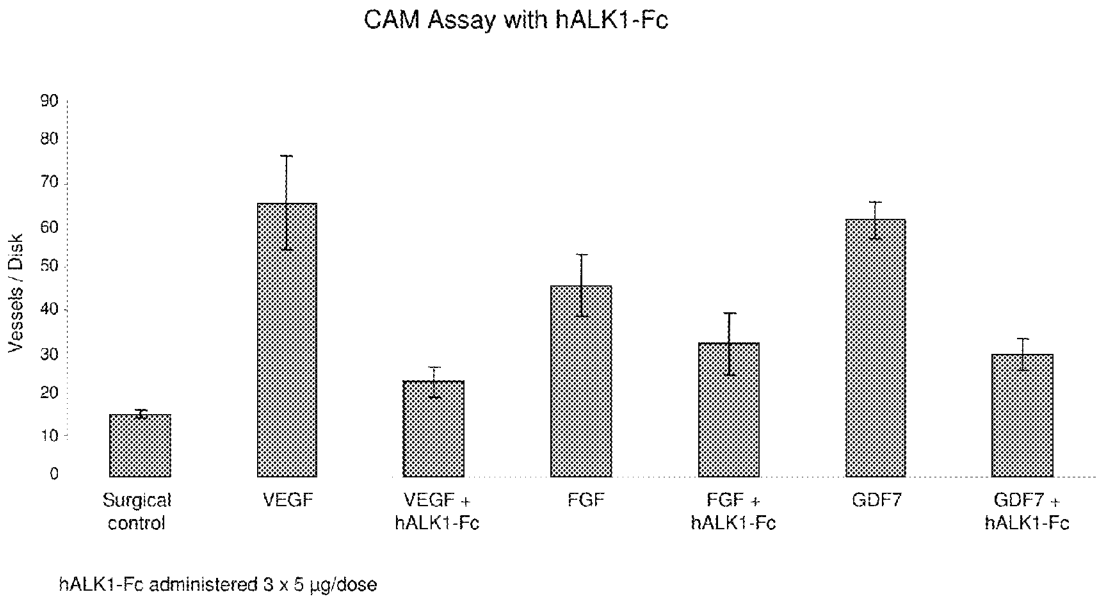
FIG. 7 shows the anti-angiogenic effect of the human ALK1-Fc fusion in the CAM assay. hALK1-Fc inhibits angiogenesis stimulated by VEGF, FGF and GDF7.

ALK1-Fc fusions were tested for anti-angiogenic activity in the CAM assay. These fusion proteins showed a potent anti-angiogenic effect on angiogenesis stimulated by VEGF, FGF and GDF7. See FIG. 7. BMP9 and PDGF showed a relatively poor capability to induce angiogenesis in this assay, but such angiogenesic effect of these factors was nonetheless inhibited by ALK1.

Figure 8:
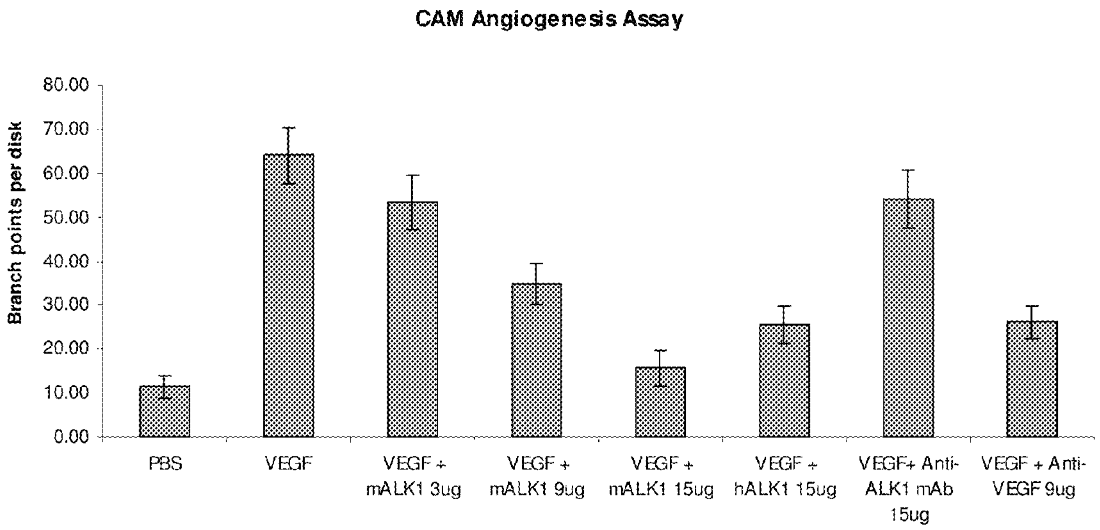
FIG. 8 shows comparative anti-angiogenic effects of murine ALK1-Fc (mALK1-Fc), hALK1-Fc, a commercially available anti-ALK1 monoclonal antibody (Anti-ALK1 mAb) and a commercially available, neutralizing anti-VEGF monoclonal antibody. The anti-angiogenic effect of the ALK1-Fc constructs is comparable to the effects of the anti-VEGF antibody.

ALK1-Fc proteins and a commercially available, anti-angiogenic anti-VEGF monoclonal antibody were compared in the CAM assay. The ALK1-Fc proteins had similar potency as compared to anti-VEGF. The anti-VEGF antibody bevacizumab is currently used in the treatment of cancer and macular degeneration in humans. See FIG. 8.

Interestingly, an anti-ALK1 antibody (R&D Systems) failed to significantly inhibit angiogenesis in this assay system. We expect that this may reflect the difference in the ALK1 sequence in different species.

Example 5

Mouse Corneal Micropocket Assay

Figure 9:
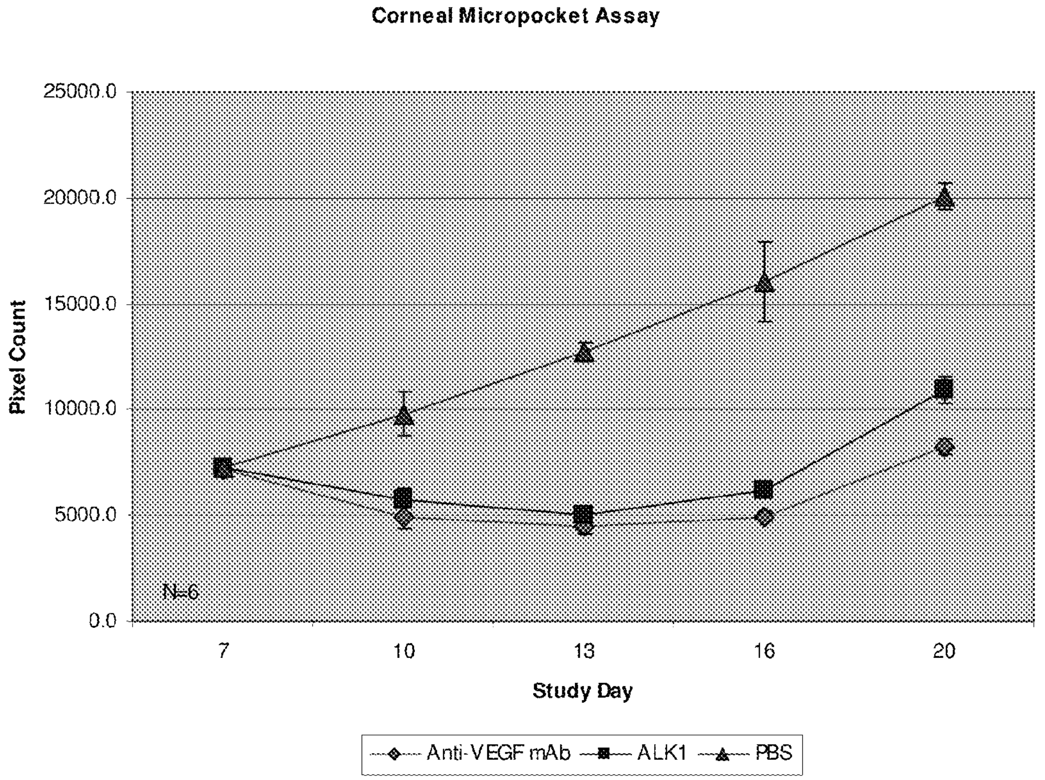
FIG. 9 shows the anti-angiogenic effects of hALK1-Fc and the anti-VEGF antibody in vivo. hALK1-Fc and anti-VEGF had comparable effects on angiogenesis in the eye as measured by the mouse corneal micropocket assay.

The mouse corneal micropocket assay was used to assess the effects of ALK1-Fc on angiogenesis in the mouse eye. hALK1-Fc, administered intraperitoneally, significantly inhibited ocular angiogenesis. As shown in FIG. 9, hALK1-Fc inhibited ocular angiogenesis to the same degree as anti-VEGF. hALK1-Fc and anti-VEGF were used at identical weight/weight dosages. Similar data were obtained when a Matrigel plug impregnated with VEGF was implanted in a non-ocular location.

These data demonstrate that high affinity ligands for ALK1 promote angiogenesis and that an ALK1-Fc fusion protein has potent anti-angiogenic activity. The ligands for ALK1 fall into two categories, with the GDF5,6,7 grouping having an intermediate affinity for ALK1 and the BMP9,10 grouping having a high affinity for ALK1.

GDF5, GDF6, and GDF7 are primarily localized to bone and joints, while BMP9 is circulated in the blood. Thus, there appears to be a pro-angiogenic system of the bones and joints that includes ALK1, GDF5, GDF6, and GDF7 and a systemic angiogenic system that includes ALK1 and BMP9 (and possibly BMP10).

Example 6

Murine Model of Rheumatoid Arthritis

Figure 10:
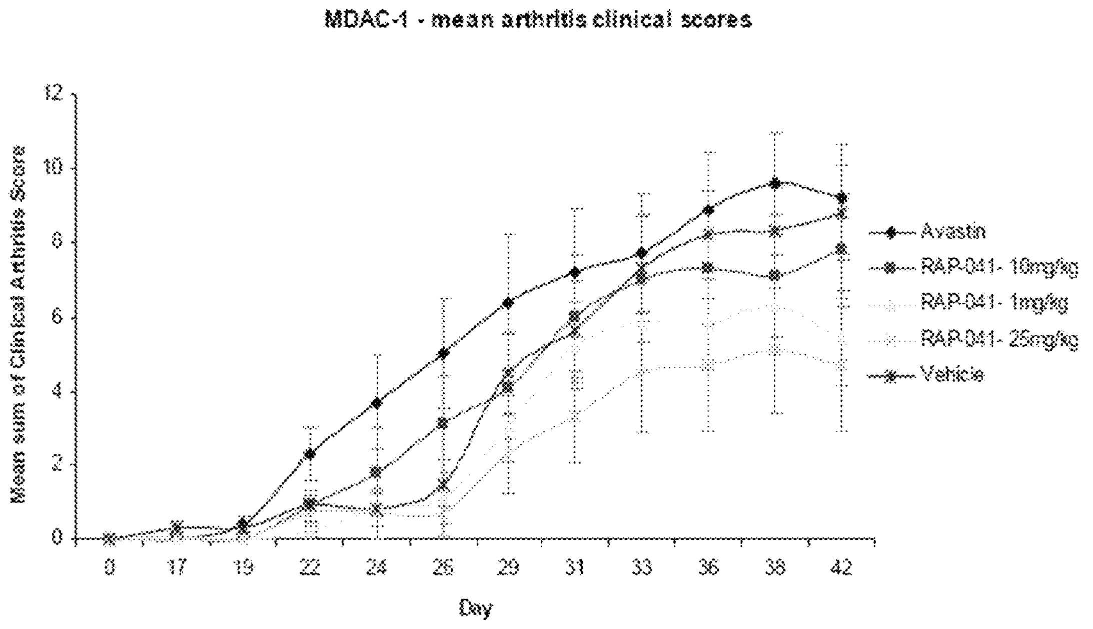
FIG. 10 shows the effects of mALK1-Fc in the murine collagen-induced arthritis (CIA) model of rheumatoid arthritis. The graph shows mean group arthritic scores determined during the 42 day observation period in the collagen-induced male DBA/1 arthritic mice. RAP-041 is mALK1-Fc. Avastin™ is the anti-VEGF antibody bevacizumab.

The murine collagen-induced arthritis model is a well-accepted model of rheumatoid arthritis. In this study, groups of 10 mice were treated with vehicle, anti-VEGF (bevacizumab—as a negative control, because bevacizumab does not inhibit murine VEGF), or doses of mALK1-Fc ("RAP-041") at 1 mg/kg, 10 mg/kg or 25 mg/kg. Following the collagen boost on day 21 arthritic scores (see FIG. 10) and paw swelling steadily increased in all groups, peaking around day 38. Mice treated with mALK1-Fc ("RAP-041") showed reduced scores for both characteristics, particularly at the highest dose (25 mg/kg), although the reduction did not achieve statistical significance. Nonetheless, a dose-related trend is apparent.

By study termination at day 42 the incidence of arthritis had reached 10/10 in the vehicle control treated mice, 9/10 in the bevacizumab treated mice, 8/10 in the mALK1-Fc at 1 mg/kg treated group and 9/10 in the mALK1-Fc 10 mg/kg treated group. In the mALK1-Fc 25 mg/kg treated group disease incidence was lower at 6/10.

Example 7

Ligand Binding Characteristics of DAN

DAN is a member of a family of secreted cystine knot proteins that inhibit BMP activity. DAN is known to bind to and antagonize GDF5. We determined that DAN also binds tightly to GDF7, but not to BMP9. Thus, we conclude that DAN inhibits the suite of bone and joint localized ligands for ALK1, and DAN is expected to be a potent antagonist of bone and joint related angiogenesis. Thus DAN may be useful in treating cancers of the bone, e.g., multiple myeloma and bone metastases, as well as rheumatoid arthritis and osteoarthritis.

Taken together, the findings disclosed in these Examples provide numerous reagents, described herein, for inhibiting angiogenesis in vivo, and particularly ocular angiogenesis. These findings also indicate that agents targeted to GDF5, GDF6, and GDF7 can be used to selectively inhibit bone and joint angiogenesis. These findings further indicate that such agents can be used to treat cancers and rheumatoid arthritis.

Example 8

ALK1-Fc Reduces Tumor Angiogenesis in a CAM Assay

Tumors, as with any tissue, have a basic nutrient and oxygen requirement. Although small tumors are capable of acquiring adequate amounts via diffusion from neighboring blood vessels, as the tumor increases in size, it must secure nutrients by recruiting and maintaining existing capillaries. In order to test the capacity of ALK1-Fc proteins to limit tumor growth through vessel inhibition, we tested varying concentrations of mALK1-Fc in a melanoma explant CAM assay. As with CAM assays described above, small windows were made in the surface of each egg through which $5\times10^5$ B16 melanoma cells were implanted. Eggs were then treated daily with 0.02 mg/ml mALK1-Fc, 0.2 mg/ml mALK1-Fc, or left untreated for a period of a week. At the end of the experiment, tumors were carefully removed, weighed and digital images were captured. Tumors originating from CAMs treated with mALK1-Fc showed a significant decrease in size as compared to untreated CAM tumors. Quantification of tumor weight demonstrated that weight of tumors treated daily with either 0.02 mg/ml or 0.2 mg/ml mALK1-Fc showed a reduction of 65% and 85% compared to the untreated CAMs. In conclusion, neovascularization and tumor growth was significantly suppressed upon addition of ALK1-Fc in a dose-responsive manner, indicating that ALK1-Fc is a powerful anti-angiogenic agent.

Example 9

Lung Cancer Experimental Model

Figure 12:
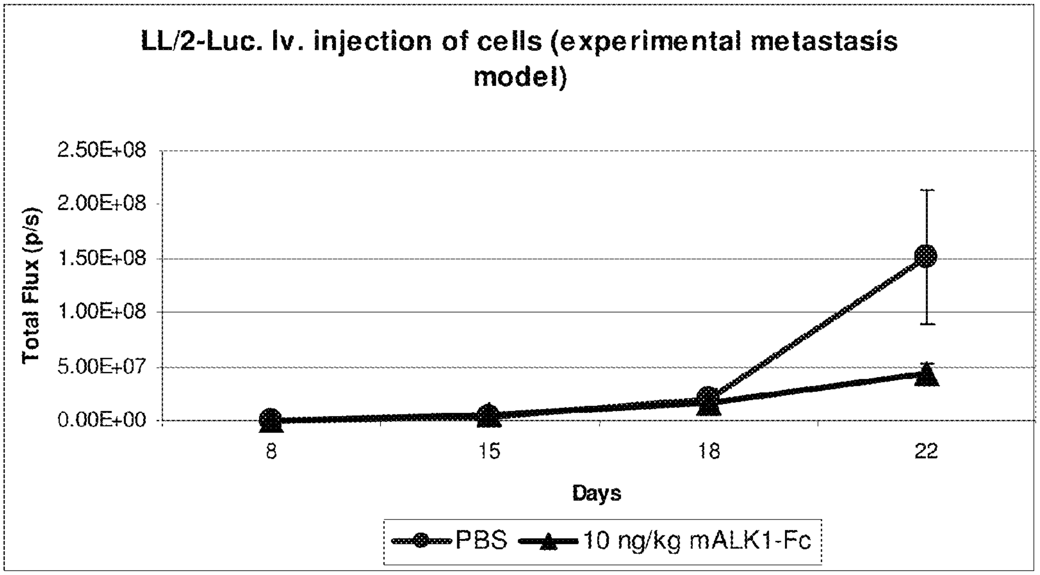
FIG. 12 shows fluorescent signal from luciferase-expressing Lewis lung cancer (LL/2-luc) cells in mice treated with PBS (circles) and mALK1-Fc (squares). Tumor cells were injected into the tail vein and treatment (PBS or 10 mg/kg mALK1-Fc IP, twice weekly) was initiated on the day of cell administration. PBS-treated mice were sacrificed on day 22 as being moribund. The treatment and control groups each consisted of seven animals (n=7).

To further confirm the effects of ALK1-Fc on tumor progression, a mouse model of lung cancer was tested. Fluorescently labeled murine Lewis lung cancer cells (LL/2-luc) were administered to albino Black 6 mice through the tail vein. On the same day, the mice began treatment with either PBS control (n=7) or 10 mg/kg mALK1-Fc (n=7) administered intraperitoneally. In-life fluorescent imaging showed substantial development of tumors localized to the lungs in the control mice, to the point that the mice became moribund and had to be sacrificed by day 22 post-implantation. By contrast, the ALK1-Fc treated mice showed a substantially delayed growth of lung tumors and exhibited 100% survival as of day 22. See FIG. 12.

These data demonstrate that ALK1-Fc has substantial effect on tumor growth in a mouse model of lung cancer and provides a survival benefit.

Example 10

BMP9 and Anti-BMP9, Effects on Angiogenesis

A CAM (chick chorioallantoic membrane) assay system was used to assess the angiogenic effects of recombinant human BMP9 (rhB9) and anti-BMP9 monoclonal antibody (mabB9) (R&D Systems, Minneapolis, Minn., Cat. No. MAB3209). This antibody is known to neutralize BMP9/ALK1 signaling. See, e.g., Scharpfenecker et al., *J Cell Sci.* 2007 Mar. 15; 120(Pt 6):964-72; David et al. *Blood* March 1; 109(5):1953-61; 2007; David et al., *Circ Res.* 2008 Apr. 25; 102(8):914-22.

Figure 13:
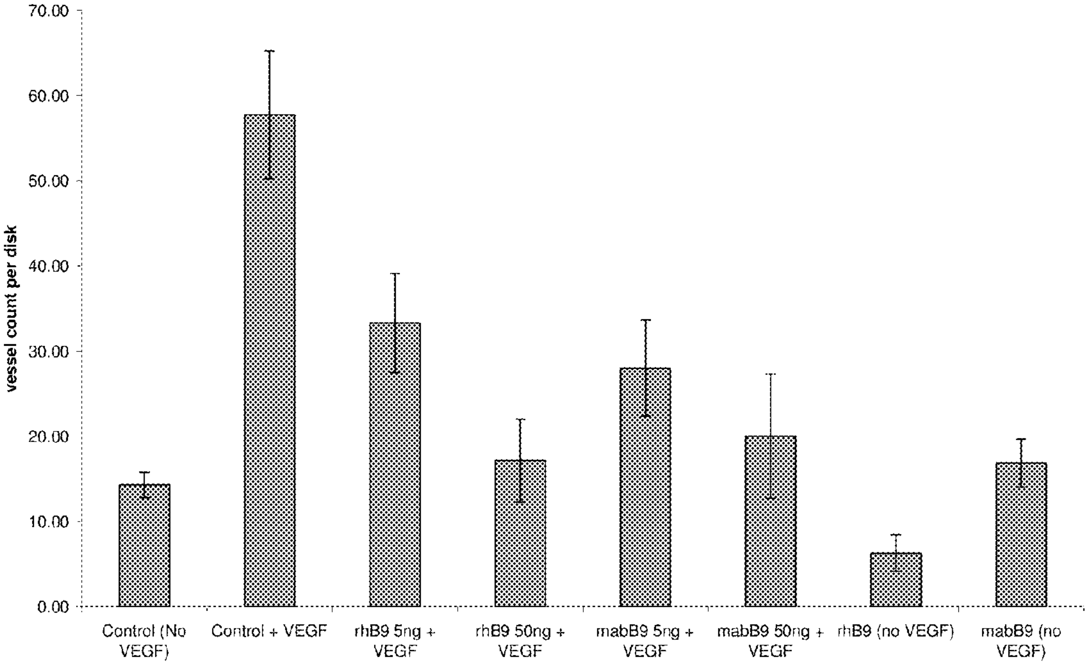
FIG. 13 shows the effect of recombinant human BMP9 ("rhB9") and a commercially available anti-BMP9 monoclonal antibody ("mabB9") on VEGF-mediated angiogenesis in the CAM assay. Intriguingly, both BMP9 and anti-BMP9 treatment inhibit VEGF-mediated angiogenesis.

Neither BMP9 nor anti-BMP9 had a substantial effect on angiogenesis in the absence of exogenous VEGF, probably because the lack of angiogenesis in the absence of exogenous VEGF decreases the sensitivity of the assay. See FIG. 13, right hand columns. In the absence of VEGF, both proteins were used at the 50 ng dosed 1×/day on days 1 and 3 in the 5-day cycle. However, in the presence of VEGF, both BMP9 and its antibody had a substantial anti-angiogenic effect. See FIG. 13. These data are consistent with data from Scharpfenecker et al., with respect to BMP9 and VEGF in combination, and are also consistent with the conclusions of Scharpfenecker et al. and David et al. with respect to the anti-angiogenic effects of BMP9 itself. However, the effects of the anti-BMP9 antibody are in remarkable contrast to the published literature. Based on these data, we hypothesize that optimal or physiological levels of BMP9 may be needed for proper angiogenesis, and that either an excess or deficiency in BMP9 will inhibit angiogenesis.

Intriguingly, the effects of the anti-BMP9 antibody are consistent with data presented here showing that ALK1-Fc (which is an alternative BMP9 antagonist) also inhibits angiogenesis. Thus, these data demonstrate that ALK1-Fc and anti-BMP9 each have anti-angiogenic effects, and that anti-BMP9 antibody is likely to be useful in the treatment of angiogenic disorders, such as tumors, rheumatoid arthritis and ocular disorders, in much the same way that ALK1-Fc is shown to be.

Given the anti-angiogenic activity of the MAB3209, we propose that this murine monoclonal antibody could be humanized to provide a therapeutic agent for use in humans. The antibody may be humanized by a variety of art-recognized techniques, including chimerization, CDR-grafting, resurfacing, back mutations, superhumanization, human string content optimization, and empirical methods, such as FR library generation and selection, FR shuffling and humaneering. See, e.g, Almagro and Fransson, *Frontiers in Biosciences,* 13: 1619-1633, 2008.

Example 11

Effects of ALK1-Fc Fusion Protein on Breast Cancer Tumor Models mALK1-Fc was effective in delaying the growth of breast cancer tumor cell lines derived from both estrogen receptor positive (ER+) and estrogen receptor negative tumor cells (ER−).

The MDA-MB-231 breast cancer cell line (derived from ER− cells) was stably transfected with the luciferase gene to allow for the in vivo detection of tumor growth and potential metastasis. In this study, $1\times10^6$ MDA-MB-231-Luc cells were implanted orthotopically in the mammary fat pad of athymic nude mice (Harlan). Tumor progression was followed by bioluminescent detection using an IVIS Spectrum imaging system (Caliper Life Sciences). An increase in the luminescence (number of photons detected) corresponds to an increase in tumor burden.

Figure 14:
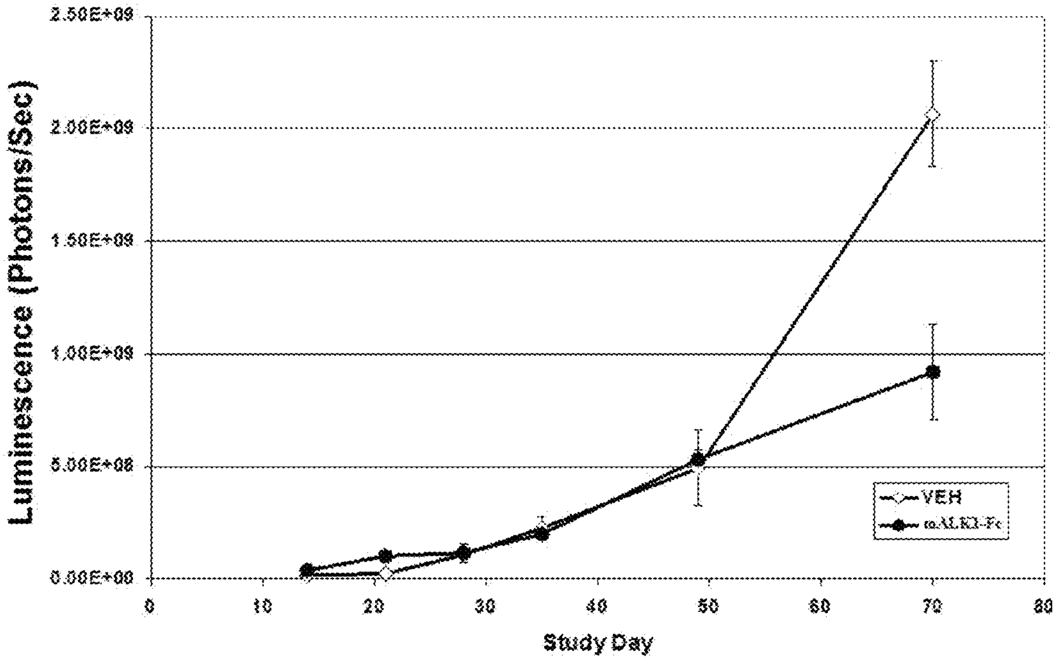
FIG. 14 shows the effects of mALK1-Fc on an orthotopic xenograft model using the MDA-MB-231 cell line, a cell line derived from ER− breast cancer cells. At a dose of 30 mg/kg, the mALK1-Fc has a significant growth-delaying effect on the xenograft tumor.

Thirty female nude mice were injected with $1\times10^6$ tumor cells into the mammary fat pad. Three days after tumor implantation the mice were treated with either vehicle control or mALK1-Fc (30 mg/kg) twice per week by subcutaneous (SC) injection. Treatment was continued and tumor progression was monitored by bioluminescent imaging for 10 weeks. mALK1-Fc treatment at 30 mg/kg slowed tumor progression as determined by bioluminescent detection when compared to vehicle treated controls (FIG. 14). Treatment with mALK1-Fc delayed, but did not reverse tumor growth in this model. This may be expected of an antiangiogenic compound in that tumors may be able to survive to a certain size before requiring new blood vessel formation to support continued growth. In a similar experiment, hALK1-Fc produced similar, if slightly lesser, effects at dose levels as low as 3 mg/kg.

Figure 15:
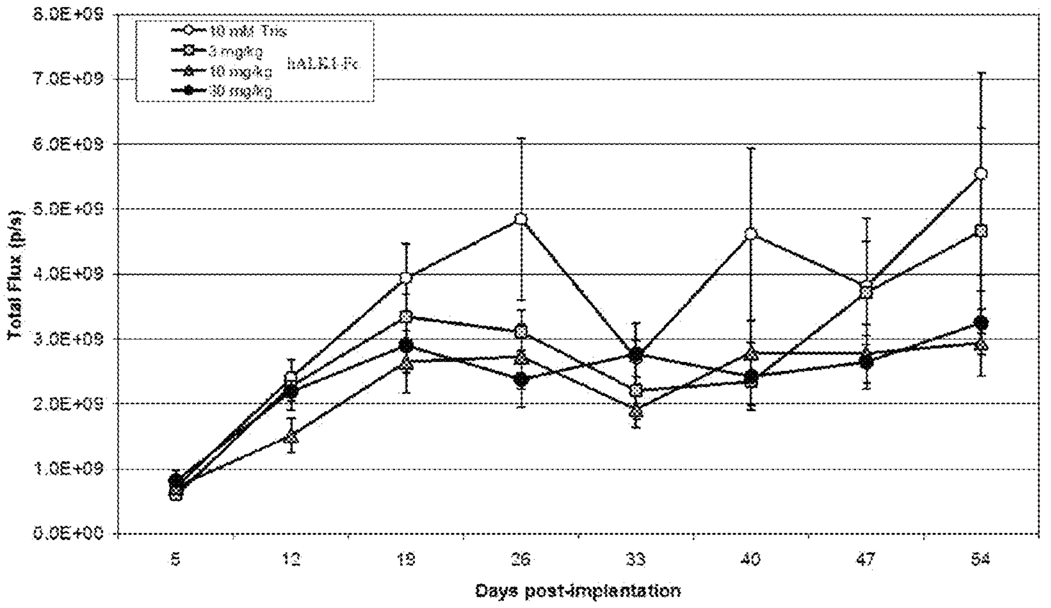
FIG. 15 shows the effects of hALK1-Fc on an orthotopic xenograft model using the MCF7 cell line, a cell line derived from ER+ breast cancer cells. At a dose of 10 or 30 mg/kg, the hALK1-Fc has a significant growth-delaying effect on the xenograft tumor.

The estrogen-receptor-positive (ER+), luciferase expressing cell line, MCF-7, was also tested in an orthotopic implantation model. In this model, female nude mice are implanted subcutaneously with a 60 day slow release pellet of 17β-estradiol. Two days following pellet implantation, $5\times10^6$ MCF-7 tumor cells were implanted into the mammary fat pad. Mice were treated twice per week with hALK1-Fc at 3, 10 and 30 mg/kg, or vehicle control, by the IP route. Tumor progression was followed by bioluminescent imaging on a weekly basis with an IVIS-Spectrum imager (Caliper Life Sciences). In vehicle treated mice tumors progressed rapidly until study day 26 (FIG. 15). After day 26, there were fluctuations in tumor luminescence until the conclusion of the study at day 60 (when the estradiol pellets were depleted). These fluctuations are due to a common feature of this model in that the rapid tumor growth can exceed the angiogenic response of the host animals leading to tumor necrosis and a concomitant drop-off in luminescent signal. The remaining cells continue to grow leading to an increased signal. Mice treated with 10 or 30 mg/kg of hALK1-Fc were able to maintain tumor size at a constant level during the study, compared to vehicle-treated controls, indicating a potent effect of this molecule on tumor growth.

Example 12

Inhibition of BMP10 Signaling by hALK1-Fc in a Cell-Based Assay

Figure 16:
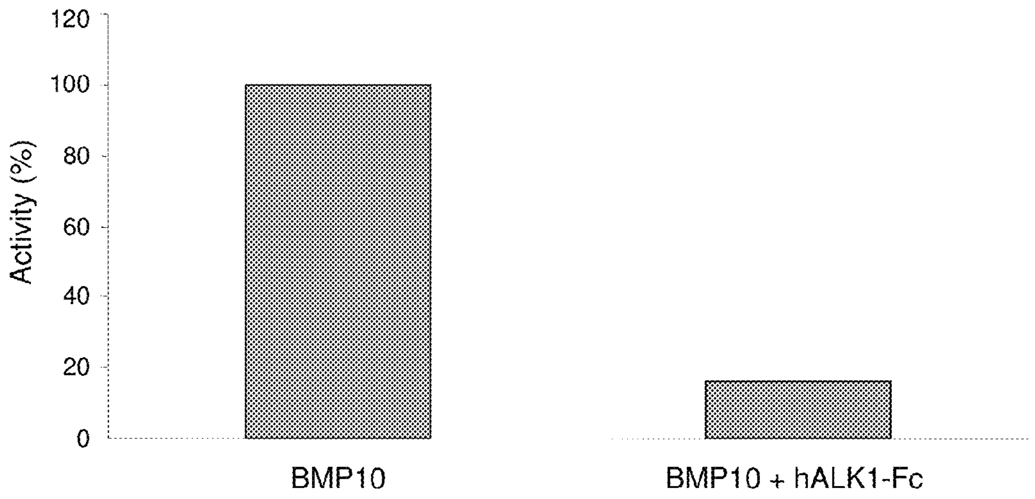
FIG. 16 shows the ability of hALK1-Fc to inhibit by more than 80% the transcriptional reporter activity induced by BMP10 in a cell-based assay.

Effects of hALK-Fc on BMP10 signaling were determined in a cell-based assay, in which human glioblastoma T98G cells were transfected with three plasmids: 1) an expression construct encoding full-length ALK1; 2) a firefly-luciferase reporter construct (see Example 3) responsive to Smad1/5/8-mediated signaling, and 3) a *Renilla*-luciferase control construct. Treatment of transfected cells with recombinant human BMP10 (1 ng/ml) strongly stimulated firefly luciferase activity relative to *Renilla* luciferase activity (FIG. 16). Omission of the ALK1 expression construct reduced BMP10-stimulated activity by approximately two-thirds (data not shown), thus implicating ALK1 as a major mediator of the BMP10 signal. Treatment of fully transfected cells with hALK1-Fc (65 ng/ml) and BMP10 (1 ng/ml) reduced the transcriptional response compared to BMP10 alone by more than 80% (FIG. 16). Together, these results indicate that ALK1 is a major mediator of BMP10 signaling and that ALK1-Fc can markedly inhibit such signaling.

Example 13

Figure 17:
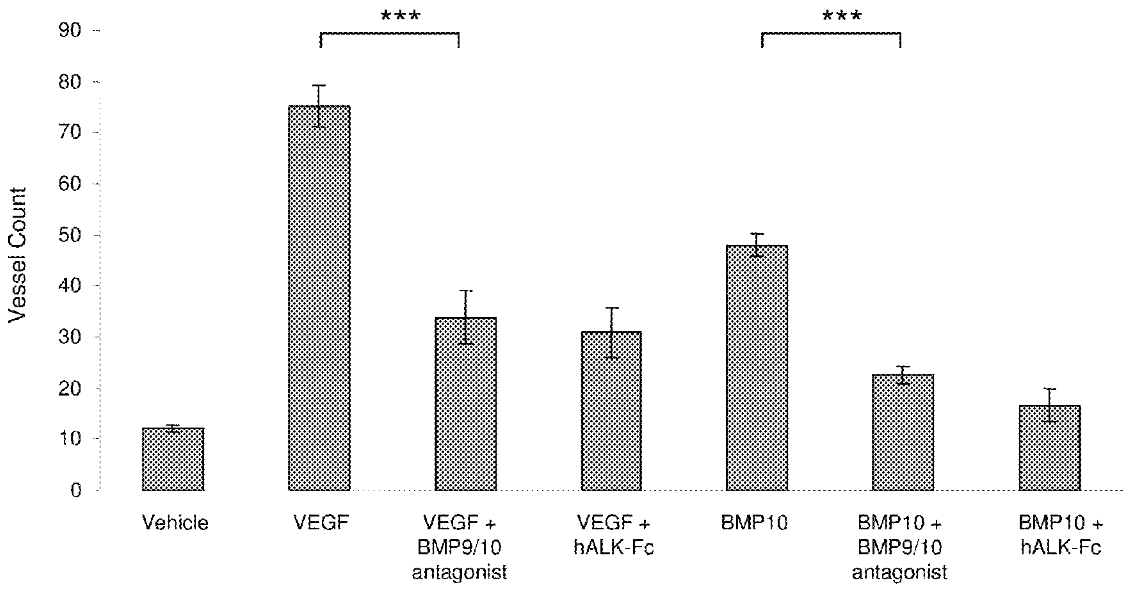
FIG. 17 shows the effects of a BMP9/10 antagonist or hALK1-Fc on VEGF- or BMP10-stimulated angiogenesis in a chick chorioallantoic membrane (CAM) assay. Data are means±SEM; ***, $p<0.0001$. BMP9/10 antagonist reduced both VEGF-stimulated angiogenesis and BMP10-stimulated angiogenesis by more than 50%, and effects of similar magnitude were obtained with hALK1-Fc.
Figure 18:
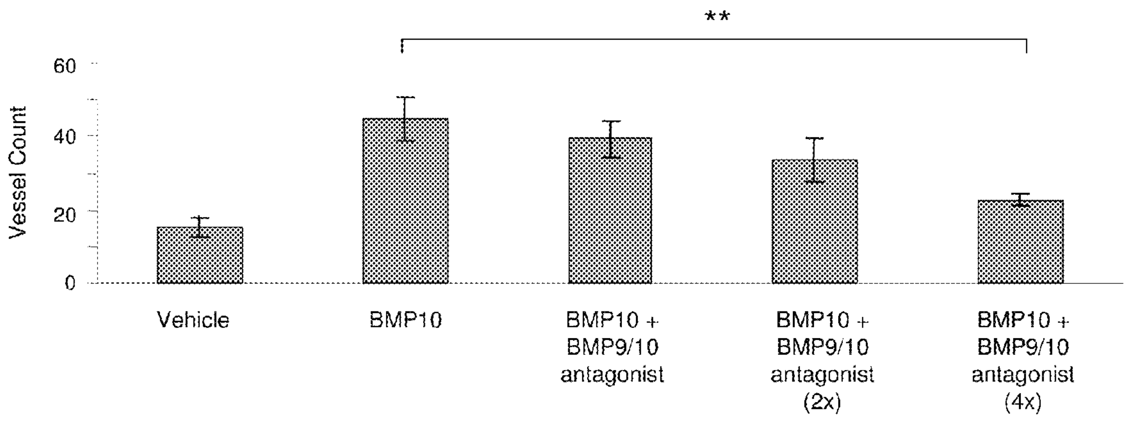
FIG. 18 shows a dose-dependent inhibition of BMP10-stimulated angiogenesis by a BMP9/10 antagonist in a chick chorioallantoic membrane (CAM) assay. Data are means±SEM; **, $p<0.01$.

BMP9/10 Antagonists Inhibit VEGF- and BMP10-Induced Angiogenesis in a CAM Assay A chick chorioallantoic membrane (CAM) assay system was used to investigate the effect of BMP9/10 antagonists on angiogenesis. In the first experiment, VEGF and BMP10 were used separately to promote angiogenesis. Compared to VEGF alone, combined treatment with VEGF (50 ng daily) and BMP9/10 antagonist (82 pmol daily) reduced vessel count by more than half (FIG. 17). Compared to BMP10 alone, combined treatment with BMP10 (50 ng daily) and BMP9/10 antagonist (82 pmol daily) also reduced vessel count by more than half (FIG. 17). Similar inhibitory effects on VEGF- or BMP10-induced angiogenesis were observed with hALK1-Fc (41 pmol daily). In a second CAM experiment, three doses of a different BMP9/10 antagonist were evaluated for their ability to inhibit angiogenesis induced by a higher dose (150 ng) of BMP10. A clear dose-dependent inhibition of BMP10-stimulated angiogenesis was observed, with the highest dose of BMP9/10 antagonist (164 pmol daily, 4×) resulting in a 49% reduction in vessel count compared to BMP10 alone (FIG. 18). These data demonstrate that, in contrast to BMP9, BMP10 stimulates angiogenesis, and that antagonists of BMP10 can inhibit angiogenesis. This result is in contrast to published literature suggesting that BMP10 should, like BMP9, inhibit angiogenesis. These in vivo data demonstrate that BMP9 and/or BMP10 antagonists and ALK1-Fc can significantly inhibit angiogenesis induced by either VEGF or BMP10.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject inventions are explicitly disclosed herein, the above specification is illustrative and not restrictive. Many variations of the inventions will become apparent to those skilled in the art upon review of this specification and the claims below. The full scope of the inventions should be determined by reference to the claims, along with their full scope of equivalents, and the specification, along with such variations.

We claim:

1. A method of inhibiting angiogenesis in a mammal, the method comprising, administering to the mammal an effective amount of an antibody or antigen-binding antibody fragment that binds to BMP10.

2. The method of claim 1, wherein the method further comprises administering a second agent that inhibits angiogenesis.

3. The method of claim 1, wherein the angiogenesis to be inhibited is angiogenesis occurring, in a tumor.

4. The method of claim 1 wherein the mammal has angiogenesis related rheumatoid arthritis and wherein the antibody or antigen-binding antibody fragment inhibits the binding of BMP10 to ALK1.

5. The method of claim 1 wherein the mammal has an angiogenesis related disease of the eye and wherein the antibody or antigen-binding antibody fragment inhibits the binding of BMP10 to ALK1.S.

6. The method of claim 1, wherein the antibody or antigen-binding antibody fragment inhibits the binding of BMP10 to ALK1.

7. A method of inhibiting angiogenesis in a tumor in a mammal, the method comprising, administering to a mammal that has a tumor an effective amount of an antibody or antigen-binding antibody fragment that binds BMP10 and inhibits the binding of BMP10 to ALK1.

* * * * *

UNITED STATES PATENT AND TRADEMARK OFFICE

CERTIFICATE OF CORRECTION

PATENT NO. : 9,452,197 B2
APPLICATION NO. : 14/142094
DATED : September 27, 2016
INVENTOR(S) : Jasbir Seehra et al.

It is certified that error appears in the above-identified patent and that said Letters Patent is hereby corrected as shown below:

In the Claims:

At column 61, claim 3, line 25, "occurring, in a tumor" should read --occurring in a tumor--

At column 62, claim 5, line 19, "ALK1.S" should read --ALK1.--

Signed and Sealed this
Twentieth Day of December, 2016

Michelle K. Lee
*Director of the United States Patent and Trademark Office*